US010793834B2

(12) United States Patent
Poon et al.

(10) Patent No.: US 10,793,834 B2
(45) Date of Patent: Oct. 6, 2020

(54) LIVE-ATTENUATED VIRUS AND METHODS OF PRODUCTION AND USE

(71) Applicant: The University of Hong Kong, Hong Kong (HK)

(72) Inventors: Lit Man Poon, Hong Kong (HK); Lok Yan Fan, Hong Kong (HK)

(73) Assignee: THE UNIVERSITY OF HONG KONG, Hong Kong (HK)

( * ) Notice: Subject to any disclaimer, the term of this patent is extended or adjusted under 35 U.S.C. 154(b) by 0 days.

(21) Appl. No.: 15/174,348

(22) Filed: Jun. 6, 2016

(65) Prior Publication Data

US 2016/0354460 A1 Dec. 8, 2016

Related U.S. Application Data

(60) Provisional application No. 62/171,024, filed on Jun. 4, 2015.

(51) Int. Cl.
*C12N 7/00* (2006.01)
*A61K 39/12* (2006.01)
*A61K 39/00* (2006.01)

(52) U.S. Cl.
CPC ............... *C12N 7/00* (2013.01); *A61K 39/12* (2013.01); *A61K 2039/5254* (2013.01); *C12N 2760/16134* (2013.01); *C12N 2760/16162* (2013.01); *C12N 2760/16234* (2013.01); *C12N 2800/22* (2013.01)

(58) Field of Classification Search
None
See application file for complete search history.

(56) References Cited

U.S. PATENT DOCUMENTS

| 2006/0204976 | A1* | 9/2006 | Plana-Duran | ........ | A61K 39/145 435/6.16 |
| 2010/0209454 | A1* | 8/2010 | Wimmer | .............. | C07K 14/005 424/205.1 |
| 2012/0269849 | A1 | 10/2012 | Wimmer | | |
| 2014/0302077 | A1 | 10/2014 | Anhlan | | |

FOREIGN PATENT DOCUMENTS

| WO | 99028445 | 6/1999 |
| WO | 2008153236 | 12/2008 |
| WO | 2014145092 | 9/2014 |

OTHER PUBLICATIONS

Guionie et al., H5-based DNA constructs derived from selected highly pathogenic H5N1 avian influenza virus induce high levels of humoral antibodies in Muscovy ducks against low pathogenic viruses, 2014, Virology Journal, vol. 11, pp. 1-7.*
Poon et al., Codon usage bias and the evolution of influenza A viruses. Codon Usage Biases of Influenza Virus, 2010, BMC Evolutionary Biology, vol. 10, No. 253, pp. 14.*
Etkind, et al., "Purificastion of imfluenza viral complementary RNA: Its genetic content and activity in wheat germ cell-free extracts", J Virol., 16(61464-75 (1975).
Fancher, et al.,"Codon bias of influenza a viruses and their hosts", AJMB, 1:174-82 (2011).
Gog, et al., "Codon conservation in the influenza A virus genome defines RNA packaging signals", Nucleic Acids Res., 35(6):1897-1907 (2007).
Hilderbrand, et al., "CBDB: The codon bias database", BMC Bioimform., 13:62 (2012).
Hoffmann, et al., "A DNA transfection system for generation of influenza A virus from eight plasmids", PNAS, 97(11):6108-13 (2000).
Holm, "Codon usage and gene expression", Nucleic Acis Res., 14(7):3075-87 (1986).
Karlin, et al., "Why is CpG suppressed in the genomes of virtually all small eukaryotic viruses but not in those of large eukaryotic viruses", J Virol., 68:2889-2897 (1994).
Martin, et al., "RNA Polymerase II-Controlled Expression of Antigenomic RNA Enhances the Rescue Efficacies of Two Different Members of the Mononegavirales Independently of the Site of Viral Genome Replication", J Virology, 80(12):5708-15 (2008).
Moss, et al., "Identification of potential conserved RNA secondary structure throughout influenza A coding regions", RNA, 17:991-1011 (2011).
Mueller, et al., "Live Attenuated Influenza Vaccines by Computer-Aided Rational Design", Nat Biotechnol., 28(1):723-6 (2010).
Nakamura, et al., "Codon usage tabulated from international DNA sequence databases: status for the year 2000", Nucleic Acids Res., 28(1):292 (2000).
Nogales, et al., "Influenza A Virus Attenuation by Codon Deoptimization of the NS Gene for Vaccine Development", J Virology, 88(18):10525-40 (2014).
Quan, et al., "Virus-Like Particle Vaccine Induces Protective Immunity against Homologous and Heterologous Strains of Influenza Virus", J Vorology, 81(7):3514-24 (2007).
Resa-Infante, et al., "The influenza RNA synthesis machine Advances in its structure and function", RNA Blolo., 8(2):207-15 (2011).
Sharp, et al., "Codon usage in yeast: cluster analysis clearly differentiates highly and lowly expressed genes", Nucleic Acids Res., 14(13):5125-43 (1986).
Sharp, et al., "Codon usage patterns in *Escherichia coil*, Bacillus subtilis, *Saccharomyces cerevisiae*, Schlzosaccharomyces pombe, *Drosophila melanogaster* and *Homo sapiens*; a review of the considerable within-species diversity", Nucleic Acids Res., 16:8207-8211 (1968).

(Continued)

*Primary Examiner* — Benjamin P Blumel
(74) *Attorney, Agent, or Firm* — Pabst Patent Group LLP

(57) ABSTRACT

Presented herein are live-attenuated viruses and methods of generating thereof from a parental virus through a plurality of nucleotide substitutions in the viral genome. The nucleotide substitutions result in a change in codon usage bias within codons of one or more protein encoding sequences and no change in amino acid sequences of the proteins. The live-attenuated viruses display unaltered replication in avian hosts for propagation, but attenuated replication in mammalian hosts, when compared to the replication of the parental virus. The live-attenuated viruses in a form of improved vaccines can be used to elicit protective immune responses.

23 Claims, 23 Drawing Sheets

Specification includes a Sequence Listing.

(56) References Cited

OTHER PUBLICATIONS

Spencer, et al., "Genetic code redundancy and its influence on the encoded polypeptides", CSBJ, 1(1):1-8 (2012).
Wan, et al., "Quantitative relationship between synonymous codon usage bias and GC composition across unicellular genomes", BMC, 4(19):1-11 (2004).
WHO, "A revision of the system of nomenclature for influenza viruses: a WHO memorandum", 58(4):585-91 (1980).
Wong, et al., "Codon usage bias and the evolution of influenza A viruses. Codon Usage Biases of Influenza Virus", BMC Evolutionary Biology, 10:253 (2010).
Xu, et al., "Adaption of Seasonal H1N1 Influenza Virus in Mice", PLoS ONE, 6(12):e28901 (2011).
Yang, et al., "Deliberate reduction of hemagglutinin and neuraminidase expression of influenza virus leads to an ultraprotective live vaccine in mice", PNAS, 110(23):9481-6 ) 2013).
Zhi, et al., "Codon Optimization of Human Parvovirus B19 Capsid Genes Greatly Increases Their Expression in Nonpermissive Cells", J Virology, 84(24):13059-62 (2010).
Zhou, et al., "In Vitro Packaging of Adeno-Associated Virus DNA", J. Virol., 72(4):3241-7 (1998).
Baker, et al., "Downregulating viral gene expression: codon usage bias manipulation for the generation of novel influenza A virus vaccines", Future Virol., 10(6):715-30 (2015).

\* cited by examiner

```
           2010       2020       2030       2040       2050       2060       2070       2080       2090       2100
       ....|....|....|....|....|....|....|....|....|....|....|....|....|....|....|....|....|....|....|....|
       GAGTTTTCAAAGATACCGGGATGGGATTCTTCAAGGAAAGCCATTGCTTCTAATACACAATCTGTTTGGGCATAGCCACTTGGTTCATTGTCTTCCGGTA
       ..............T.....................................................................................

2110       2120       2130       2140       2150       2160       2170       2180       2190       2200
       ....|....|....|....|....|....|....|....|....|....|....|....|....|....|....|....|....|....|....|....|
       GTGGACCATCAATTGGGTTAAGTTGCGGTGCTCCAGTTTCGGTATTTTTTGTCCATCTTCCTCTTTCTGAGTACTGGTGTGTCCTGTTGACTGTATCCAT
       ....................................................................................................

2210       2220       2230       2240       2250       2260       2270       2280       2290       2300
       ....|....|....|....|....|....|....|....|....|....|....|....|....|....|....|....|....|....|....|....|
       GGTGTATCCTGTTCCTGTCCCATGGCTGTAAGGAGGGTCACCAGTATAAGGAAAAGTTGTGCTTATAGCATTTTGTGCTGGCACTTTTAAGAAAAGTAAT
       ..............................................................G....................................

2310       2320       2330       2340
       ....|....|....|....|....|....|....|....|
       GTCGGATTGACATCCATTCAAATGGTTTGCCTGCTTTCGCT
       ........................................
```

FIG. 15B-3

```
            10         20         30         40         50         60         70         80         90        100
       ....|....|....|....|....|....|....|....|....|....|....|....|....|....|....|....|....|....|....|....|
       AGTAGAAACAAGGTACTTTTTTGGACAGTATGGATAACAAATAGTAGCATTGCCTCAGCTATCTCAATGCATGTGTTAGGAAGGAGTTGAACCAAGAAGC
       ....................................................................................................

110        120        130        140        150        160        170        180        190        200
       ....|....|....|....|....|....|....|....|....|....|....|....|....|....|....|....|....|....|....|....|
       ATTAAGCAAAACCCAGGGATCATTAATCAGGCACTCCTCAATTGCTTCATATAGCCCCCCAAGATCAAAGGTCCCAGGTTCCAGATTGTCCCTAAGAGCC
       ...............................................................................................G....

210        220        230        240        250        260        270        280        290        300
       ....|....|....|....|....|....|....|....|....|....|....|....|....|....|....|....|....|....|....|....|
       TGAACAATGAGGAGCAACTTTCTTGACTCAGCTGAAAATCCTTCTAATTGTGGAGATGCATACAGGCTATTGAATACTGACTTAGCCAACAGTGTCCTGC
       ................T...............................................G.......A.....G.....................

310        320        330        340        350        360        370        380        390        400
       ....|....|....|....|....|....|....|....|....|....|....|....|....|....|....|....|....|....|....|....|
       ATACTTTCCCAATGGAACCTTCTTCCACTCCTTTTGGTGACTCTCCAATGGGCCATGTTCTGATTTATTCTCAAAAAACTCTTTTGTCATGTCTTTCTC
       .C..............................T.............................C...................................

410        420        430        440        450        460        470        480        490        500
       ....|....|....|....|....|....|....|....|....|....|....|....|....|....|....|....|....|....|....|....|
       TTTGACAGAGGACTCAGCTTCAATCATGCTCTCTATTTGTTGGAGGGATTGGAGGAGGCAACGCCTCATCTCCATTCCCCATTCATTTTAATTTTTGAG
       .........G..............T.........C..................C..........................................G..

510        520        530        540        550        560        570        580        590        600
       ....|....|....|....|....|....|....|....|....|....|....|....|....|....|....|....|....|....|....|....|
       GTTCCATTTGTCCTTACATACAAGAACATGGGCCTTGACACTTGGCCTATTGCACTCCTTAGAAGCATATCTCCTATCTCAAGAACGCAGTACTTCTCCC
       .....G............G.................................................................................

610        620        630        640        650        660        670        680        690        700
       ....|....|....|....|....|....|....|....|....|....|....|....|....|....|....|....|....|....|....|....|
       ATTTGTGTGGCTCAAGTCTTGGGTCAGTGAGGGAAAACTCCATGCTCACAAAGTTTACCACATCGGTGTCATTCCTTAAGTGAGATCTTCCTTTTACGAT
       .......................T...........G......G.............G..............................C...........

710        720        730        740        750        760        770        780        790        800
       ....|....|....|....|....|....|....|....|....|....|....|....|....|....|....|....|....|....|....|....|
       GAAGCCGTACAAATTGGTCTTTCTCCTTCCCTCTTTAGTTCTACATTTGCTTATCATGGGAATTAGTTGGAAATCATCCATTGCTGCACAGGATGCATTG
       .........G.G...............T................................G.................................A....

810        820        830        840        850        860        870        880        890        900
       ....|....|....|....|....|....|....|....|....|....|....|....|....|....|....|....|....|....|....|....|
       AGCAAAGCAGTATTAATGTATACCCCCTTCATTATATATTCTGTGGCTCTGCAATGGGACACCTCAGCTGTGAAGTAATTCCTTCTCATGCTTGCAATGT
       .....G..........C.....................C......................................G.....................

910        920        930        940        950        960        970        980        990       1000
       ....|....|....|....|....|....|....|....|....|....|....|....|....|....|....|....|....|....|....|....|
       GTTCAATCGGAGCCACATCTTCTCCAATCTCATCAAGCTCTATCCAGATTGAATCGGTCAGCTCGCATGCCTTGTTGAACTCATTCTGGATCCAACTTGA
       .........G...........................C........................T...................................
```

```
              1010       1020       1030       1040       1050       1060       1070       1080       1090       1100
        ....|....|....|....|....|....|....|....|....|....|....|....|....|....|....|....|....|....|....|....|
        TAGGGAGAGTTGAACCTTGCATCAAAGAGCACATCCTGGGATCCATTCCGGTGCGGACAAGAGCTCTTGTCCTCTGGTAAGTTGTATCATTCAAATTAGA
        ..........C................G...............G...................A...............A.....................

1110       1120       1130       1140       1150       1160       1170       1180       1190       1200
        ....|....|....|....|....|....|....|....|....|....|....|....|....|....|....|....|....|....|....|....|
        ATGCCAGATCATAATGTGAGTCAAACCAGCCGTTGCATCATCACCATTGTTGGCTTGGCGCCAAATCCGCCTTATTTCTTCTTTGTCATAAAGGACGAGT
        .........................G.........................C........C.....A.................................

1210       1220       1230       1240       1250       1260       1270       1280       1290       1300
        ....|....|....|....|....|....|....|....|....|....|....|....|....|....|....|....|....|....|....|....|
        TCCCTCACCCACTTTCCATCTACTCTCTTGTATATGGGTCCTCCAGTTTTCTTAGGATCTTTCCCCGCGCTGGGATGTTCCTCTAGATATTTATTTCTCC
        .....................A...............C...............................................................

1310       1320       1330       1340       1350       1360       1370       1380       1390       1400
        ....|....|....|....|....|....|....|....|....|....|....|....|....|....|....|....|....|....|....|....|
        TCTCATCAAAAGCAGAGAGCACCATTCTCTCTATTGTTAAGCTGTTCTGGATCAGCCGTCCCTCATAATCATTGAGCTTAAGCTCGGTGCACATTTGGAT
        ................................................................T.........................T............

1410       1420       1430       1440       1450       1460       1470       1480       1490       1500
        ....|....|....|....|....|....|....|....|....|....|....|....|....|....|....|....|....|....|....|....|
        GTAGAATCGCCCAATTCCACCAATCATTCTTCCGACGGATGCTCTGATTTCAGTTGCATTCTGGCGTTCCCCATCAGTCTCCATCTGTTCGTAAGACCGT
        ..............................C.......................................................................

1510       1520       1530       1540       1550       1560
        ....|....|....|....|....|....|....|....|....|....|....|....|
        TTGGTGCCTTGGGACGCCATAACTTTGATGTCACTCAGTGAGTGATTATCTACCCTGCTTTTGCT
        .................................................................
```

```
          10        20        30        40        50        60        70        80        90       100
....|....|....|....|....|....|....|....|....|....|....|....|....|....|....|....|....|....|....|....|
AGTAGAAACAAGGTAGTTTTTACTCTAGCTCTATGCTGACAAAATGATCATCGTCAGCATCCACAGCATTCTGCTGTTCCTCTCGATATTCTTCCCTCA
....,....,....,....,....,....,....,....,....,....,....,....,....,....,....,....,....,....,....,...., 110       120       130       140       150       160       170       180       190       200
....|....|....|....|....|....|....|....|....|....|....|....|....|....|....|....|....|....|....|....|
TAGACTCTGGTACTCCTTCCGTAGAAGGCCCTCTTTTTAAACCGTGTTTAAAGATACGATAAATGCTTTTGGAAAAAAGGCGATCAATAATCCACAATAT
....,....,....,....,....,....,....,....,....,....,....,....,....,....,....,....,....,....,....,...., 210       220       230       240       250       260       270       280       290       300
....|....|....|....|....|....|....|....|....|....|....|....|....|....|....|....|....|....|....|....|
CAAGTGCACAATCCCAATTATACTTGCGGCAACAACAAGAGGATCACTTGAATCGTTGCATCTGCACCCCCATTCGTTTCTGATAGGCCTGTAAATTTTC
....,....,....,....,....,....,....,....,....,....,....,....,....,....,....,....,....,....,....,...., 310       320       330       340       350       360       370       380       390       400
....|....|....|....|....|....|....|....|....|....|....|....|....|....|....|....|....|....|....|....|
AAGGAGATCATTTTTCAGACCAGTGCTAGAGCTAGGATGAGTCCCAATGGCTCTCATTGCCTGCACCATCTGCCTGGCCTGACTAGCAACCTCCATGGCC
....,....,....,....,....,....,....,....,T...,....,C...,....,....,....,....,....,....,....,C...,...., 410       420       430       440       450       460       470       480       490       500
....|....|....|....|....|....|....|....|....|....|....|....|....|....|....|....|....|....|....|....|
TCAGCTGCTTGTTCGCTCGATCCAGCCATTTGCTCCATAGCCTTAGCTGTAGTGCTGGCCAGAACCATTCTGTTCTCATGTCTTATTAATGGATTGGTTG
....,....,A...,....,....,C...,....,....,T...,....,....,....,....,....,....,....,....,....,C...,...., 510       520       530       540       550       560       570       580       590       600
....|....|....|....|....|....|....|....|....|....|....|....|....|....|....|....|....|....|....|....|
TTGTTACCATTTGCCTGTGAGACTTATGCTGGGAGTCGGCAATCTGTTCACAGGTTGCACATATAAGGCCAAATGCTGATTCGGTGGTCACAGCCCCCAT
....,C...,....,C...,....,T...,....,....,....,A...,....,....,....,G...,....,....,T...,....,A...,...., 610       620       630       640       650       660       670       680       690       700
....|....|....|....|....|....|....|....|....|....|....|....|....|....|....|....|....|....|....|....|
CCTGTTGTATATGAGTCCCATACAACTGGCAAGTGCACCAGCAGAATAACTGAGTGCTATTTCTTTGGCCCCATGGAATGTTATCTCCCTCTTAAGCTTT
....,....,....,....,T...,....,....,G..G.,....,....,....,G...,....,C...,....,....,....,....,T....C..., 710       720       730       740       750       760       770       780       790       800
....|....|....|....|....|....|....|....|....|....|....|....|....|....|....|....|....|....|....|....|
CGATAAAGTTTGACTGCTCTGTCCATATTATTTGGATCCCCATTCCCATTAAGGGCATTTTGGACAAAGCGTCTACGCTGCAGTCCTCGCTCACTGGGCA
..G.,....,....,....,....,G...,....,G...,....,G...,....,....,....,....,....,....,....,....,....,...., 810       820       830       840       850       860       870       880       890       900
....|....|....|....|....|....|....|....|....|....|....|....|....|....|....|....|....|....|....|....|
CGGTGAGCGTGAACACAAATCCTAAAATCCCCTTAGTCAGAGGTGACAGGATTGGTCTTGTCTTTAGCCACTCCATGAGAGCCTCAAGATCGGTATTCTT
....,....,....,C....A...,....,....,....,....,....,....,....,....,....,....,....,....,....,....,...., 910       920       930       940       950       960       970       980       990      1000
....|....|....|....|....|....|....|....|....|....|....|....|....|....|....|....|....|....|....|....|
TCCAGCAAATACATCTTCAAGTCTCTGTGCGATCTCGGCTTTGAGGGGGCCTGACGGGATGATAGAGAGAACGTACGTTTCGACCTCGGTTAGAAGACTC
....,....,....,....,....,....,....,....,....,....,....,....,....,....,....,....,....,....,....,...., 1010      1020
....|....|....|....|..
ATCTTTCAATATCTACCTGCTTTTGCT
....,....,....,....,....,..
```

FIG. 15G

```
            10        20        30        40        50        60        70        80        90       100
    ....|....|....|....|....|....|....|....|....|....|....|....|....|....|....|....|....|....|....|....|
    AGTAGAAACAAGGGTGTTTTTTATCACTAAATAAGCTGAAACGAAAACGTTCTAATCTCTTGTTCCACTTCAAATAATAGCTGTAATGCTTGCATAAATG 110       120       130       140       150       160       170       180       190       200
    ....|....|....|....|....|....|....|....|....|....|....|....|....|....|....|....|....|....|....|....|
    TTATTTGCTCAAAACTATTCTCTGTCGTCTTCAATTTATGCCTCACTTCTTCAATCAGCCATCTTACTTCTTCAAACTTCTGACCTAGTTGTTCCCGCCA 210       220       230       240       250       260       270       280       290       300
    ....|....|....|....|....|....|....|....|....|....|....|....|....|....|....|....|....|....|....|....|
    TTTTCCGTTTCTGTGTTGTAGTGAATGGAGGTCCCCCAGTCTCATTACTGCTTCTCCAAGCGAATCTCTGTAGAGTTTCAGAGACTCGAACTGTGTTATC 310       320       330       340       350       360       370       380       390       400
    ....|....|....|....|....|....|....|....|....|....|....|....|....|....|....|....|....|....|....|....|
    ATTCCATTCAAGTCCCCCGATGAGGACCCCAATTGCATTTTTGACATCCTCATTAGTATGTCCTGGAAAAGAAGGCAATGGTGAAATTTCGCCAACAATT
    .............................................................................................A......

410       420       430       440       450       460       470       480       490       500
    ....|....|....|....|....|....|....|....|....|....|....|....|....|....|....|....|....|....|....|....|
    GCTCCCTCTTCGGTGAAAGCCCTTAGTAATGTCAGATTCTCCAACCGGTCAAAAATCACACTGAAATTCGCTTTCAGTATGATGTTCTTATCCATTATTG
    ..............A.....T.....................G.GT...................G................................

510       520       530       540       550       560       570       580       590       600
    ....|....|....|....|....|....|....|....|....|....|....|....|....|....|....|....|....|....|....|....|
    CCTGGTCCATTCTGACACAAAGAGGGCCAGCCACTTTTTGCTTGGGCATGAGCATGAACCAGTCCCTTGACATTTCTTCAACAGTCATGTCAGTTAGGTA
    ..........G.......A...........C.....T.............T.....C.....C..............C..........

610       620       630       640       650       660       670       680       690       700
    ....|....|....|....|....|....|....|....|....|....|....|....|....|....|....|....|....|....|....|....|
    CCGCGAAGCAAGTGCGGAGGCCATGGTCATTTTAAGTGCCTCATCGGATTCTTCTTTCAGAATCCTCTCTACTATTTGCTTTCCAACACAAGTAGCTGTT
    ...T..................................................T.......................C................

710       720       730       740       750       760       770       780       790       800
    ....|....|....|....|....|....|....|....|....|....|....|....|....|....|....|....|....|....|....|....|
    TCGATGTTCAGACCGAGAGTGCTGCCTCTTCCCTTTAGAGACTTCTGATCTCGGCGAAGCCGATCAAGGAAGGGGGCATCGCCTAGATCTTGGTCTGCAG 810       820       830       840       850       860       870       880       890
    ....|....|....|....|....|....|....|....|....|....|....|....|....|....|....|....|....|....|
    CTTGTTTGCGGACATGCCAAAGGAAGCAATCTACCTGAAAGCTTGACACAGTGTGGGAATCCATTATGTCTTTGCCACCCTGCTTTTGCT
```

FIG. 15H

LIVE-ATTENUATED VIRUS AND METHODS OF PRODUCTION AND USE

CROSS REFERENCE TO RELATED APPLICATIONS

This application claims benefit of U.S. Provisional Application No. 62/171,024, filed Jun. 4, 2015, which is incorporated hereby by reference in its entirety.

FIELD OF THE INVENTION

The disclosed invention is generally in the field of live-attenuated viruses and specifically in the area of making and using live-attenuated influenza viruses.

BACKGROUND OF THE INVENTION

Influenza is one of the medically important viruses throughout centuries. Amongst all the well-established control measures for this virus, vaccination is one of the most effective ways to prevent influenza infections. Current commercially available vaccines can mainly be classified into inactivated or live-attenuated vaccines. Both types of vaccines have their limitations. Inactivated vaccines, also known as killed vaccines, contain non-infectious viral protein products and this kind of vaccines can induce, antibody-mediated immunity, but not cell-mediated immunity after vaccination.

Thus, inactivated vaccines fail to stimulate one of the important arms of the adaptive immune system. By contrast, live-attenuated vaccines can induce both antibody-mediated and cell-mediated immune responses. However, many studies indicate that the current commercial live-attenuated vaccines are not immunogenic enough to induce robust immune responses. The poor immunogenicity of current commercial live-attenuated vaccine is primarily due to the mutations (also known as cold-adapted mutations) used for attenuating the virus.

The most common method to make the attenuated vaccine involves passing the virus through a series of cell cultures or animal embryos (typically chick embryos) under low temperature conditions, for example, 24° C. Using chick embryos as an example, the virus is grown in different embryos in a series. With each passage, the virus becomes better at replicating in eggs, but reduces its ability to replicate in human cells. A virus targeted for use in a vaccine can be grown through—"passaged" through—upwards of 200 different embryos or cell cultures. Eventually, the virus will be attenuated in human cells, and it can replicate in a restricted conditions. Using cold-adapted virus as an example, its replication is restricted in the upper respiratory tract where temperatures do not exceed 32-33° C. All of the methods that involve passing a virus through a non-human host produce a version of the virus that can still be recognized by the human immune system, but cannot replicate well in a human host. Therefore the attenuated virus can be used in a vaccine.

The current live attenuated influenza vaccine such as FluMist contains cold adapted viruses. It is believe that the cold adapted vaccines are not immunogenic enough to induce robust immune response possibly because the virus can only replicate at the upper respiratory tract (33° C.).

The cold-adapted mutations restrict the virus to grow at low temperature (33° C.). Viruses with these "cold-adapted mutations" would grow poorly at normal body temperature (37° C.). Hence, live-attenuated vaccines of this kind are only able to replicate at the upper respiratory tract (33° C.) after intranasal vaccination, resulting in a limited vaccine-induced immune responses. In additions, this virus attenuation strategy largely relies on 5 mutations located in 3 of the influenza A viral genes. Thus, there is still a safety concern about the possible unpredictable consequences causing by gene reassortments or reverse mutations.

There are other approaches to generate live-attenuated viruses. These attenuated viruses are shown to induce protective immune responses in various experimental models. However, these approaches often transform the studied viruses into slow-replicating viruses and these attenuated viruses normally fail to produce high virus titers in eggs. As a great majority of vaccine manufacturers use fertilized chicken eggs to produce influenza vaccines, these attenuated viruses are therefore unlikely to be produced in a cost-effective manner.

There remains a need for live, attenuated viruses for use as vaccines which produce both antibody-mediated and cell-mediated immune responses in the host and high virus titers in eggs.

Therefore, it is an object of the present invention to provide improved live-attenuated viruses with reduced replication in mammalian hosts, but not avian hosts.

It is a further object of the present invention to provide improved live-attenuated viruses that elicit antibody-mediated and cell-mediated immune responses in the mammalian host comparable to those of an unattenuated parent virus.

It is another object of the present invention to provide improved live-attenuated viruses that have substantially the same replication at 33° C. and 37° C.

It is yet another object of the present invention to provide improved live-attenuated viruses that produce immune protection towards homologous or heterologous viral challenges.

It is yet another object of the present invention to provide methods of making the improved live-attenuated viruses.

It is yet another object of the present invention to provide methods of using the improved live-attenuated viruses.

BRIEF SUMMARY OF THE INVENTION

Provided herein are improved live-attenuated viruses genetically engineered from wild type viruses. The live-attenuated viruses have a genome with codons mutated to have an avian codon usage bias, such as avian viral codon usage bias. The codons with an avian codon usage bias are generally present at conserved sites at the amino acid level and absent from genomic regions involving packaging or splicing, or overlapping reading frames encoding multiple proteins.

In one aspect, the codons of the live-attenuated viruses mutated to have avian codon usage bias are synonymous substitutions. In another aspect, the codons of the live-attenuated viruses mutated to have avian codon usage bias are silent mutations. Typically, the live-attenuated viruses do not have any amino acid mutations relative to the wild type viruses from which they were derived. In certain forms the live-attenuated viruses are genetically engineered from influenza type A or influenza type B virus.

Generally, the codons having an avian viral codon usage bias are randomly but evenly distributed in the genome of the live-attenuated virus. Typically, the codons having an avian viral codon usage bias are present in at least one gene, in at least two genes, in at least three genes, in at least four genes, in at least five genes, in at least six genes in at least seven genes, in at least eight genes. The codons having an avian viral codon usage bias can be present in at least three genes. The codons having an avian codon usage bias can be present in at least eight genes.

Typically, the live-attenuated viruses presented herein have slower replication in a mammalian host but not in an avian host, when compared to the replication of the wild type virus in the respective hosts. The live-attenuated viruses can produce antibody-mediated immunity similar to that produced by the wild type virus. The live-attenuated viruses can also produce cell-mediated immunity similar to that produced by the wild type virus.

Generally, the live-attenuated viruses replicate at substantially the same rate at 33° C. and at 37° C. In some forms, the live-attenuated viruses can be devoid of any temperature-sensitive mutations relative to the wild type virus.

Different forms of the live-attenuated viruses can produce protective immune responses in a mammalian host against homologous and heterologous viral challenges. In some forms, the live-attenuated viruses described herein can be master strains for production of vaccines. Different forms of the live-attenuated viruses, when used as vaccines, can provide immunity against the same or different viral subtype as the one used in vaccination. Therefore, the live-attenuated viruses described herein can produce homosubtypic immunity/protection, heterosubtypic immunity/protection, or both.

The live-attenuated viruses can include one or more sections of their genomes mutated relative to the wild type virus. In some forms, all the sections of the viral genome, encompassing all the genes, are mutated in the live-attenuated virus. The degree of genome mutation can be chosen so as to alter the rate of replication of the live-attenuated virus in the mammalian host. The degree of genome mutation can also be chosen so as to alter the level of homosubytpic immunity/protection, heterosubtypic immunity/protection, or both.

Alternatively, in other forms, only one or some sections of the viral genome are mutated in the live-attenuated virus. For example, one or more of sections of the viral genome, such as segments or genes, are mutated relative to the corresponding sections of the wild type virus from which they were derived. The live-attenuated viruses can typically have a genome from more than one viral strain or subtype. For example, in some forms of the disclosed live-attenuated influenza virus, the segments coding for internal genes (PB2, PB1, PA, NP, M and NS) can be from one strain or subtype, and the surface glycoprotein coding genes (hemagglutinin (HA) and neuraminidase (NA)) can be from another strain or subtype. In the live-attenuated viruses, any number of the internal genes, any number of the surface glycoprotein coding genes, any number of the internal genes together with any number of the surface glycoprotein coding genes, or all of the genes can be mutated to have avian codon usage bias. The live-attenuated viruses can be used as master strains in vaccinations. In some forms, the can produce heterosubtypic immunity in the vaccinated subject.

Provided herein are also methods for making and using the live-attenuated viruses. Also provided are improved pharmaceutical compositions, such as vaccines, containing the live-attenuated viruses.

Disclosed are live-attenuated viruses having a genome genetically engineered from a wild type virus to have mutated codons having an avian viral codon usage bias. The mutated codons having an avian viral codon usage bias are typically present at conserved sites at the amino acid level, absent from genomic regions involving packaging, splicing, overlapping reading frames encoding multiple proteins, or combinations thereof, or both.

In some forms, the mutated codons having an avian viral codon usage bias are synonymous substitutions. In some forms, the mutated codons having an avian viral codon usage bias are silent mutations. In some forms, the live-attenuated virus does not have any amino acid mutations relative to the wild type virus. In some forms, the mutated codons having an avian viral codon usage bias are randomly but evenly distributed in the genome. In some forms, the mutated codons having an avian viral codon usage bias are present in at least one gene, in at least two genes, in at least three genes, in at least four genes, in at least five genes, in at least six genes, in at least seven genes, or in at least eight genes.

In some forms, the live-attenuated virus has slower replication in a mammalian host but not in an avian host, when compared to the replication of the wild type virus in the respective hosts. In some forms, the live-attenuated virus produces antibody-mediated immunity similar to that produced by the wild type virus. In some forms, the live-attenuated virus produces cell-mediated immunity similar to that produced by the wild type virus. In some forms, the live-attenuated virus produces antibody-mediated immunity and cell-mediated immunity similar to that produced by the wild type virus. In some forms, the live-attenuated virus replicates at substantially the same rate at 33° C. and at 37° C.

In some forms, the live-attenuated virus produces a protective immune response in a mammalian host against homologous and heterologous viral challenges. In some forms, the wild type virus is influenza type A or influenza type B. In some forms, the live-attenuated virus is 8-mut. In some forms, the live-attenuated virus does not have any temperature-sensitive mutations relative to the wild type virus. In some forms, the live-attenuated virus is a master strain. In some forms, the live-attenuated viruses described herein can produce immune response against homosubtypic viruses (homosubtypic protection), against heterosubtypic viruses (heterosubtypic protection), or against both homosubtypic and heterosubtypic viruses (homosubtypic and heterosubtypic protection).

In some forms, the avian viral codon usage bias is the ratio of the synonymous codons for each given amino acid in a gene, segment, or entire coding sequence of avian viruses of the same type as the wild type virus or of a single or set of reference avian viruses.

Also disclosed are methods of making the disclosed live-attenuated viruses by mutating one or more codons of the wild type virus that do not have avian viral codon usage bias into codons having avian viral codon usage bias to produce mutated codons having an avian viral codon usage bias. In some forms, the live-attenuated virus can be made by identifying regions of conserved sites at the amino acid level in the genome of the wild type virus; identifying codons in the conserved sites of the wild type virus that do not have avian viral codon usage bias; and mutating one or more of the identified codons of the wild type virus that do not have avian viral codon usage bias into codons having avian viral codon usage bias to produce mutated codons having an avian viral codon usage bias.

In some forms, the method can further include producing the live-attenuated virus by contacting a host cell with one or more nucleic acid regions collectively forming the genome of the live-attenuated virus, wherein at least one of the regions comprises the mutated codons. In some forms, at least two, at least three, at least four, at least five, at least six, at least seven, or at least eight regions comprise the mutated codons.

Also disclosed are vaccine compositions comprising the disclosed live-attenuated viruses. In some forms, the vaccine composition can further comprise a carrier. In some forms, the vaccine composition can further comprise an adjuvant.

Also disclosed are methods involving administering to a subject in need thereof an effective dose of a disclosed live-attenuated virus.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several forms of the disclosed method and compositions and together with the description, serve to explain the principles of the disclosed method and compositions.

FIG. 6 is a graph showing a change in relative weight (%) at various days post-challenge of mice vaccinated intranasally with PBS (■) (mock vaccinated control) or $6.75 \times 10^5$ p.f.u. of 8-mut virus (▲) (subtype H1N1). At day 28 post-vaccination, mice were challenged with $6.71 \times 10^5$ PFU of MA20C virus (mouse-adapted A/HK/68; subtype H3N2). Body weights of 6 mice were monitored for 14 days. Vaccinated mice had less weight loss and earlier recovery. Data represent mean±SD. * indicates p-value <0.05, ** indicates p-value <0.001.

FIGS. 7A and 7B are graphs showing growth kinetics measured in viral titer (pfu/ml) as a function of time (hours post-infection) of wild type (WT) or mutated viruses. Growth kinetics of WT and mutated viruses were characterized in MDCK cells (0.001 m.o.i.). Tissue culture supernatant was collected at the indicated post-infection time points. Viral titers were determined by plaque assays on MDCK cells. Virus replication kinetics of mutants containing 1 (FIG. 7A) or multiple (FIG. 7B) mutated segment(s) are shown as indicated.

(FIG. 9B); and the MDCK cells were infected at 0.001 m.o.i. (FIG. 9C) at 37° C. Allantoic fluid of eggs or tissue culture supernatant of cells were collected at 24, 48 and 72 hours post-infection. Viral titers were determined by plaque assays on MDCK cells. Data represent mean±SD. * indicates p-value <0.05, ** indicates p-value <0.001.

5-week-old mice were infected intranasally with the recombinant viruses at 1×10$^4$ PFU/dose and body weights were monitored for 14 days.

Figure 11A:
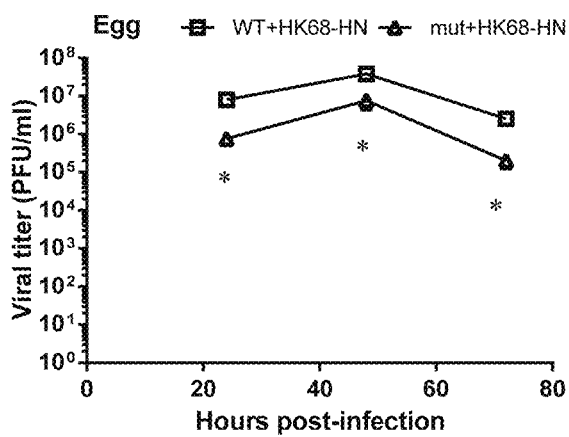
Figure 11B:
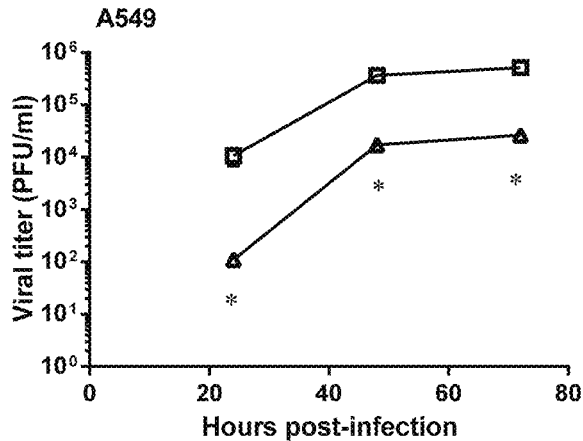

FIGS. 11A and 11B are graphs showing growth kinetics of a recombinant virus with internal genes derived from the Brisbane/07 virus (subtype H1N1), and the surface glycoproteins HA and NA derived from the A/HK/1/68 virus (subtype H3N2) (WT+HK68-HN, (□)) and a recombinant virus with internal genes derived from the 8-mut and the surface glycoproteins HA and NA derived from the wild type HK68 virus (Mut+HK68 HN, (Δ)). The growth kinetics were measured in viral titer (PFU/ml) as a function of time (hours post-infection). The embryonated eggs were infected at 100 PFU (FIG. 11A). The human A549 cells were infected at 0.01 m.o.i. at 37° C. (FIG. 11B). Allantoic fluid of eggs or tissue culture supernatant of cells were collected at 24, 48 and 72 hours post-infection. Viral titers were determined by plaque assays on MDCK cells. Data represent mean±SD. * indicates p-value <0.05.

Figure 12:
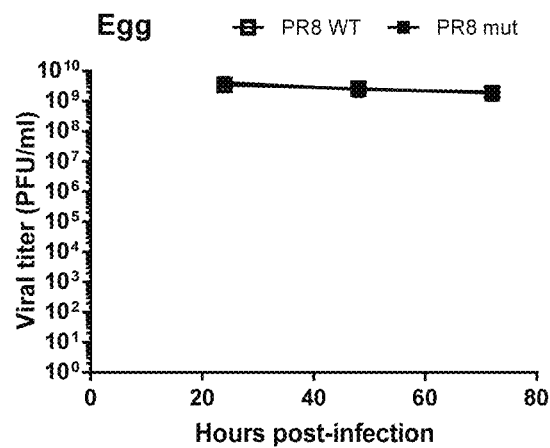

FIG. 12 is a graph showing the growth kinetics as change in viral titer (PFU/ml) over time (hours post infection) of wild-type A/PR/8/34 (PR8 WT, □) and its codon bias mutant (PR8 mut, (■)) in eggs. Growth kinetics of PR8 WT and mut viruses were performed in embryonated eggs at 100 PFU at 37° C. Allantoic fluid of eggs was collected at 24, 48 and 72 hours post-infection. Viral titers were determined by plaque assays on MDCK cells.

Figure 13A:
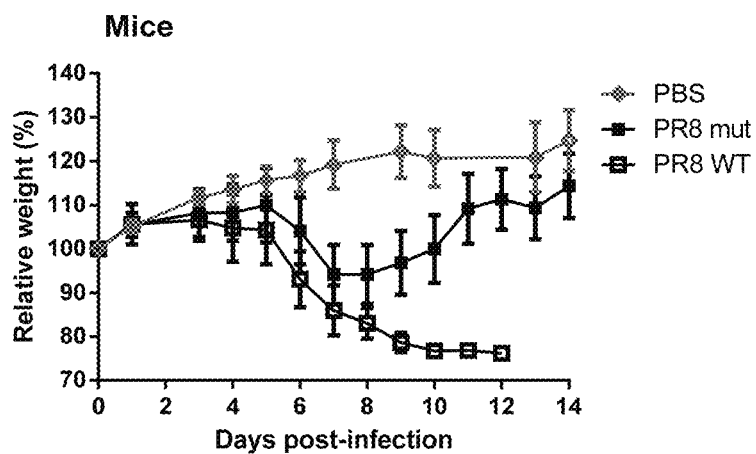
Figure 13B:
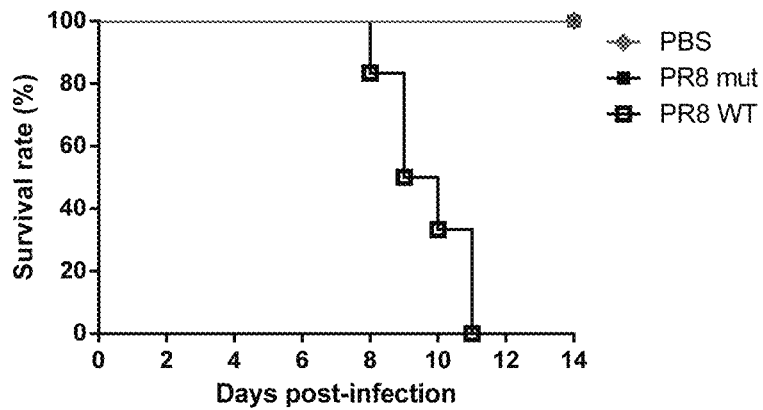

FIG. 13A is a graph showing change in relative weight (%) of mice over time (days post-infection) following administration of PBS, or infection with PR8 WT (□) or PR8 mut (■) viruses. Groups of 6 5-week-old mice were infected intranasally with 100 PFU/dose of PR8 WT or PR8 mut viruses, or received PBS. FIG. 13B is a graph showing the survival rate (%) over time (days post-infection) of the mice following administration of PBS, or infection with PR8 WT (=) or PR8 mut (■) viruses. Body weight data represent mean±SD.

Figure 14A:
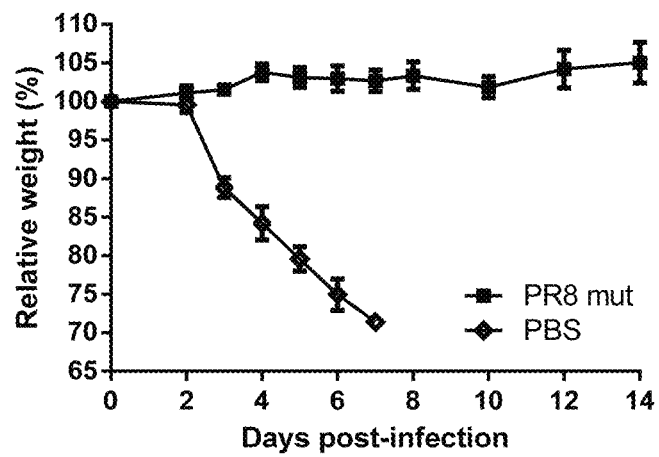
Figure 14B:
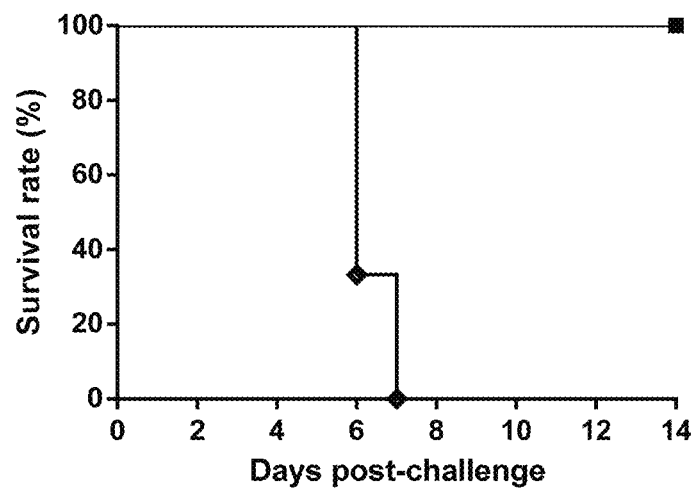

FIG. 14A is a graph showing change in relative weight (%) of mice over time (days post-infection) following intranasal vaccination with 100 PFU/dose of the codon bias mutant of A/PR/8/34 (PR8 mut, (■)) virus or PBS (◇). At day 28 post-vaccination, mice were challenged with 10LD$_{50}$ (2100 PFU/dose) of wild-type A/PR/8/34 virus. Body weight data represent mean±SD. FIG. 14B is a graph showing the survival rate (%) over time (days post-challenge) of the mice vaccinated with either the codon bias mutant of A/PR/8/34 (PR8 mut, (■)) virus or PBS (◇), and challenged with the wild-type A/PR/8/34 virus 28 days post-vaccination.

Figure 15A-1:
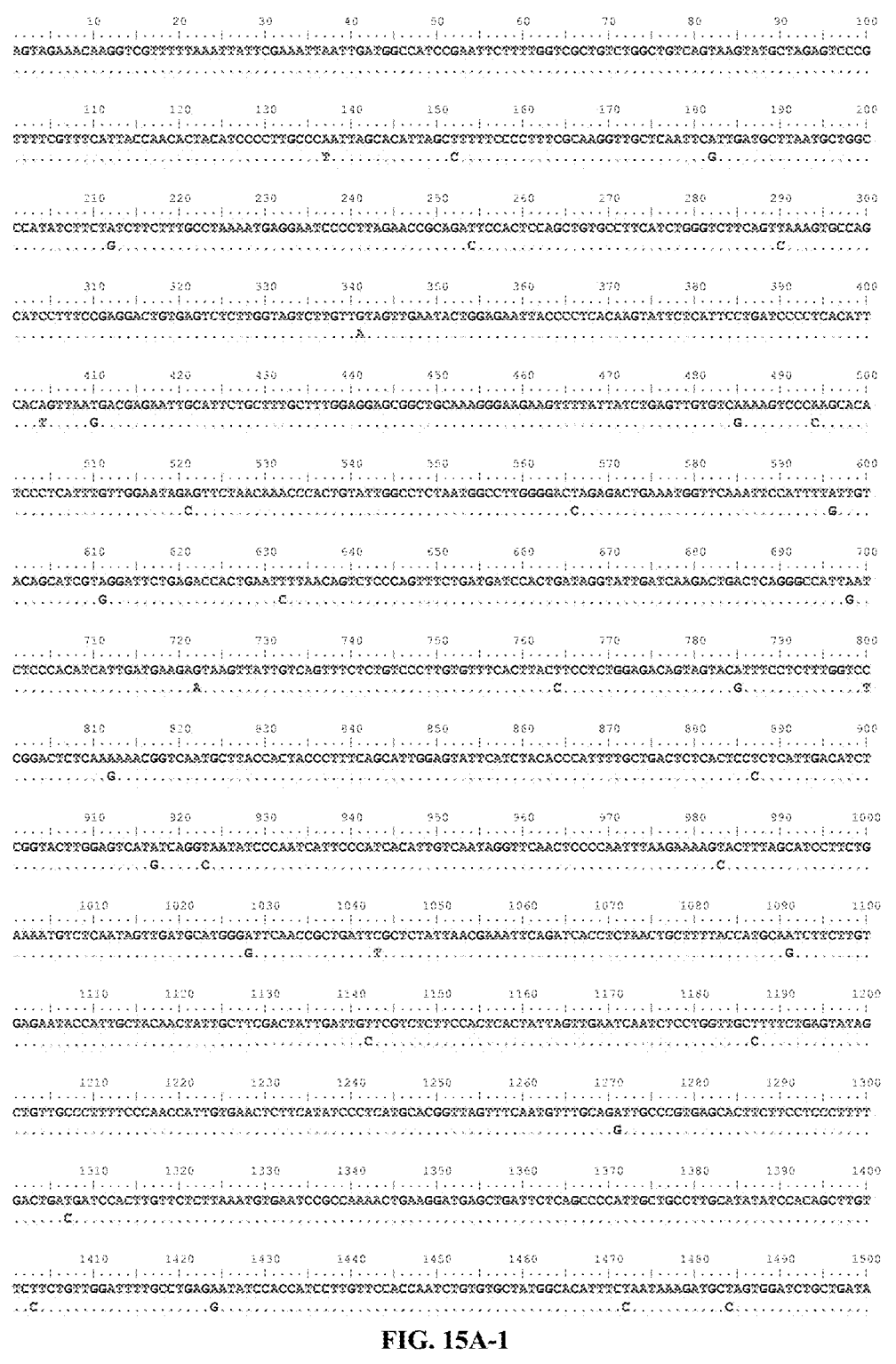
Figures 15A-2, 15B-1:
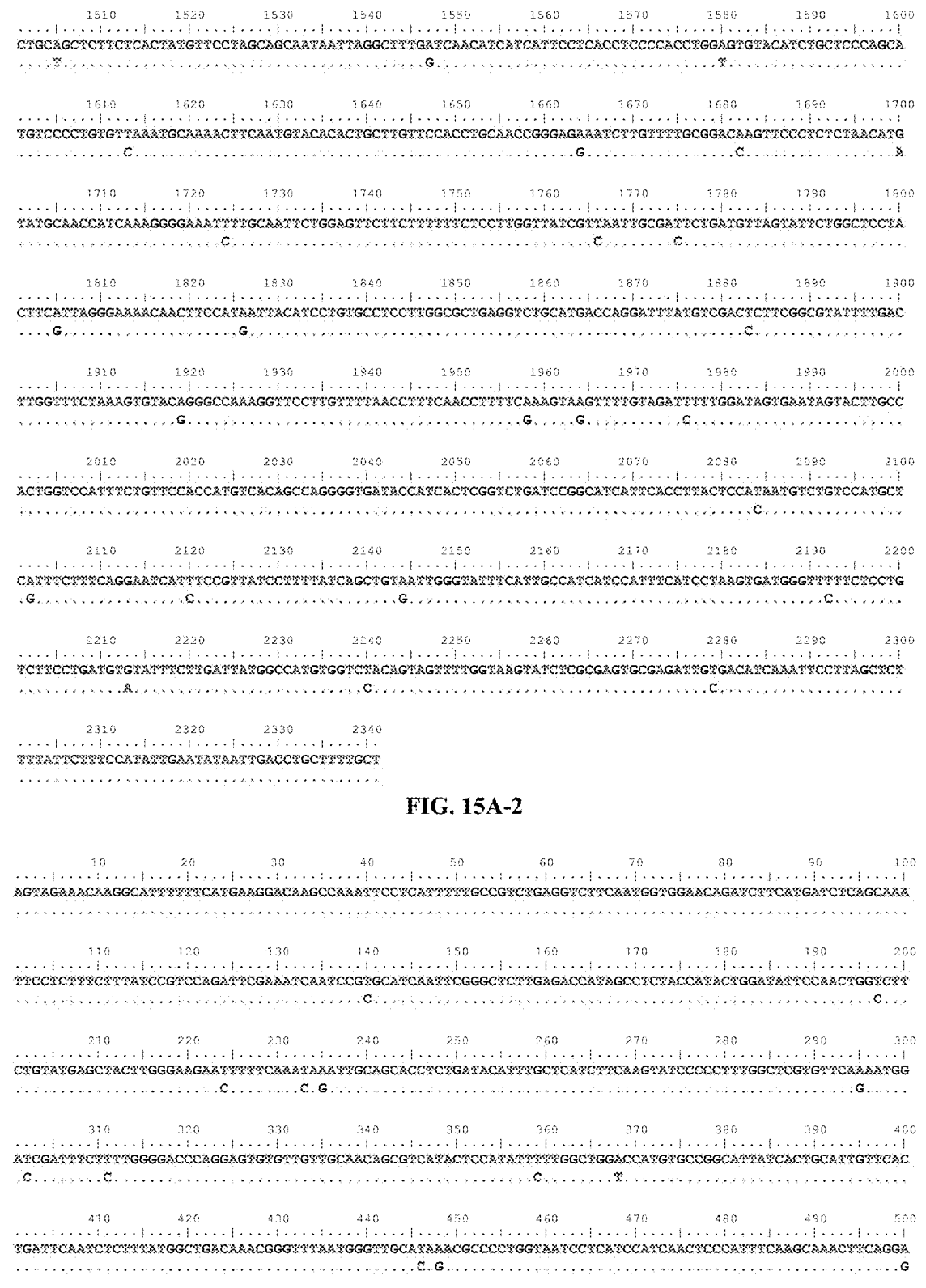
Figure 15B-2:
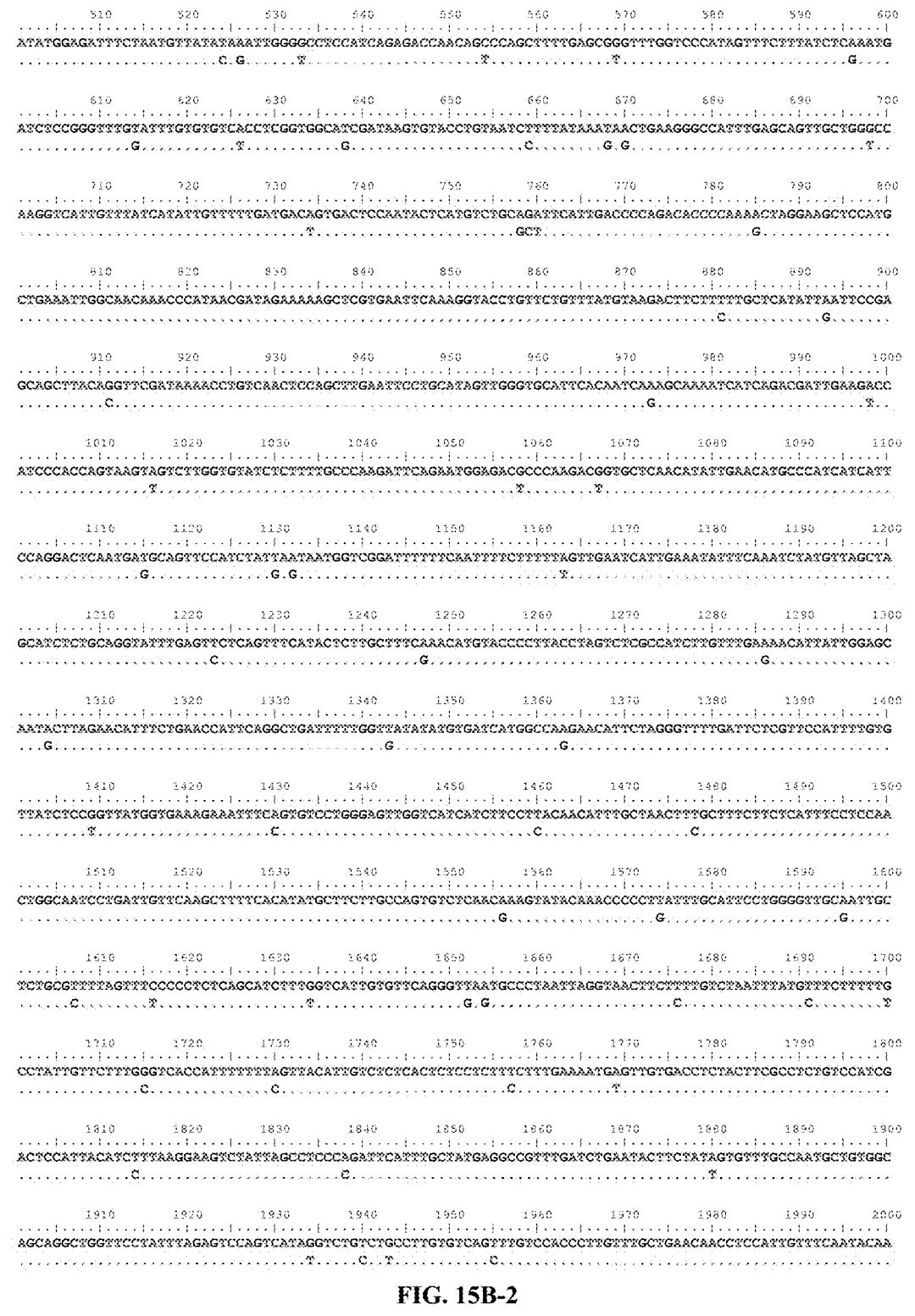
Figure 15C-2:
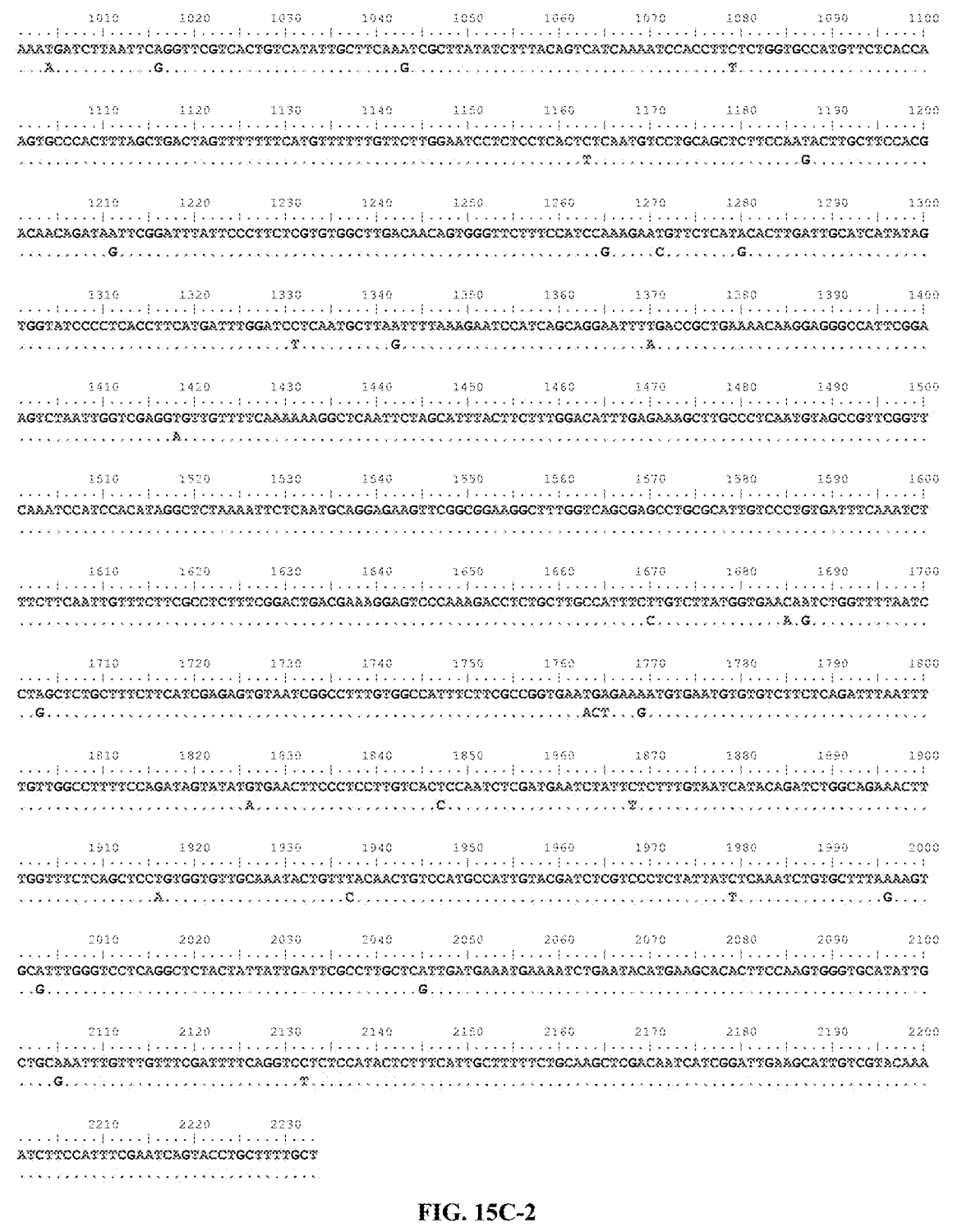
Figure 15D-1:
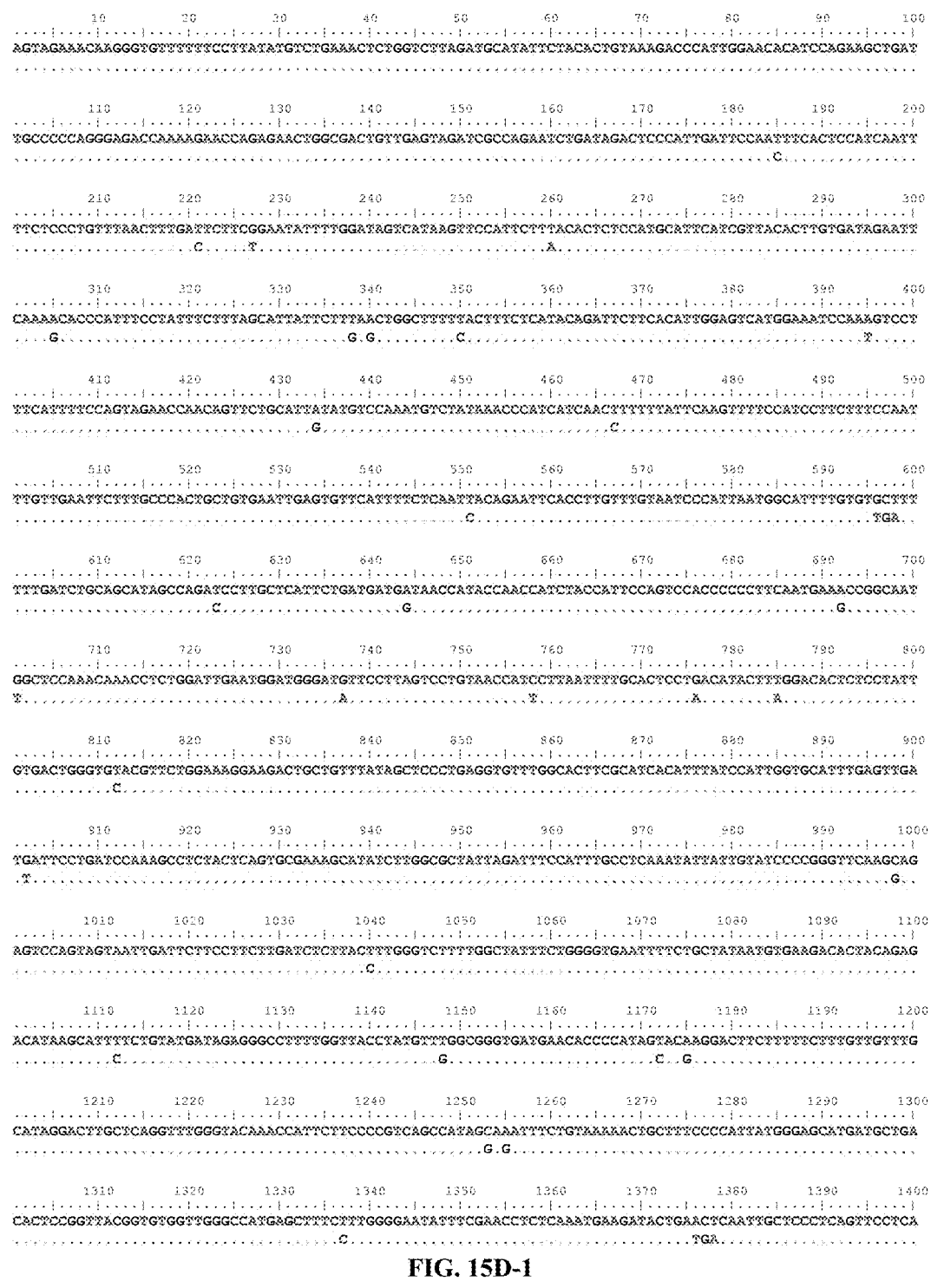
Figures 15D-2, 15E-1:
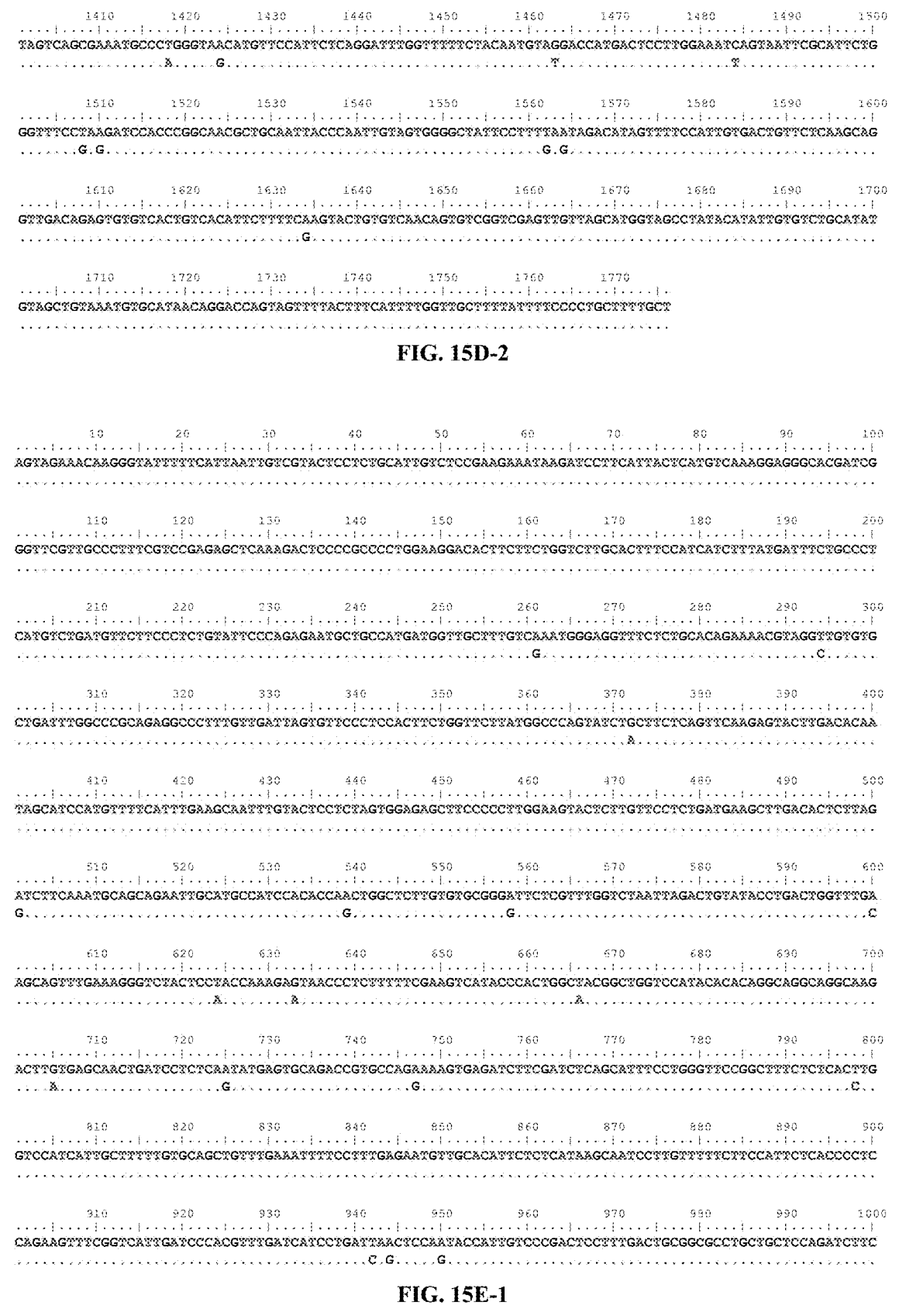
Figure 15F:
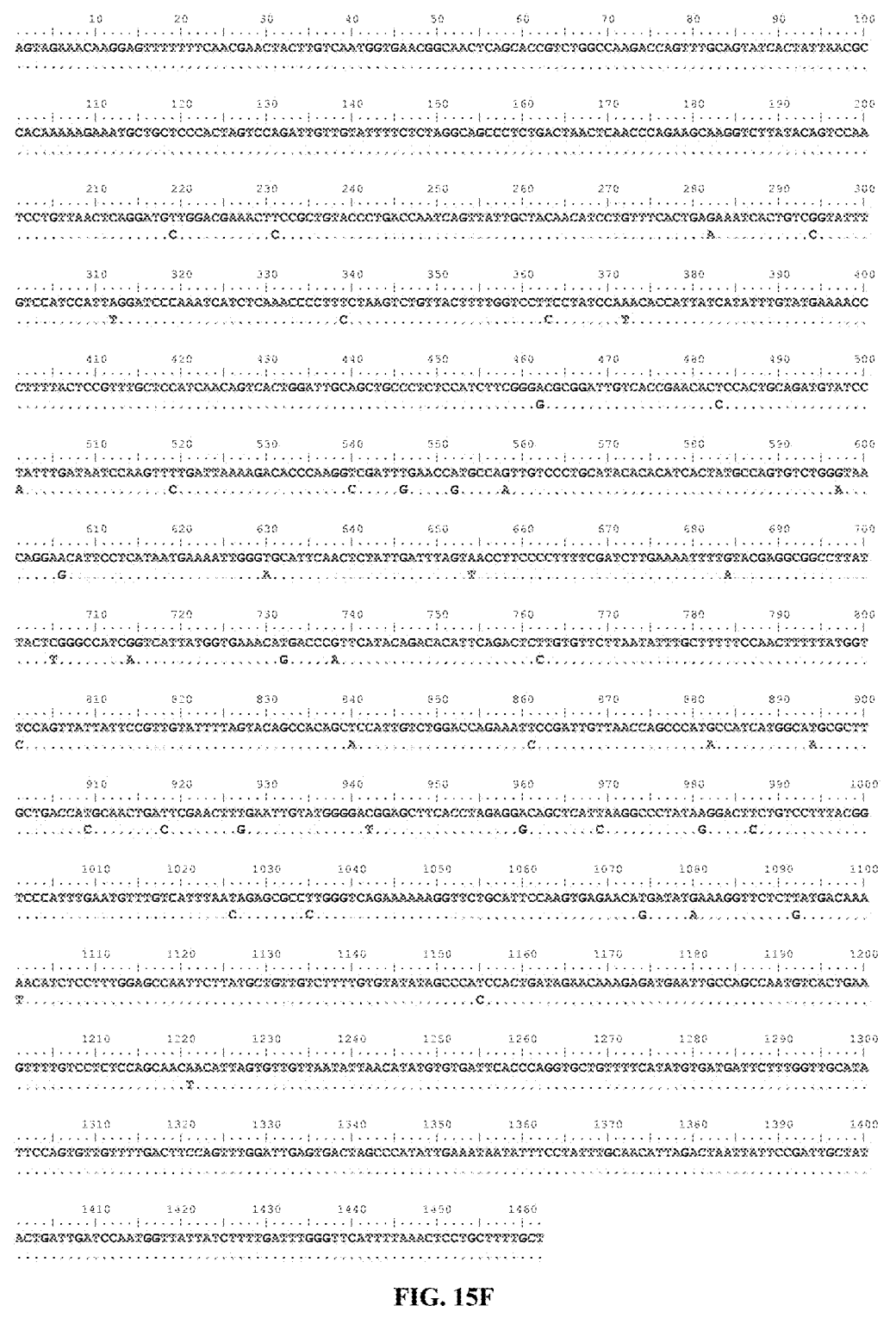

FIGS. 15A-1 to 15A-2, 15B-1 to 15B-3, 15C-1 to 15C-2, 15D-1 to 15D-2, 15E-1 to 15E-2, 15F, 15G, and 15H are diagrams of the alignment of wild-type and mutated viral RNA segments (represented, by convention, as DNA). In each case, the top sequence in each pair of sequence lines is the sequence of A/Brisbane/59/2007 virus and the bottom sequence in each pair of sequence lines is the mutated virus. For the mutated virus, only the mutated nucleotides are shown. All of the other nucleotides are the same as those in A/Brisbane/59/2007 virus. FIGS. 15A-1 and 15A-2 show the alignment of wild-type (SEQ ID NO:1) and mutated (SEQ ID NO:2) PB2 segments. FIGS. 15B-1, 15B-2 and 15B-3 show the alignment of wild-type (SEQ ID NO:3) and mutated (SEQ ID NO:4) PB1 segments. FIGS. 15C-1 and 15C-2 show the alignment of wild-type (SEQ ID NO:5) and mutated (SEQ ID NO:6) PA segments. FIGS. 15D-1 and 15D-2 show the alignment of wild-type (SEQ ID NO:7) and mutated (SEQ ID NO:8) HA segments. FIGS. 15E-1 and 15E-2 show the alignment of wild-type (SEQ ID NO:9) and mutated (SEQ ID NO:10) NP segments. FIG. 15F shows the alignment of wild-type (SEQ ID NO:11) and mutated (SEQ ID NO:12) NA segments. FIG. 15G shows the alignment of wild-type (SEQ ID NO:13) and mutated (SEQ ID NO:14) M segments. FIG. 15H shows the alignment of wild-type (SEQ ID NO:15) and mutated (SEQ ID NO:16) NS segments.

DETAILED DESCRIPTION OF THE INVENTION

The disclosed method and compositions may be understood more readily by reference to the following detailed description of particular forms and the Example included therein and to the Figures and their previous and following description.

As used herein, the term "robust immune response" refers to an antibody-mediated response, cell-mediated adaptive immune response, innate immune response, or a combination thereof, generated following administration of a virus, and generated at a level that provides immune protection to subsequent challenges with the same virus.

As used herein, the terms "immunologic response," "immunological response," or "immune response" refer to the development of a humoral (antibody mediated) response, a cellular (mediated by antigen-specific T cells or their secretion products) response, or both, directed against an antigen. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific CD4$^+$ T helper cells, CD8$^+$ cytotoxic T cells, or both. The response may also involve activation of monocytes, macrophages host, be packaged, infect the host again, or a combination thereof, is attenuated) is generally relative to one or more hosts of the virus, with the live-attenuated virus not significantly or detectably attenuated in one of more other hosts of the virus. The live-attenuated viruses disclosed herein are generally genetically altered and can be referred to as mutated, mutant, genetically engineered, recombinant, or a combination.

As used herein, the term "live-attenuated vaccine", or "live attenuated vaccine", or "attenuated vaccine" refers to a pharmaceutical composition containing a live-attenuated pathogen, such as a virus. The pharmaceutical composition contains at least one immunologically active component that induces an immune response in a subject against viruses, protects the subject from or possible death due to viruses, or both, and optionally can include one or more additional components that enhance the immunological activity of the active component. A vaccine can additionally include further components typical to pharmaceutical compositions. The at least one immunologically active component is one or more of the live-attenuated viruses described herein.

As used herein, the term "homologous viral challenge" refers to a second or subsequent viral challenge of the same subject, where the virus is substantially the same virus, viral subtype, strain, or infective viral particle, genetically as that used in the first viral challenge. In a homologous viral challenge—where the second or subsequent viral challenge of the same subject is with a virus of a substantially the same, or similar, viral subtype as the virus used in the first challenge—a homologous immune protection can be obtained.

As used herein, the term "heterologous viral challenge" refers to a second or subsequent viral challenge of the same subject, wherein the virus is a substantially different virus, viral subtype, strain, or infective viral particle, genetically as that used in the first viral challenge. In a heterologous viral challenge—where the second or subsequent viral challenge of the same subject is with a virus of a substantially different viral subtype from the virus used in the first challenge—a heterosubtypic immune protection can be obtained.

As used herein, the term "substantially the same genetically" refers to virus particles, in which the nucleic acid sequences of their genomes, or amino acid sequences produced by their genomes, show at least at least 98%, or at least 99% sequence homology as measured by nucleotide identity.

As used herein, the term "substantially different genetically" refers to virus particles, in which the nucleic acid sequences of their genomes, or amino acid sequences produced by their genomes, show less than at least 98% sequence homology as measured by nucleotide identity.

As used herein, the term "codon" refers to, as the context indicates, either (a) a sequence of three nucleotides that codes for a certain amino acid or signals the termination of translation (stop or termination codon) or (b) specific sequence of three consecutive nucleotides that is part of the genetic code and that specifies a particular amino acid in a protein or starts or stops protein synthesis—also called a triplet.

As used herein, the term "codon usage" refers to a frequency of use of each existing codon (triplet) coding an amino acid. There are 64 different codons (61 codons encoding for amino acids plus 3 stop codons) but only 20 different translated amino acids. The overabundance in the number of codons allows many amino acids to be encoded by more than one codon. Because of such redundancy it is said that the genetic code is degenerate. Different organisms often show particular preferences, or codon usage bias, for one of the several codons that encode the same amino acid—that is, a greater frequency of one will be found than expected by chance. Codon usage bias can be represented as a fraction, frequency, or percentage. For example, a codon usage of 1 indicates that the given codon is used 100% of the time to code for the given amino acid. Codon usage bias can also be represented by Relative Synonymous Codon Usage values (RSCU value, which is the observed number of codons divided by the number expected if all codons for that amino acid were used equally (Sharp et al., *Nucleic Acids Research*, 16:8207-8211 (1988), which is incorporated by reference herein for its descriptions and definitions of codon usage and codon usage bias). In the absence of any codon usage bias, the RSCU values would be 1.00. A codon that is used less frequently than expected will have an RSCU value of less than 1.00 and vice versa for a codon that is used more frequently than expected. Other methods of detecting codon usage bias include GC content, effective number of codons (ENC), Synonymous Codon Usage Order (SCUO), Codon Volatility, Codon Adaptation Index (CAI) and Odds Ratio (Fancher et al., AJMB 1:174-182 (2011), which is incorporated by reference herein for its descriptions and definitions of codon usage and codon usage bias).

The GC content measurement has been shown to correlate very strongly with the codon usage bias of a gene. The GC content provides a simple technique to verify other codon usage bias indices because of its strong correlation with the usage bias on the whole gene. The frequency of which a Guanine-'G' or a Cytosine-'C' nucleotide appears at the third position of the codons in a gene is the GC3 content. The GC content is usually found as in Equation (1), where G, C, A, and T represent the number of times that Guanine, Cytosine, Adenine and Thymine appear at a specific position in the codon. This gives the percentage of the GC content of the entire gene. The GC content can also be narrowed to just the third nucleotide position (GC3) by only counting the frequency of the bases at every third nucleotide.

$$GC \text{ content} = \frac{G+C}{A+C+T+G} \times 100 \quad \text{Equation (1)}$$

ENC measures the deviation of the codon usage in a gene from equal usage of synonymous codons. ENC estimates the absolute synonymous codon usage bias, which will range from 20, when only one codon is used per amino acid, to 61, when all synonymous codons are used with equal frequency. ENC is measured with the Equation (2):

$$ENC = 2 + \frac{9}{F2} + \frac{1}{F3} + \frac{5}{F4} + \frac{3}{F6} \quad \text{Equation (2)}$$

where F2 is the probability that two randomly chosen codons for an amino acid, possibly encoded by two distinct codons, are identical. Likewise, F3 is the probability that three randomly chosen codons for an amino acid with three synonymous codons are identical, and so forth. This yields an easy-to-understand representational value for the synonymous codon dispersion within a gene. However, ENC is still quite limiting in that it does not pro-vide specific details on codon usage frequency.

The RSCU of the jth codon for the ith amino acid is defined as (3), where $x_{ij}$ is the frequency of the jth codon for the ith amino acid and i is the number of alternative synonymous codons for the ith amino acid.

$$RSCU_{ij} = \frac{x_{ij}}{\frac{1}{n_i}\sum_{i=1}^{n_i} x_{ij}} \quad \text{Equation (3)}$$

To implement SCUO, a codon table, which contains all amino acids that have more than one codon, is created. This allows the referencing of the jth synonymous codon for the ith amino acid, where $1 \le i \le 19$ and $1 \le j \le n_i$ and where $n_i$ represents the number of synonymous codons for the ith amino acid. In each of these instances, $x_{ij}$ will represent the occurrence of the jth synonymous codon for amino acid i. The following sequence of equations describes the SCUO calculation.

First, the frequency of the ith degenerate codon of amino acid i is found by normalizing $x_{ij}$ as follows:

$$p_{ij} = \frac{x_{ij}}{\sum_{j=1}^{n_i} x_{ij}} \quad \text{Equation (4)}$$

The entropy of the ith amino acid is calculated next with Equation (5), where $n_i$ represents the number of synonymous codons for the jth amino acid. The maximum entropy will occur when every codon is used with equal frequency.

$$H_i = -\sum_{j=1}^{n_i} p_{ij} \log \log p_{ij} \quad \text{Equation (5)}$$

Next, the normalized difference between the maximum entropy and the observed entropy for the jth amino acid in each sequence is calculated. This value, Oi (Equation (6)), will be the SCUO for the jth amino acid in each sequence.

$$O_i = \frac{H_i^{max} - H_i}{H_i^{max}} \quad \text{Equation (6)}$$

The composition ratio of the jth amino acid in each sequence is calculated as Fi, (Equation (7)), where the sum is taken from 1 to 18 to account for the amino acids that are encoded by more than one codon.

$$F_i = \frac{\sum_{j=1}^{n_i} x_{ij}}{\sum_i^{18} \sum_{j=1}^{n_i} x_{ij}} \quad \text{Equation (7)}$$

Finally, the average SCUO for each sequence is represented as in Equation (8).

$$O = \sum_{i=1}^{i-1} F_i O_i \quad \text{Equation (8)}$$

The volatility of a codon (with a Hamming distance metric), $V_H(c)$, quantifies the degree to which a random nucleotide mutation will cause an amino acid substitution. Assuming that all nucleotides will have an equal rate of mutation and are equally exchangeable, the volatility of a codon is the ratio of point-mutational neighbors to total possible single point mutations. For example, TTG in the amino acid Leu will have a volatility of 6/8, since 6 of its 8 non-stop codon neighbors are non-synonymous In codon volatility, the volatility of a codon is the probability that a random point mutation will result in a nonsynonymous codon (a codon that does not encode the same amino acid). The volatility of a codon is calculated with Equation (9).

$$V_{(c)} = \sum_{i=1}^{9} d[\text{acid}(c_i), \text{acid}(c)] \quad \text{Equation (9)}$$

where $d(x,y)$ is the Hamming distance between codons x and y. The Hamming distance is defined as $d(\text{acid}(c_i), \text{acid}(c)) = 0$ if $\text{acid}(c_i)$ encodes the same amino acid as $\text{acid}(c)$ otherwise, if it encodes a different amino acid, it is defined as 1 and a substitution occurs.

The Odds Ratio calculation is commonly used to evaluate dinucleotides, pairs of nucleotides, in gene sequences. Odds Ratio is a likelihood of observing a dinucleotide in a sequence and is calculated as in (10).

$$P_{xy} = \frac{f_{xy}}{f_x f_y} \quad \text{Equation (10)}$$

where x and y represent the nucleotides that form dinucleotide xy; and $f_x$, $f_y$, $f_{xy}$ denote the frequencies of nucleotide x, nucleotide y, and dinucleotide xy respectively. It was shown that that dinucleotides with an odds ratio that is outside of the range [0.78,1.25] could be considered as being more under- or over-represented than normal (Karlin et al., J Virol., 68:2889-2897 (1994); Fancher et al., ABM 1:174-182 (2011)).

Codon usage can be calculated for any portion, portions, or an entire, nucleic acid molecule, or collection of nucleic acid molecules, that include one or more coding regions. For example, codon usage can be calculated for a segment, region, exon, etc. of a nucleic acid molecule, a gene, a domain, a chromosome, a genome or a species, genus, family, order, class, phylum, or kingdom of organism.

Table 1 below shows the codon usage frequencies of avian influenza viruses and of A/Brisbane/59/2007 virus. The numbers for each codon shows the number of codons of that sequence in each of the eight influenza virus segments. These data exemplify how the codon usage of human and avian influenza viruses was compared to derive the mutated codons described herein.

TABLE 1

Codon usage frequencies of avian influenza viruses and of A/Brisbane/59/2007 virus (BR59).

| | | PB2 | | PB1 | | PA | | HA | |
|---|---|---|---|---|---|---|---|---|---|
| | | Avian | BR59 | Avian | BR59 | Avian | BR59 | Avian | BR59 |
| Phe | UUU | 9.3 | 13 | 12.9 | 18.0 | 15.3 | 20.0 | 8.1 | 8.0 |
| | UUC | 14.7 | 11 | 20.1 | 15.0 | 20.8 | 18.0 | 12.7 | 12.0 |
| Leu | UUA | 6.5 | 13 | 6.2 | 13.0 | 4.3 | 6.0 | 4.7 | 8.0 |
| | UUG | 14.8 | 11 | 9.1 | 12.0 | 9.4 | 13.0 | 10.0 | 11.0 |
| Tyr | UAU | 8.2 | 4 | 11.1 | 13.0 | 11.1 | 12.0 | 15.8 | 18.0 |
| | UAC | 7.9 | 12 | 13.8 | 13.0 | 7.9 | 8.0 | 10.2 | 8.0 |

TABLE 1-continued

Codon usage frequencies of avian influenza viruses and of A/Brisbane/59/2007 virus (BR59).

| | | | | | | | | | |
|---|---|---|---|---|---|---|---|---|---|
| ter | UAA | 0.0 | 1 | 0.0 | 0.0 | 0.0 | 0.0 | 0.1 | 1.0 |
| ter | UAG | 1.0 | 0 | 0.9 | 0.0 | 1.0 | 1.0 | 0.9 | 0.0 |
| Leu | CUU | 8.4 | 10 | 10.4 | 11.0 | 15.8 | 14.0 | 3.7 | 6.0 |
| | CUC | 9.2 | 9 | 8.8 | 4.0 | 10.3 | 9.0 | 8.3 | 1.0 |
| | CUA | 10.4 | 12 | 10.3 | 9.0 | 8.4 | 6.0 | 10.7 | 9.0 |
| | CUG | 11.7 | 7 | 13.3 | 7.0 | 13.8 | 13.0 | 13.2 | 15.0 |
| His | CAU | 6.2 | 7 | 5.5 | 7.0 | 5.8 | 4.0 | 7.2 | 9.0 |
| | CAC | 3.8 | 3 | 4.5 | 3.0 | 7.3 | 9.0 | 5.7 | 6.0 |
| Gln | CAA | 20.4 | 20 | 20.6 | 21.0 | 10.5 | 13.0 | 11.0 | 10.0 |
| | CAG | 15.7 | 15 | 10.3 | 9.0 | 7.6 | 9.0 | 6.9 | 6.0 |
| Ile | AUU | 15.7 | 20 | 16.0 | 19.0 | 22.0 | 27.0 | 10.9 | 11.0 |
| | AUC | 13.2 | 8 | 12.0 | 6.0 | 10.9 | 8.0 | 5.5 | 8.0 |
| | AUA | 21.2 | 20 | 17.6 | 22.0 | 16.0 | 16.0 | 13.2 | 14.0 |
| Met | AUG | 34.7 | 35 | 36.7 | 35.0 | 25.1 | 25.0 | 8.2 | 9.0 |
| Asn | AAU | 19.3 | 27 | 25.9 | 27.0 | 12.8 | 22.0 | 27.4 | 27.0 |
| | AAC | 11.9 | 8 | 22.6 | 22.0 | 18.3 | 11.0 | 17.0 | 21.0 |
| Lys | AAA | 26.0 | 32 | 23.2 | 33.0 | 32.1 | 31.0 | 16.6 | 25.0 |
| | AAG | 18.4 | 13 | 28.1 | 18.0 | 21.3 | 19.0 | 16.9 | 13.0 |
| Val | GUU | 13.1 | 15 | 9.6 | 11.0 | 5.4 | 6.0 | 8.7 | 7.0 |
| | GUC | 9.8 | 10 | 9.8 | 12.0 | 4.9 | 3.0 | 8.0 | 9.0 |
| | GUA | 15.7 | 18 | 5.9 | 8.0 | 5.9 | 11.0 | 6.4 | 13.0 |
| | GUG | 23.5 | 22 | 10.5 | 8.0 | 13.4 | 10.0 | 11.6 | 6.0 |
| Asp | GAU | 15.8 | 19 | 18.0 | 20.0 | 23.2 | 24.0 | 11.9 | 11.0 |
| | GAC | 18.0 | 12 | 14.0 | 16.0 | 13.7 | 12.0 | 11.9 | 7.0 |
| Glu | GAA | 28.7 | 34 | 28.1 | 27.0 | 47.1 | 35.0 | 22.1 | 27.0 |
| | GAG | 24.1 | 18 | 21.6 | 18.0 | 30.4 | 44.0 | 14.6 | 13.0 |
| Ser | UCU | 7.2 | 9 | 6.9 | 9.0 | 11.1 | 7.0 | 7.3 | 8.0 |
| | UCC | 4.5 | 3 | 7.0 | 7.0 | 9.6 | 11.0 | 8.0 | 10.0 |
| | UCA | 14.7 | 18 | 11.6 | 11.0 | 8.2 | 14.0 | 16.5 | 12.0 |
| | UCG | 3.7 | 2 | 3.4 | 2.0 | 3.6 | 1.0 | 1.6 | 1.0 |
| Cys | UGU | 1.1 | 0 | 5.3 | 5.0 | 4.1 | 5.0 | 6.7 | 9.0 |
| | UGC | 3.9 | 5 | 4.7 | 5.0 | 11.9 | 11.0 | 9.3 | 7.0 |
| ter | UGA | 0.0 | 0 | 0.1 | 1.0 | 0.0 | 0.0 | 0.0 | 0.0 |
| Trp | UGG | 10.0 | 10 | 9.0 | 9.0 | 12.0 | 12.0 | 11.0 | 10.0 |
| Pro | CCU | 7.8 | 10 | 9.5 | 10.0 | 5.9 | 7.0 | 5.1 | 3.0 |
| | CCC | 6.0 | 4 | 4.4 | 4.0 | 5.8 | 5.0 | 5.0 | 4.0 |
| | CCA | 12.8 | 14 | 12.6 | 13.0 | 13.8 | 13.0 | 6.8 | 13.0 |
| | CCG | 2.4 | 1 | 5.5 | 5.0 | 6.7 | 7.0 | 1.3 | 1.0 |
| Arg | CGU | 1.1 | 1 | 1.4 | 2.0 | 1.8 | 3.0 | 0.1 | 0.0 |
| | CGC | 3.8 | 4 | 2.6 | 2.0 | 2.2 | 1.0 | 0.1 | 0.0 |
| | CGA | 3.9 | 3 | 3.7 | 6.0 | 4.8 | 3.0 | 1.8 | 0.0 |
| | CGG | 6.2 | 4 | 4.5 | 4.0 | 3.7 | 1.0 | 1.0 | 0.0 |
| Thr | ACU | 12.3 | 17 | 8.7 | 16.0 | 7.6 | 6.0 | 12.4 | 6.0 |
| | ACC | 9.5 | 9 | 10.8 | 18.0 | 10.8 | 10.0 | 7.0 | 4.0 |
| | ACA | 26.3 | 24 | 34.6 | 22.0 | 17.2 | 21.0 | 17.4 | 18.0 |
| | ACG | 4.7 | 4 | 5.7 | 2.0 | 1.5 | 0.0 | 2.1 | 1.0 |
| Ser | AGU | 9.4 | 9 | 7.1 | 9.0 | 7.8 | 6.0 | 7.2 | 8.0 |
| | AGC | 12.7 | 12 | 14.2 | 11.0 | 10.0 | 10.0 | 7.4 | 9.0 |
| Arg | AGA | 28.4 | 31 | 21.4 | 25.0 | 16.4 | 22.0 | 10.7 | 10.0 |
| | AGG | 16.9 | 17 | 16.9 | 13.0 | 12.9 | 14.0 | 5.3 | 8.0 |
| Ala | GCU | 11.8 | 13 | 12.8 | 13.0 | 6.1 | 12.0 | 8.0 | 8.0 |
| | GCC | 8.3 | 7 | 8.4 | 7.0 | 9.6 | 5.0 | 6.7 | 8.0 |
| | GCA | 21.6 | 18 | 17.8 | 22.0 | 19.7 | 19.0 | 14.1 | 11.0 |
| | GCG | 3.5 | 4 | 2.7 | 1.0 | 3.6 | 0.0 | 3.3 | 3.0 |
| Gly | GGU | 6.2 | 7 | 3.5 | 8.0 | 4.0 | 4.0 | 4.7 | 8.0 |
| | GGC | 8.5 | 8 | 4.2 | 9.0 | 8.2 | 8.0 | 5.5 | 4.0 |
| | GGA | 21.9 | 21 | 29.1 | 18.0 | 13.8 | 16.0 | 17.4 | 19.0 |
| | GGG | 11.4 | 12 | 9.2 | 12.0 | 10.0 | 7.0 | 15.2 | 12.0 |

| | | NP | | NA | | M1 | | NS1 | |
|---|---|---|---|---|---|---|---|---|---|
| | | Avian | BR59 | Avian | BR59 | Avian | BR59 | Avian | BR59 |
| Phe | UUU | 6.2 | 8.0 | 10.5 | 8.0 | 4.0 | 4.0 | 3.9 | 3.0 |
| | UUC | 11.9 | 9.0 | 7.3 | 9.0 | 2.8 | 3.0 | 4.6 | 7.0 |
| Leu | UUA | 0.4 | 2.0 | 4.6 | 6.0 | 1.0 | 3.0 | 1.5 | 1.0 |
| | UUG | 2.7 | 7.0 | 8.2 | 7.0 | 1.6 | 0.0 | 1.1 | 2.0 |
| Tyr | UAU | 8.0 | 7.0 | 8.1 | 6.0 | 0.7 | 3.0 | 0.5 | 0.0 |
| | UAC | 5.8 | 8.0 | 4.5 | 8.0 | 4.3 | 2.0 | 1.2 | 1.0 |
| ter | UAA | 0.9 | 1.0 | 0.1 | 1.0 | 0.0 | 0.0 | 0.0 | 0.0 |
| ter | UAG | 0.0 | 0.0 | 0.8 | 1.0 | 0.0 | 0.0 | 0.1 | 0.0 |
| Leu | CUU | 5.1 | 6.0 | 1.7 | 2.0 | 5.9 | 9.0 | 7.4 | 7.0 |
| | CUC | 10.4 | 10.0 | 0.3 | 0.0 | 6.5 | 7.0 | 4.7 | 3.0 |
| | CUA | 2.7 | 3.0 | 1.3 | 4.0 | 5.1 | 2.0 | 4.4 | 5.0 |
| | CUG | 10.5 | 5.0 | 3.1 | 2.0 | 5.9 | 5.0 | 4.1 | 4.0 |
| His | CAU | 4.4 | 2.0 | 4.7 | 5.0 | 3.6 | 4.0 | 2.0 | 2.0 |
| | CAC | 1.7 | 3.0 | 4.3 | 3.0 | 1.4 | 1.0 | 0.2 | 1.0 |

TABLE 1-continued

Codon usage frequencies of avian influenza viruses and of A/Brisbane/59/2007 virus (BR59).

| | | | | | | | | | |
|---|---|---|---|---|---|---|---|---|---|
| Gln | CAA | 11.0 | 13.0 | 7.2 | 11.0 | 2.8 | 5.0 | 1.8 | 4.0 |
| | CAG | 10.9 | 8.0 | 5.2 | 1.0 | 12.1 | 10.0 | 5.7 | 5.0 |
| Ile | AUU | 8.9 | 9.0 | 11.3 | 11.0 | 3.3 | 3.0 | 6.1 | 5.0 |
| | AUC | 13.8 | 13.0 | 10.4 | 10.0 | 4.5 | 4.0 | 5.2 | 3.0 |
| | AUA | 6.5 | 6.0 | 15.4 | 22.0 | 2.0 | 5.0 | 4.7 | 3.0 |
| Met | AUG | 23.6 | 21.0 | 7.9 | 8.0 | 14.1 | 14.0 | 9.4 | 10.0 |
| Asn | AAU | 15.7 | 17.0 | 23.3 | 22.0 | 5.0 | 9.0 | 4.0 | 6.0 |
| | AAC | 11.1 | 10.0 | 7.6 | 15.0 | 5.6 | 2.0 | 3.6 | 3.0 |
| Lys | AAA | 8.9 | 14.0 | 11.1 | 13.0 | 5.6 | 5.0 | 8.1 | 8.0 |
| | AAG | 6.3 | 8.0 | 7.8 | 10.0 | 6.9 | 8.0 | 4.3 | 5.0 |
| Val | GUU | 4.8 | 1.0 | 7.5 | 11.0 | 3.0 | 3.0 | 2.2 | 5.0 |
| | GUC | 4.2 | 6.0 | 4.0 | 4.0 | 4.1 | 3.0 | 4.0 | 5.0 |
| | GUA | 4.1 | 8.0 | 9.8 | 5.0 | 1.6 | 2.0 | 1.6 | 2.0 |
| | GUG | 10.1 | 10.0 | 8.1 | 8.0 | 7.4 | 5.0 | 4.4 | 3.0 |
| Asp | GAU | 8.0 | 12.0 | 10.3 | 12.0 | 5.3 | 4.0 | 10.0 | 10.0 |
| | GAC | 13.0 | 11.0 | 10.4 | 12.0 | 1.5 | 2.0 | 7.1 | 5.0 |
| Glu | GAA | 22.1 | 19.0 | 9.1 | 10.0 | 7.2 | 7.0 | 10.6 | 10.0 |
| | GAG | 14.8 | 16.0 | 10.7 | 9.0 | 9.7 | 10.0 | 7.0 | 6.0 |
| Ser | UCU | 11.3 | 13.0 | 8.5 | 8.0 | 2.0 | 4.0 | 3.5 | 3.0 |
| | UCC | 5.8 | 5.0 | 7.1 | 3.0 | 1.4 | 1.0 | 2.8 | 3.0 |
| | UCA | 5.2 | 6.0 | 12.4 | 16.0 | 4.0 | 3.0 | 4.7 | 4.0 |
| | UCG | 1.7 | 1.0 | 1.3 | 1.0 | 0.4 | 1.0 | 0.2 | 1.0 |
| Cys | UGU | 1.6 | 1.0 | 8.9 | 11.0 | 1.9 | 3.0 | 0.6 | 2.0 |
| | UGC | 4.4 | 5.0 | 9.5 | 7.0 | 1.2 | 0.0 | 1.5 | 1.0 |
| ter | UGA | 0.1 | 0.0 | 0.0 | 0.0 | 1.0 | 1.0 | 0.8 | 1.0 |
| Trp | UGG | 6.0 | 6.0 | 15.3 | 16.0 | 1.0 | 1.0 | 4.0 | 4.0 |
| Pro | CCU | 5.2 | 5.0 | 6.3 | 8.0 | 1.9 | 2.0 | 3.2 | 3.0 |
| | CCC | 3.3 | 5.0 | 3.7 | 2.0 | 2.1 | 2.0 | 1.3 | 2.0 |
| | CCA | 5.0 | 6.0 | 10.9 | 6.0 | 3.1 | 3.0 | 4.8 | 3.0 |
| | CCG | 2.5 | 1.0 | 1.8 | 4.0 | 0.9 | 1.0 | 0.5 | 0.0 |
| Arg | CGU | 2.8 | 1.0 | 0.0 | 1.0 | 1.1 | 1.0 | 0.8 | 0.0 |
| | CGC | 1.3 | 3.0 | 1.1 | 0.0 | 0.7 | 1.0 | 2.6 | 2.0 |
| | CGA | 3.7 | 2.0 | 0.3 | 1.0 | 2.4 | 4.0 | 3.1 | 2.0 |
| | CGG | 4.9 | 6.0 | 1.2 | 0.0 | 1.8 | 0.0 | 2.8 | 4.0 |
| Thr | ACU | 11.0 | 10.0 | 12.3 | 11.0 | 5.3 | 4.0 | 6.5 | 10.0 |
| | ACC | 5.8 | 6.0 | 5.8 | 11.0 | 5.9 | 7.0 | 1.3 | 2.0 |
| | ACA | 8.8 | 10.0 | 8.8 | 10.0 | 5.1 | 5.0 | 4.4 | 6.0 |
| | ACG | 2.0 | 3.0 | 1.1 | 0.0 | 3.2 | 2.0 | 0.5 | 0.0 |
| Ser | AGU | 8.1 | 7.0 | 14.7 | 14.0 | 6.1 | 5.0 | 1.8 | 2.0 |
| | AGC | 6.3 | 7.0 | 10.1 | 8.0 | 2.4 | 4.0 | 3.1 | 3.0 |
| Arg | AGA | 29.3 | 24.0 | 8.8 | 11.0 | 6.5 | 7.0 | 7.8 | 4.0 |
| | AGG | 12.9 | 12.0 | 5.5 | 3.0 | 5.0 | 4.0 | 1.7 | 4.0 |
| Ala | GCU | 10.4 | 10.0 | 10.4 | 9.0 | 7.4 | 9.0 | 4.4 | 6.0 |
| | GCC | 4.7 | 7.0 | 2.4 | 3.0 | 7.5 | 10.0 | 1.9 | 2.0 |
| | GCA | 20.2 | 20.0 | 5.0 | 8.0 | 8.2 | 8.0 | 6.0 | 6.0 |
| | GCG | 3.9 | 3.0 | 1.0 | 0.0 | 2.5 | 0.0 | 1.8 | 2.0 |
| Gly | GGU | 4.5 | 6.0 | 9.0 | 6.0 | 2.8 | 2.0 | 2.7 | 1.0 |
| | GGC | 3.7 | 3.0 | 8.0 | 9.0 | 2.4 | 2.0 | 2.0 | 4.0 |
| | GGA | 21.2 | 22.0 | 13.5 | 21.0 | 5.6 | 5.0 | 6.6 | 7.0 |
| | GGG | 12.4 | 10.0 | 13.8 | 8.0 | 5.4 | 7.0 | 2.2 | 3.0 |

Avian viral codon usage bias can refer to the ratio of the synonymous codons for a given amino acid in a gene, segment, or entire coding sequence of avian viruses of the same type as the wild type virus or of a single or set of reference avian viruses.

As used herein, the term "randomly and evenly distributed" refers, in a context of mutated codons, to a distribution of the mutated codons in the genome (or gene, or exon, or segment, etc.) so that one mutated codon can be positioned next to, or at least one codon away from, another mutated codon. In other words, the mutated codons are positioned without precalculated distances from one another, and are present throughout the genome (or gene, or exon, or segment, etc.), i.e., are not clustered in one gene, segment, or region. "Randomly and evenly distributed" does not require exact or statistically random or even distribution, just a lack of clustering. When the same codon mutation is introduced more than one time in a segment, the mutations are evenly distributed across the whole segment.

As used herein, the term "replication" refers to genome replication. When referring to viruses, the term "replication" also means "viral replication," which encompasses the processes of replication of the viral genome, production of viral proteins, packaging of the viral genome, and formation of a new viral particle.

As used herein, the terms "unaltered replication," "substantially the same replication," and "similar replication," in the context of virus, refer to the replication of a virus that is comparable to or substantially the same as the replication of a reference virus of the same species. For example, when replication of a live-attenuated virus is comparable to or substantially the same as the replication of the replication of the wild type virus of the live-attenuated virus, such replication can be referred to as unaltered or similar replication. The replication can be measured by any technique used to measure viral replication in the art, such as by viral yield or by the rate of viral replication or production. For example, the replication can be measured by the number of plaque forming units, by the number of virions, by the number of viral particles, etc., per se, or per unit time, or per unit weight of an organ, or per unit weight of protein or nucleic acid, or per unit length of nucleic acid. For example, "substantially the same replication rate" refers to a change in the number of viral particles per unit weight of tissue, wherein the change in the number for one virus is substantially the same as the change in the number for another virus. As used herein, the term "substantially the same" refers to the same, or similar value, e.g., a value for replication, or a value for the change in the number of viruses. The values can be identical or can differ from each other within a range of ±10%, when compared to each other.

As used herein, the terms "slow replication" and "attenuated replication" in the context of virus, refer to the replication of a virus that is slower or less than the replication of a reference virus of the same species. For example, when replication of a live-attenuated virus is slower or less than the replication of the replication of the wild type virus of the live-attenuated virus, such replication can be referred to as slow or attenuated replication. The replication can be measured by any techniques used to measure viral replication in the art, such as by viral yield or by the rate of viral replication or production. For example, the reduction in replication can be any reduction in the number of plaque forming units, in the number of virions, in the number of viral particles, etc. The reduction can range from, for example, 10% to 90% relative to the number plaque forming units, the number of virions, or the number of viral particles of the wild type virus.

As used herein, the terms "master strain" and "master virus" refer to a viral subtype or strain that can be allowed to recombine with another virulent subtype or strain of a virus to produce a hybrid virus.

As used herein, the term "synonymous substitution" refers to a change of a nucleotide in a genome of an organism that is in a coding region but that do not result in a change to the encoded amino acid sequence.

As used herein, the term "silent mutation" refers to a change of a nucleotide in a genome of an organism that does not significantly alter the phenotype of the organism. Silent mutations can occur in non-coding regions (outside of genes within introns), or they can occur within exons. When they occur within exons or coding regions they either do not result in a change to the encoded amino acid sequence (i.e. a synonymous substitution), or result in the insertion of an alternative amino acid with similar properties to that of the original amino acid, and in either case there is no significant change in phenotype.

As used herein, the term "mammalian host" refers, in the context of a virus, to any mammalian organism that is capable of being infected with and propagating the virus.

As used herein, the term "avian host" refers, in the context of a virus, to any avian organism that is capable of being infected with and propagating the virus.

As used herein, the term "8-mut" refers to a virus with a segmented genome, in which 8 of its segments are mutated relative to the wild type virus. As used herein, the term "segmented genome" refers to a genome that is divided into separate nucleic acid regions or segments.

As used herein, the term "nucleic acid region" or "genomic region" refers to any region of the genome. The region can be a segment of a genome, a stretch of two or more nucleotides, or the entire genome.

As used herein, the term “involving packaging or splicing” refers, in the context of a virus, to a genomic region that encodes proteins responsible for packaging or splicing the genomic material, or a genomic region that has a nucleic acid sequence that defines sites of packaging or splicing, such as splice donor site and splice acceptor site.

The term “nucleic acid molecule” as used herein refers to any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA) and tecto-RNA molecules (e.g. Liu, B., et al., *J. Am. Chem. Soc.,* 126:4076-4077 (2004)). A PNA molecule is a nucleic acid molecule in which the backbone is a pseudopeptide rather than a sugar. Accordingly, PNA generally has a charge neutral backbone, in contrast to for example DNA or RNA. Nevertheless, PNA is capable of hybridising at least complementary and substantially complementary nucleic acid strands, just as e.g. DNA or RNA (to which PNA is considered a structural mimic). An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA can be of genomic or synthetic origin and can be single or double stranded. Such nucleic acid can be e.g. mRNA, cRNA, vRNA, synthetic RNA, genomic DNA, cDNA synthetic DNA, a copolymer of DNA and RNA, oligonucleotides, mixed polymers, both sense and antisense strands, or can contain non-natural or derivatized nucleotide bases. A respective nucleic acid can be a nucleic acid containing non-natural nucleotide analogues, a nucleic acid linked to an affinity tag or a label, or both. When referred to herein, the terms “nucleotide sequence(s),” “polynucleotide(s),” “nucleic acid sequence(s),” “nucleic acid(s),” and “nucleic acid molecule” are used interchangeably.

As used herein, the term “wild type virus” refers to a virus in its native form, as it occurs in nature, in its hosts, prior to genetic or other kinds of deliberate manipulations by man.

As used herein, the term “parent virus” refers to a virus prior to initial or further genetic or other kinds of deliberate manipulations by man.

As used herein, the terms “genetically engineered” and “genetically modified” refer to genetic manipulation of an organism, at a nucleotide, codon, gene, segment, frame, or chromosome level using biotechnology. A new nucleotide, base, base pair, or DNA can be inserted in the host genome by first isolating and copying the genetic material of interest using molecular cloning methods to generate a DNA sequence, or by synthesizing the DNA, and then inserting this construct into the host organism. A nucleotide, codon, gene, segment, frame, or chromosome can be removed (“knocked out,” added (“knocked in”), or replaced. Genetically engineered organisms can also be referred to as mutated organisms, mutant organisms, recombinant organisms, or a combination. Generally, all of these terms will apply interchangeably to genetically engineered organisms.

As used herein, the term “conserved sites at the amino acid level” refers to sites in a genome of an organism that use the same amino acid at the site more than 90% of the time among different strains of the same organism or among different species of the same genus. As used herein, the term “semi-conserved sites at the amino acid level” refers to sites in a genome of an organism that use the same amino acid at the site more than 80% of the time among different strains of the same organism or among different species of the same genus.

As used herein, the term "host cell" refers to prokaryotic and eukaryotic cells into which the genetic material of a virus, or a recombinant expression vector, can be introduced.

As used herein, the terms "transformed" and "transfected" refer to the introduction of a nucleic acid (e.g. a vector) into a cell by a number of techniques known in the art.

As used herein, the term "immune cell" refers to a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

The term 'T cell" refers to a CD4+ T cell or a CD8+ T cell. The term T cell includes TH1 cells, TH2 cells and TH17 cells.

The term "T cell cytotoxicity" includes any immune response that is mediated by CD8+ T cell activation. Exemplary immune responses include cytokine production, CD8+ T cell proliferation, granzyme or perforin production, and clearance of an infectious agent.

As generally used herein "pharmaceutically acceptable" refers to those compounds, materials, compositions, dosage forms, or a combination thereof, which are, within the scope of sound medical judgment, suitable for use in contact with the tissues, organs, bodily fluids, or a combination thereof, of human beings and animals without excessive toxicity, irritation, allergic response, or other problems or complications commensurate with a reasonable benefit/risk ratio.

The terms "individual, "subject," and "patient" refer to any individual who is the target of treatment using the disclosed compositions. The subject can be a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "polypeptide" refers to a chain of amino acids of any length, regardless of modification (e.g., phosphorylation or glycosylation).

As used herein, the terms "effective amount" and "therapeutically effective amount" refer to a dosage sufficient to provide treatment for a disorder, disease, or condition being treated, to induce or enhance an immune response, or to otherwise provide a desired pharmacologic effect, physiologic effect, or both. The precise dosage will vary according to a variety of factors such as subject-dependent variables (e.g., age, immune system health, etc.), the disease, the disease stage, and the treatment being effected. As used herein, the term "carrier" or "excipient" refers to an organic or inorganic ingredient, natural or synthetic inactive ingredient in a formulation, with which one or more active ingredients are combined.

As used herein, the term "adjuvant" refers to an agent, a pharmacological, an immunological agent, or a combination thereof, that modifies the effect of other agents. Adjuvants can be added to vaccine to modify the immune response by boosting it such as to give a higher amount of antibodies and a longer-lasting protection, thus minimizing the amount of injected foreign material. Adjuvants can also be used to enhance the efficacy of vaccine by helping to subvert the immune response to particular cells type of immune system, for example by activating the T cells instead of antibody-secreting B cells depending on the type of the vaccine.

As used herein, the term "dosage regime" refers to vaccine administration regarding formulation, route of administration, vaccine dose, dosing interval and duration of immune protection.

"Effective amount" or "therapeutically effective amount" refers to that amount of a composition, virus, or vaccine, which, when administered to a mammal, preferably a human, is sufficient to effect treatment of a disease or condition, or prevention of a disease or condition, in the mammal, preferably a human. The amount of a compound, virus, or vaccine, which constitutes a "therapeutically effective amount" will vary depending on the compound, virus, or vaccine, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" can be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular forms only and is not intended to be limiting.

A. Compositions

The compositions described herein are live-attenuated viruses with genomes genetically engineered from wild-type viral genomes with human codon usage bias to have mutated codons. The mutated codons have an avian codon usage bias, such as avian viral codon usage bias. The live-attenuated viruses can be generated from any virus infecting a mammal. Generally, the live-attenuated viruses can be generated from any virus infecting a human.

1. Viruses

Examples of viruses suitable for generating live-attenuated viruses include viruses of virus families Adenoviridae, Papillomaviridae, Parvoviridae, Herpesviridae, Poxviridae, Hepadnaviridae, Polyomaviridae, Anelloviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae. Viruses must generate mRNAs from their genomes to produce proteins and replicate themselves, but different mechanisms are used to achieve this in each virus family. Viral genomes may be single-stranded (ss) or double-stranded (ds), RNA or DNA, and may or may not use reverse transcriptase (RT). In addition, ssRNA viruses may be either sense (+) or antisense (−).

This classification places viruses into seven groups:

I: dsDNA viruses (e.g. Adenoviruses, Herpesviruses, Poxviruses)

II: ssDNA viruses (+strand or "sense") DNA (e.g. Parvoviruses)

III: dsRNA viruses (e.g. Reoviruses)

IV: (+)ssRNA viruses (+strand or sense) RNA (e.g. Picornaviruses, Togaviruses)

V: (−)ssRNA viruses (−strand or antisense) RNA (e.g. Orthomyxoviruses, Rhabdoviruses)

VI: ssRNA-RT viruses (+strand or sense) RNA with DNA intermediate in life-cycle (e.g. Retroviruses)

VII: dsDNA-RT viruses (e.g. Hepadnaviruses)

Examples of DNA and RNA viruses are presented in Table 2 and Table 3.

TABLE 2

Examples of DNA viruses useful for generating live-attenuated viruses.

| Virus Family | Examples (common names) | Virion naked/ enveloped | Capsid Symmetry | Nucleic acid type | Group |
| --- | --- | --- | --- | --- | --- |
| 1. Adenoviridae | Adenovirus, Infectious canine hepatitis virus | Naked | Icosahedral | ds | I |
| 2. Papillomaviridae | Papillomavirus | Naked | Icosahedral | ds circular | I |
| 3. Parvoviridae | Parvovirus B19, Canine parvovirus | Naked | Icosahedral | ss | II |
| 4. Herpesviridae | Herpes simplex virus, varicella-zoster virus, cytomegalovirus, Epstein-Barr virus | Enveloped | Icosahedral | ds | I |
| 5. Poxviridae | Smallpox virus, cow pox virus, sheep pox virus, orf virus, monkey pox virus, vaccinia virus | Complex coats | Complex | ds | I |
| 6. Hepadnaviridae | Hepatitis B virus | Enveloped | Icosahedral | circular, partially ds | VII |
| 7. Polyomaviridae | Polyoma virus; JC virus (progressive multifocal leukoencephalopathy) | Naked | Icosahedral | ds circular | I |
| 8. Anelloviridae | Torque teno virus | | | | |

TABLE 3

Examples of RNA viruses useful for generating live-attenuated viruses.

| Virus Family | Examples (common names) | Capsid naked/enveloped | Capsid Symmetry | Nucleic acid type | Group |
| --- | --- | --- | --- | --- | --- |
| 1. Reoviridae | Reovirus, Rotavirus | Naked | Icosahedral | ds | III |
| 2. Picornaviridae | Enterovirus, Rhinovirus, Hepatovirus, Cardiovirus, Aphthovirus, Poliovirus, Parechovirus, Erbovirus, Kobuvirus, Teschovirus, Coxsackie | Naked | Icosahedral | ss | IV |
| 3. Caliciviridae | Norwalk virus | Naked | Icosahedral | ss | IV |
| 4. Togaviridae | Rubella virus | Enveloped | Icosahedral | ss | IV |
| 5. Arenaviridae | Lymphocytic choriomeningitis virus | Enveloped | Complex | ss(−) | V |
| 6. Flaviviridae | Dengue virus, Hepatitis C virus, Yellow fever virus | Enveloped | Icosahedral | ss | IV |
| 7. Orthomyxoviridae | Influenza virus A, Influenza virus B, Influenza virus C, Isavirus, Thogotovirus | Enveloped | Helical | ss(−) | V |
| 8. Paramyxoviridae | Measles virus, Mumps virus, Respiratory syncytial virus, Rinderpest virus, Canine distemper virus | Enveloped | Helical | ss(−) | V |
| 9. Bunyaviridae | California encephalitis virus, Hantavirus | Enveloped | Helical | ss(−) | V |
| 10. Rhabdoviridae | Rabies virus | Enveloped | Helical | ss(−) | V |
| 11. Filoviridae | Ebola virus, Marburg virus | Enveloped | Helical | ss(−) | V |
| 12. Coronaviridae | Corona virus | Enveloped | Helical | ss | IV |
| 13. Astroviridae | Astrovirus | Naked | Icosahedral | ss | IV |
| 14. Bornaviridae | Borna disease virus | Enveloped | Helical | ss(−) | V |

TABLE 3-continued

Examples of RNA viruses useful for generating live-attenuated viruses.

| Virus Family | Examples (common names) | Capsid naked/enveloped | Capsid Symmetry | Nucleic acid type | Group |
|---|---|---|---|---|---|
| 15. Arteriviridae | Arterivirus, Equine Arteritis Virus | Enveloped | Icosahedral | ss | IV |
| 16. Hepeviridae | Hepatitis E virus | Naked | Icosahedral | ss | IV |

Viruses with a segmented genome are also suitable for forming live-attenuated viruses described herein. Viruses with segmented genomes include viruses of the family orthomyxoviridae, bunyaviridae and arenaviridae. Orthomyxoviridae include Influenza A virus, Influenza B virus and Influenza C virus. Bunyaviridae include Bunyamwera virus, LaCrosse virus, California encephalitis virus, Rift-Valley-fever virus and hamtaviruses. Arenaviridae include Lymphocytic choriomeningitis virus (LCMV), Lassa virus, Juni virus (Argentine haemorrhagic fever).

i. Live-Attenuated Viruses with Codon Usage Bias

Live-attenuated viruses of the present disclosure include one or more mutated codons having avian codon usage bias, such as avian viral codon usage bias. The mutated codons are generally generated from codons having human codon usage bias of the unattenuated, wild type viruses. The mutated codons having avian codon usage bias can be present in any number per gene, and in any number of genes, of the genome of the live-attenuated virus.

In some forms, the mutated codons having an avian codon usage bias are present in at least one gene, in at least two genes, in at least three genes, in at least four genes, in at least five genes, in at least six genes, in at least seven genes, or in at least eight genes. Typically, the mutated codons having avian codon usage bias are absent from genomic regions involving packaging or splicing, or overlapping reading frames encoding multiple proteins, of the live-attenuated virus.

Typically, the mutated codons having avian codon usage bias of the live-attenuated viruses do not change the amino acid sequence of the wild type virus, so that the live-attenuated virus do not have any amino-acid mutations relative to the wild type virus. Usually, the mutated codons having an avian codon usage bias are not temperature-sensitive mutations. Typically, the live-attenuated viruses can replicate in both upper and lower respiratory tracts, and can replicate at substantially the same rate at 33° C. and 37° C.

In some forms, the mutated codons having an avian viral codon usage bias are synonymous substitutions. In some forms, all of the mutated codons having an avian viral codon usage bias are synonymous substitutions. In some forms, some of the mutated codons having an avian viral codon usage bias are synonymous substitutions. In some forms, more than 90% of the mutated codons having an avian viral codon usage bias are synonymous substitutions. In some forms, more than 95% of the mutated codons having an avian viral codon usage bias are synonymous substitutions. In some forms, more than 98% of the mutated codons having an avian viral codon usage bias are synonymous substitutions. In some forms, more than 99% of the mutated codons having an avian viral codon usage bias are synonymous substitutions.

In some forms, the mutated codons having an avian viral codon usage bias are silent mutations. In some forms, all of the mutated codons having an avian viral codon usage bias are silent mutations. In some forms, some of the mutated codons having an avian viral codon usage bias are silent mutations. In some forms, more than 90% of the mutated codons having an avian viral codon usage bias are silent mutations. In some forms, more than 95% of the mutated codons having an avian viral codon usage bias are silent mutations. In some forms, more than 98% of the mutated codons having an avian viral codon usage bias are silent mutations. In some forms, more than 99% of the mutated codons having an avian viral codon usage bias are silent mutations.

In some forms, the live-attenuated virus does not have any amino acid mutations relative to the wild type virus. In some forms, the live-attenuated virus has fewer than 2 amino acid mutations relative to the wild type virus. In some forms, the live-attenuated virus has fewer than 3 amino acid mutations relative to the wild type virus. In some forms, the live-attenuated virus has fewer than 4 amino acid mutations relative to the wild type virus. In some forms, the live-attenuated virus has fewer than 5 amino acid mutations relative to the wild type virus. In some forms, the live-attenuated virus has fewer than 10 amino acid mutations relative to the wild type virus. In some forms, the live-attenuated virus has fewer than 20 amino acid mutations relative to the wild type virus. In some forms, the live-attenuated virus has less than 1% amino acid mutations relative to the wild type virus. In some forms, the live-attenuated virus has less than 2% amino acid mutations relative to the wild type virus. In some forms, the live-attenuated virus has less than 3% amino acid mutations relative to the wild type virus.

In some forms, the mutated codons having an avian viral codon usage bias are randomly but evenly distributed in the genome, chromosome, domain, gene, exon, region, or segment. In some forms, the coefficient of variation of the distance in codons between adjacent mutated codons having an avian viral codon usage bias in the genome, chromosome, domain, gene, exon, region, or segment is less than 70%. In some forms, the coefficient of variation of the distance in codons between adjacent mutated codons having an avian viral codon usage bias in the genome, chromosome, domain, gene, exon, region, or segment is less than 65%. In some forms, the coefficient of variation of the distance in codons between adjacent mutated codons having an avian viral codon usage bias in the genome, chromosome, domain, gene, exon, region, or segment is less than 60%. In some forms, the coefficient of variation of the distance in codons between adjacent mutated codons having an avian viral codon usage bias in the genome, chromosome, domain, gene, exon, region, or segment is less than 55%. In some forms, the coefficient of variation of the distance in codons between adjacent mutated codons having an avian viral codon usage bias in the genome, chromosome, domain, gene, exon, region, or segment is less than 54%. In some forms, the coefficient of variation of the distance in codons between adjacent mutated codons having an avian viral codon usage bias in the genome, chromosome, domain, gene, exon, region, or segment is less than 53%. In some forms, the coefficient of variation of the distance in codons between adjacent mutated codons having an avian viral codon usage bias in the genome, chromosome, domain, gene, exon, region, or segment is less than 52%. In some forms, the coefficient of variation of the distance in codons between adjacent mutated codons having an avian viral codon usage bias in the genome, chromosome, domain, gene, exon, region, or segment is less than 51%.

In some forms, the mutated codons having an avian viral codon usage bias are present in at least one gene, in at least two genes, in at least three genes, in at least four genes, in at least five genes, in at least six genes, in at least seven genes, or in at least eight genes.

TABLE 4

Overall codon usage (RSCU values) of Influenza virus types and their hosts.

| Amino acid | (abbr) | Codon | Anticodons | Influenza A H1N1 | H3N2 | Avian | Human | Pig | Mallard | Goose | Chicken |
|---|---|---|---|---|---|---|---|---|---|---|---|
| Ser | S | TCT | AGA, AGG, AGI | 1.12 | 0.91 | 1.09 | 1.13 | 0.99 | 1.04 | 1.30 | 1.09 |
| | | TCC | AGG, AGI | 0.87 | 0.97 | 0.89 | 1.31 | 1.50 | 1.24 | 1.44 | 1.21 |
| | | TCA | AGT, AGI | 1.62 | 1.58 | 1.34 | 0.90 | 0.73 | 0.76 | 0.79 | 0.89 |
| | | TCG | AGC, AGT | 0.14 | 0.21 | 0.34 | 0.33 | 0.39 | 0.30 | 0.24 | 0.40 |
| | | AGT | TCA, TCG, TCI | 1.15 | 0.95 | 1.22 | 0.90 | 0.77 | 0.80 | 0.75 | 0.86 |
| | | AGC | TCG, TCI | 1.11 | 1.38 | 1.12 | 1.44 | 1.62 | 1.86 | 1.47 | 1.55 |
| Phe | F | TTT | AAA, AAG, AAI | 0.98 | 0.96 | 0.88 | 0.93 | 0.79 | 0.81 | 0.99 | 0.91 |
| | | TTC | AAG, AAI | 1.02 | 1.04 | 1.12 | 1.07 | 1.21 | 1.19 | 1.01 | 1.09 |
| Thr | T | ACT | TGA, TGG, TGI | 1.11 | 1.28 | 1.17 | 0.99 | 0.83 | 0.93 | 1.01 | 0.99 |
| | | ACC | TGG, TGI | 0.96 | 0.72 | 0.87 | 1.42 | 1.68 | 1.50 | 1.81 | 1.23 |
| | | ACA | TGT, TGI | 1.74 | 1.67 | 1.67 | 1.14 | 0.92 | 1.06 | 0.93 | 1.20 |
| | | ACG | TGC, TGT | 0.19 | 0.34 | 0.29 | 0.46 | 0.57 | 0.51 | 0.26 | 0.57 |
| Asn | N | AAT | TTA, TTG, TTI | 1.20 | 1.15 | 1.18 | 0.94 | 0.79 | 0.79 | 1.09 | 0.86 |
| | | AAC | TTG, TTI | 0.80 | 0.85 | 0.82 | 1.06 | 1.21 | 1.21 | 0.91 | 1.14 |
| Lys | K | AAA | TTT, TTI | 1.27 | 1.39 | 1.15 | 0.87 | 0.76 | 0.86 | 0.84 | 0.89 |
| | | AAG | TTC, TTI | 0.73 | 0.61 | 0.85 | 1.13 | 1.24 | 1.14 | 1.16 | 1.11 |
| | * | TAA | | 0.78 | 1.41 | 0.87 | 0.89 | 0.82 | 1.49 | 1.57 | 0.97 |
| | | TAG | | 1.04 | 0.46 | 0.65 | 0.71 | 0.58 | 0.52 | 0.39 | 0.61 |
| | | TGA | | 1.17 | 1.13 | 1.47 | 1.40 | 1.61 | 0.99 | 1.04 | 1.42 |
| Glu | E | GAA | CTT, CTI | 1.15 | 1.14 | 1.15 | 0.84 | 0.72 | 0.83 | 1.02 | 0.86 |
| | | GAG | CTC, CTT | 0.85 | 0.86 | 0.85 | 1.16 | 1.28 | 1.17 | 0.98 | 1.14 |
| Tyr | Y | TAT | ATA, ATG, ATI | 1.09 | 1.13 | 1.15 | 0.89 | 0.73 | 0.67 | 0.77 | 0.80 |
| | | TAC | ATG, ATI | 0.91 | 0.87 | 0.85 | 1.11 | 1.27 | 1.33 | 1.23 | 1.20 |
| Val | V | GTT | CAA, CAG | 0.97 | 1.06 | 0.93 | 0.73 | 0.57 | 0.68 | 0.99 | 0.84 |
| | | GTC | CAG, CAI | 0.74 | 0.69 | 0.75 | 0.95 | 1.07 | 1.05 | 0.71 | 0.87 |
| | | GTA | CAT, CAI | 1.07 | 1.02 | 0.95 | 0.47 | 0.34 | 0.43 | 0.60 | 0.50 |
| | | GTG | CAC, CAT | 1.22 | 1.23 | 1.37 | 1.85 | 2.03 | 1.83 | 1.70 | 1.80 |
| Gln | Q | CAA | GTT, GTI | 1.33 | 1.36 | 1.12 | 0.53 | 0.44 | 0.57 | 0.62 | 0.54 |
| | | CAG | GTC, GTT | 0.67 | 0.64 | 0.88 | 1.47 | 1.56 | 1.43 | 1.38 | 1.46 |
| Met | M | ATG | | 1.00 | 1.00 | 1.00 | 1.00 | 1.00 | 1.00 | 1.00 | 1.00 |
| Cys | C | TGT | ACA, ACG, ACI | 1.09 | 0.79 | 0.89 | 0.91 | 0.79 | 0.71 | 0.66 | 0.80 |
| | | TGC | ACG, ACI | 0.91 | 1.21 | 1.11 | 1.09 | 1.21 | 1.29 | 1.34 | 1.20 |
| Leu | L | TTA | AAT, AAI | 0.91 | 0.62 | 0.62 | 0.46 | 0.32 | 0.35 | 0.39 | 0.45 |
| | | TTG | AAC, AAT | 1.27 | 1.30 | 1.15 | 0.77 | 0.67 | 0.71 | 0.71 | 0.81 |
| | | CTT | GAA, GAG, GAI | 0.97 | 1.24 | 1.10 | 0.79 | 0.65 | 0.72 | 1.03 | 0.80 |
| | | CTC | GAG, GAI | 0.59 | 0.78 | 0.99 | 1.17 | 1.35 | 1.27 | 1.06 | 1.08 |
| | | CTA | GAT, GAI | 1.00 | 0.96 | 0.82 | 0.43 | 0.33 | 0.34 | 0.40 | 0.38 |
| | | CTG | GAC, GAT | 1.27 | 1.11 | 1.33 | 2.37 | 2.68 | 2.60 | 2.41 | 2.48 |
| Ala | A | GCT | CGA, CGG, CCI | 1.13 | 1.06 | 1.08 | 1.06 | 0.96 | 1.20 | 1.62 | 1.16 |
| | | GCC | CGG, CGI | 0.87 | 0.93 | 0.71 | 1.60 | 1.80 | 1.34 | 1.42 | 1.27 |
| | | GCA | CGT, CGI | 1.74 | 1.73 | 1.84 | 0.91 | 0.74 | 1.02 | 0.75 | 1.06 |
| | | GCG | CGC, CGT | 0.26 | 0.28 | 0.37 | 0.42 | 0.50 | 0.44 | 0.21 | 0.51 |
| Trp | W | TGG | | 1.00 | 1.00 | 1.00 | 1.00 | 1.00 | 1.00 | 1.00 | 1.00 |
| Pro | P | CCT | GGA, GGG, GGI | 1.04 | 1.29 | 1.03 | 1.15 | 1.05 | 0.95 | 1.51 | 1.10 |
| | | CCC | GGG, GGI | 0.72 | 0.84 | 0.75 | 1.29 | 1.46 | 1.50 | 1.07 | 1.22 |
| | | CCA | GGT, GGI | 1.74 | 1.29 | 1.68 | 1.11 | 0.94 | 1.05 | 1.14 | 1.13 |
| | | CCG | GGC, GGT | 0.49 | 0.58 | 0.54 | 0.45 | 0.56 | 0.51 | 0.29 | 0.56 |
| His | H | CAT | GTA, GTG, GTI | 1.05 | 1.21 | 1.13 | 0.84 | 0.70 | 0.73 | 0.80 | 0.80 |
| | | CAC | GTG, GTI | 0.95 | 0.79 | 0.87 | 1.16 | 1.30 | 1.27 | 1.20 | 1.20 |
| Asp | D | GAT | CTA, CTG, CTI | 1.13 | 1.08 | 1.07 | 0.93 | 0.80 | 0.90 | 0.90 | 1.01 |
| | | GAC | CTG, CTI | 0.87 | 0.92 | 0.93 | 1.07 | 1.20 | 1.10 | 1.10 | 0.99 |
| Arg | R | CGT | GCA, GCG, GCI | 0.24 | 0.10 | 0.19 | 0.48 | 0.44 | 0.63 | 0.63 | 0.59 |
| | | CGC | GCG, GCI | 0.18 | 0.24 | 0.21 | 1.10 | 1.31 | 1.22 | 1.55 | 1.14 |
| | | CGA | GCT, GCI | 0.41 | 0.43 | 0.50 | 0.65 | 0.60 | 0.50 | 0.31 | 0.58 |
| | | CGG | GCC, GCT | 0.28 | 0.57 | 0.48 | 1.21 | 1.29 | 0.94 | 0.77 | 1.07 |
| | | AGA | TCT, TCI | 3.08 | 2.84 | 2.92 | 1.29 | 1.12 | 1.29 | 1.77 | 1.34 |
| | | AGG | TCC, TCT | 1.81 | 1.83 | 1.70 | 1.27 | 1.23 | 1.41 | 0.98 | 1.29 |
| Ile | I | ATT | TAA, TAG, TAI | 1.07 | 1.03 | 1.07 | 1.08 | 0.91 | 0.97 | 0.97 | 1.06 |
| | | ATC | TAG, TAI | 0.78 | 0.89 | 0.85 | 1.41 | 1.67 | 1.55 | 1.55 | 1.39 |
| | | ATA | TAT, TAI | 1.16 | 1.08 | 1.08 | 0.51 | 0.42 | 0.48 | 0.48 | 0.55 |

TABLE 4-continued

Overall codon usage (RSCU values) of Influenza virus types and their hosts.

| Amino acid | (abbr) | Codon | Anticodons | Average RSCU value | | | | | | | |
| --- | --- | --- | --- | --- | --- | --- | --- | --- | --- | --- | --- |
| | | | | Influenza A | | | | | | | |
| | | | | H1N1 | H3N2 | Avian | Human | Pig | Mallard | Goose | Chicken |
| Gly | G | GGT | CCA, CCG, CCI | 0.60 | 0.69 | 0.61 | 0.65 | 0.57 | 0.64 | 0.73 | 0.70 |
| | | GGC | CCG, CCI | 0.55 | 0.62 | 0.56 | 1.35 | 1.46 | 1.25 | 1.31 | 1.22 |
| | | GGA | CCT, CCI | 1.84 | 1.65 | 1.72 | 1.00 | 0.91 | 0.96 | 1.21 | 1.09 |
| | | GGG | CCC, CCT | 1.01 | 1.04 | 1.12 | 1.00 | 1.05 | 1.15 | 0.75 | 0.99 |

Under-represented codons (RSCU<0.6) are represented by italicized text, while the most commonly used codons are in bold.

Codon usage for each amino acid in a gene can be represented as a fraction, percentage, Relative Synonymous Codon Usage values (RSCU value, GC content, effective number of codons (ENC), Synonymous Codon Usage Order (SCUO), Codon Volatility, Codon Adaptation Index (CM) and Odds Ratio (Fancher et al., AJMB 1:174-182 (2011)). Any of these measures can be used to identify the codon usage of each of the codons of a wild type virus. Typically, the codons of a wild type virus displaying a human codon usage bias can be optimized for an avian host, i.e., mutated to have an avian codon usage bias. Table 4 represents the codon usage for each amino acid in a virus and its hosts, including human and avian hosts.

ii. Codons Having Codon Usage Bias

Generally, any techniques suitable for measuring codon usage bias can be used to identify codon usage bias in a virus, such as a human or avian virus. RSCU values were used as an exemplary techniques of measuring codon usage bias in the virus.

Generally, a codon having human viral codon usage bias is a codon with a higher RSCU value in a human virus than in a virus infecting another organism, such as an avian. Similarly, a codon having an avian viral codon usage bias is a codon with a higher RSCU value in an avian virus than in a virus infecting another organism, such as a human. Therefore, a codon can have an RSCU value that is substantially the same in the human and avian viruses. This codon can be said to have even usage between the two viruses. Also, a codon can have an RSCU value in a human virus that is greater than the RSCU value in an avian virus. This codon can be said to have a human viral codon usage bias. Similarly, a codon can have an RSCU value that is less than the RSCU value in the avian virus. This codon can be said to have an avian viral codon usage bias. Therefore, a codon having an RSCU value in one virus infecting one host, such as a human, that is greater than the RSCU value for the same codon in another virus infecting another host, such as an avian, can be said to have a human viral codon usage bias. Similarly, a codon having an RSCU value in one virus infecting one host, such as an avian, that is greater than the RSCU value for the same codon in another virus infecting another host, such as a human, can be said to have an avian viral codon usage bias. Accordingly, a codon having the same RSCU value in two different viruses infecting two different hosts can be said to have even viral codon usage bias, or no viral codon usage bias, between the two viruses.

Codons having substantially the same viral codon usage bias between the viruses are codons with about 0.1 to 2% difference between the values or measures used to measure viral codon usage bias. Such values could be, for example, RSCU values for the same codon in the different viruses infecting different hosts, differing from each other by 0.1 to 2%.

Codons having human viral codon usage bias relative to avian viral codon usage are codons with about 2 to 99.9% difference between the values or measures used to measure viral codon usage bias in human and avian viruses. Such values could be, for example, RSCU values for the same codon in the different viruses, differing from each other by 2 to 99.9%.

Codons having avian viral codon usage bias relative to human viral codon usage are codons with about 2 to 99.9% difference between the values or measures used to measure codon usage bias in human and avian viruses. Such values could be, for example, RSCU values for the same codon in the different viruses, differing from each other by 2 to 99.9%.

iii. Codon Optimization—Mutating Codons of a Human Virus to Codons Having Avian Viral Codon Usage Bias Mutating codons of a human virus to codons having avian viral codon usage bias involves mutating codons to obtain codons with, or closer to, avian viral codon usage bias. It is the degree of difference of codon usage between the human and the avian viruses that determines whether the codon has a higher or lower avian viral codon usage bias. The degree of difference can be as low as 2% or as high as 99.9%, and any percentage between 2% and 99.9%.

As an example of mutating codons in a human virus to avian viral codon usage bias, human influenza virus A/Brisbane/59/2007 was mutated to avian viral codon usage (Table 1). In this example, the codon usage is presented as frequency, such as number of times the codon is used. For a given amino acid in a specific segment, the average frequency of using the codons was calculated from avian viral sequences and compared to that of the target virus to determine the number of mutations required. In the case of Phe in PB2 segment of avian influenza viruses, UUU was used 9.3 times and UUC was used 14.7 times in avian sequences. For A/Brisbane/59/2007, UUU was used 13 times and UUC was used 11 times. To convert to avian viral codon usage bias, 4 mutations from UUU to UUC were introduced to PB2 segment. The same comparison was performed for all coding amino acids for all 8 segments. In other words, the ratio of the codons for a given amino acid in a segment of the virus was changed to match or come closer to the ratio of those codons in avian virus.

Generally, codon optimization involving changing codons from human viral codon usage bias to codons with avian viral codon usage bias can include mutating not one, but many codons. Typically, most of the mutated codons introduce a change from human viral codon usage bias to avian viral codon usage bias. However, some of the mutated codons may introduce no change in viral codon usage bias, or a change towards even higher human viral codon usage bias. In some forms, the number of mutated codons that introduce a change from human viral codon usage bias to avian viral codon usage bias is greater than the number of mutated codons that introduce no change in viral codon usage bias, or a change towards even higher human viral codon usage bias. The number of mutated codons, per gene, introducing a change from human viral codon usage bias to avian viral codon usage bias can be greater than 1, 1000, or any number between 1 and 1000.

2. Vaccines

One composition disclosed herein is a vaccine. The vaccine can contain nucleic acids, amino acids or a combination thereof. A vaccine (or an immunogenic composition) including an immunogenic amount (preferably an effective or protective amount) of a composition, such as an outer membrane protein, (either isolated or purified, or present in an outer membrane vesicle, ghost or killed, live, or live-attenuated whole cell preparation) in a pharmaceutically acceptable excipient, and an optional adjuvant. In this context, immunogenic amount can be defined as a sufficient quantity of protein to elicit an antibody response in a host.

An immunogenic amount of one of the disclosed compositions can be formulated in a pharmaceutically acceptable excipient, and an optional adjuvant, to prevent or treat infectious diseases. Vaccines can be used to induce an immune response in a mammal susceptible to infection by a pathogen by administering to the mammal an effective amount of the vaccine (an effective amount being an amount capable of protecting a host to some degree against an infection). A vaccine can also prevent an infection by administration to a mammal in an effective amount.

Vaccines are capable of eliciting a cross-protective immune response against a large variety of viruses.

The vaccines described herein are typically generated based on fundamental information about the pathogen, such as how it infects cells and how the immune system responds to it, as well as practical considerations, such as regions of the world where the vaccine is to be used. The vaccines described herein can be, for example, live, attenuated vaccines; inactivated vaccines; subunit vaccines; toxoid vaccines; conjugate vaccines; DNA vaccines; or recombinant vector vaccines.

Generally, the live-attenuated viruses described herein can be used in live, attenuated vaccines. An exemplary vaccine includes a live-attenuated influenza virus vaccine that can effectively protect a host against influenza by immunization with a single effective dose.

Vaccines can elicit a humoral response, cell-mediated immune response or a combination thereof. Ideally, the immune response provides protection upon subsequent challenge with the unattenuated virus of the same or a different subtype or strain. The live-attenuated viruses described herein, when used as vaccines, can provide homosubtypic immune protection, heterosubtypic immune protection, or both.

i. Live-Attenuated Vaccines

Live, attenuated vaccines contain a version of the living virus that has been weakened in the lab so it can't cause disease. Because a live, attenuated vaccine is the closest thing to a natural infection, these vaccines are good "teachers" of the immune system: They elicit strong cellular and antibody responses and often confer lifelong immunity with only one or two doses.

Despite the advantages of live, attenuated vaccines, there are some downsides. It is the nature of living things to change, or mutate, and the organisms used in live, attenuated vaccines are no different. The remote possibility exists that an attenuated virus in the vaccine could revert to a virulent form and cause disease. However, this possibility is significantly reduced by the introduction of a large number of mutations within a viral genome (see Table 6). Also, not everyone can safely receive live, attenuated vaccines. For their own protection, people who have damaged or weakened immune systems-because they've undergone chemotherapy or have HIV, for example—cannot be given live vaccines.

Another limitation is that live, attenuated vaccines usually need to be refrigerated to stay potent. If the vaccine needs to be shipped overseas and stored by healthcare workers in developing countries that lack widespread refrigeration, a live vaccine may not be the best choice.

ii. Inactivated Vaccines

Inactivated vaccines are produced by killing the disease-causing pathogen with chemicals, heat, or radiation. Such vaccines are more stable and safer than live vaccines: The dead pathogen can't mutate back to their disease-causing state. Inactivated vaccines usually don't require refrigeration, and they can be easily stored and transported in a freeze-dried form, which makes them accessible to people in developing countries.

Most inactivated vaccines, however, stimulate a weaker immune system response than do live vaccines. So it would likely take several additional doses, or booster shots, to maintain a person's immunity. This could be a drawback in areas where people don't have regular access to health care and can't get booster shots on time.

iii. Subunit Vaccines

Instead of the entire pathogen, subunit vaccines include only the antigens that best stimulate the immune system. In some cases, these vaccines use epitopes—the very specific parts of the antigen that antibodies or T cells recognize and bind to. Because subunit vaccines contain only the essential antigens and not all the other molecules that make up the microbe, the chances of adverse reactions to the vaccine are lower.

Subunit vaccines can contain 1 antigen, 20 antigens, any number of antigens between 1 to 20 antigens, or more than 20 antigens. Once the antigens that can best stimulate the immune system are identified, they can be made into subunit vaccines in one of two ways: 1) the pathogens are grown in the laboratory and then chemicals are used to break them apart and gather the important antigens; or 2) the antigens can be manufactured using recombinant DNA technology. Vaccines produced this way are called "recombinant subunit vaccines."

iv. Toxoid Vaccines

The toxoid vaccines are useful for pathogens that secrete toxins. These vaccines are used when a pathogen's toxin is the main cause of illness. The toxins are usually inactivated by treating them with formalin, a solution of formaldehyde and sterilized water. Such "detoxified" toxins, called toxoids, are safe for use in vaccines.

When the immune system receives a vaccine containing a harmless toxoid, it learns how to fight off the natural toxin. The immune system produces antibodies that lock onto and block the toxin. Vaccines against diphtheria and tetanus are examples of toxoid vaccines.

v. Conjugate Vaccines

Conjugate vaccines are usually made when the pathogen possesses an outer coating of polysaccharides, as many harmful bacteria do. Polysaccharide coatings disguise bacterium's antigens so that the immature immune systems of infants and younger children can't recognize or respond to them. Conjugate vaccines, a special type of subunit vaccine, get around this problem.

When making a conjugate vaccine, the antigens or toxoids from a pathogen that an infant's immune system can recognize are usually linked to the polysaccharides. The linkage helps the immature immune system react to polysaccharide coatings and defend against the disease-causing bacterium.

vi. DNA Vaccines

DNA vaccines use the genes of the pathogen that code for immunogenic antigens. It was found that when the genes for a pathogen's antigens are introduced into the body, some cells take up that DNA. The DNA then instructs those cells to make the antigen molecules. The cells secrete the antigens and display them on their surfaces. A DNA vaccine against a pathogen would evoke a strong antibody response to the free-floating antigen secreted by cells, and the vaccine also would stimulate a strong cellular response against the microbial antigens displayed on cell surfaces. In addition, DNA vaccines are relatively easy and inexpensive to design and produce.

So-called naked DNA vaccines consist of DNA that is administered directly into the body. These vaccines can be administered with a needle and syringe or with a needle-less device that uses high-pressure gas to shoot microscopic gold particles coated with DNA directly into cells. Sometimes, the DNA is mixed with molecules that facilitate its uptake by the cells.

vii. Recombinant Vector Vaccines

The recombinant vector vaccines are similar to DNA vaccines, but they use an attenuated virus or bacterium to introduce microbial DNA to cells of the body. "Vector" refers to the virus or bacterium used as the carrier. The carrier viruses ferry pathogen's DNA to cells. Recombinant vector vaccines closely mimic a natural infection and therefore stimulating the immune system.

Attenuated bacteria also can be used as vectors. In this case, the inserted genetic material causes the bacteria to display the antigens of other microbes on its surface. In effect, the harmless bacterium mimics a harmful microbe, provoking an immune response.

3. Carriers

Pharmaceutical compositions can be formulated in a conventional manner using one or more physiologically acceptable carriers including excipients and auxiliaries which facilitate processing of the active compounds into preparations which can be used pharmaceutically. Proper formulation is dependent upon the route of administration chosen. In one form, administration is through upper or lower airway mucosa by inhalation. Typical formulations include a carrier such as sterile saline or a phosphate buffered saline. Viscosity modifying agents and preservatives are also frequently added.

Optional pharmaceutically acceptable excipients especially for enteral, topical and mucosal administration, include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

Stabilizers are used to inhibit or retard decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

If desired, the compositions can also contain minor amount of nontoxic auxiliary substances such as wetting or emulsifying agents, dyes, pH buffering agents, or preservatives.

4. Adjuvants

In one form the adjuvant is the synthetic glycolipid alpha-galactosylceramide (αGalCer). Dendritic cells presenting antigens in the context of CD1d can lead to rapid innate and prolonged production of cytokines such as interferon and IL-4 by natural killer T cells (NKT cells). CD1d is a major histocompatibility complex class I-like molecule that presents glycolipid antigens to a subset of NKT cells. Advantageously, αGalCer is not toxic to humans and has been shown to act as an adjuvant, priming both antigen-specific CD4+ and CD8+ T cell responses. For example, it has been shown that αGalCer in conjunction with a malaria vaccine can lead to cytotoxic responses against infected cells, which is an ideal scenario for vaccines against infectious diseases. In addition to αGalCer, other glycolipids that function as adjuvants to activate NKT cell-mediated immune responses can be used.

In another form the adjuvant can be, but is not limited to, one or more of the following: oil emulsions (e.g., Freund's adjuvant); saponin formulations; virosomes and viral-like particles; bacterial and microbial derivatives including, but not limited to carbohydrates such as lipopolysachharide (LPS); immunostimulatory oligonucleotides; ADP-ribosylating toxins and detoxified derivatives; alum; BCG; mineral-containing compositions (e.g., mineral salts, such as aluminum salts and calcium salts, hydroxides, phosphates, sulfates, etc.); bioadhesives, mucoadhesives, or both; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants can also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor; and co-stimulatory molecules, such as those of the B7 family. Such proteinaceous adjuvants can be provided as the full-length polypeptide or an active fragment thereof, or in the form of DNA, such as plasmid DNA.

5. Live-Attenuated Influenza Viruses

In some forms, the live-attenuated viruses described herein are influenza type A or influenza type B viruses. The influenza type A or influenza type B viruses disclosed herein can be classified according to the World Health Organization's revised system of nomenclature for influenza viruses (Bulletin of the World Health Organization, 58 (4):585-591 (1980)). The revised system of nomenclature is similar to the 1971 system in that it consists of two parts: (a) a type and strain designation, and (b) for influenza A viruses, a description of the antigenic specificity of the surface antigens (H and N).

The strain designation for influenza virus types A, B, and C contains the following information:

1. A description of the antigenic type of the virus based on the antigenic specificity of the NP antigen (type A, B, or C).

2. The host of origin. This is not indicated for strains isolated from human sources but is indicated for all strains isolated from non-human hosts, e.g., swine, horse (equine), chicken, turkey. For viruses from non-human species, both the Latin binomial nomenclature and the common name of the host of origin are used, e.g., Anas acuta (pintail duck). Thereafter, the common name of the species is used for the strain, e.g., A/duck/USSR/695/76 (H2N3). When viruses are isolated from nonliving material, the nature of the material is specified, e.g., A/lake water/Wisconsin/1/79.

3. Geographical origin.
4. Strain number.
5. Year of isolation.

For influenza A viruses, the antigenic description, in parentheses, follows the strain designation and includes the following information:

(a) An index describing the antigenic character of the hemagglutinin, i.e., H1, H2, H3, H4, etc. The numbering of subtypes is a simple sequential system which applies uniformly to influenza viruses from all sources.

(b) An index describing the antigenic character of the neuraminidase, i.e., N1, N2, N3, N4, etc. As with the H antigen subtype, this is a simple sequential numbering system applied uniformly to all influenza A viruses.

An exemplary nomenclature for the Influenza type A viruses isolated from humans is presented in Table 5.

TABLE 5

Examples of reference strains and subtypes of hemagglutinin and neuraminidase antigens of influenza A viruses isolated from humans.

| H and N subtypes | Reference strains |
|---|---|
| H1N1 | A/PR/8/34 (H1N1) |
| | A/Weiss/43 (H1N1) |
| | A/FM1/47 (H1N1) |
| | A/England/1/51 (H1N1) |
| | A/Denver/1/57 (H1N1) |
| | A/New Jersey/8/76 (H1N1) |
| | A/USSR/90/77 (H1N1) |
| H2N2 | A/Singapore/1/57 (H2N2) |
| | A/Japan/305/57 (H2N2) |
| | A/England/12/64 (H2N2) |
| | A/Tokyo/3/67 (H2N2) |
| H3N2 | A/Hong Kong/1/68 (H3N2) |
| | A/England/42/72 (H3N2) |
| | A/Port Chalmers/1/73 (H3N2) |
| | A/Victoria/3/75 (H3N2) |
| | A/Texas/1/77 (H3N2) | i. Influenza Type A

A live, attenuated influenza A virus described herein, including, for example, a respective virus in a pharmaceutical composition, can be based on any influenza A virus such as a bird flu, human flu, swine influenza, equine influenza or a canine influenza. Various different influenza A virus subtypes exist, differing in the nature of the HA and NA glycoproteins on their surface. Influenza A viruses are accordingly usually categorized into subtypes based on the combination of protein forms of Hemagglutinin and Neuraminidase present, two proteins on the surface of the viral envelope. Eighteen Hemagglutinin forms (H1 to H18) and eleven Neuraminidase forms (N1 to N11) have been identified.

Suitable virus strains include, but are not limited to H1N1, H1N2, H1N3, H1N4, H1N5, H1N6, H1N7, H1N8, H1N9, H2N1, H2N2, H2N3, H2N4, H2N5, H2N6, H2N7, H2N8, H2N9, H3N1, H3N2, H3N3, H3N4, H3N5, H3N6, H3N7, H3N8, H3N9, H4N1, H4N2, H4N3, H4N5, H4N6, H4N7, H4N8, H5N1, H5N2, H5N3, H5N4, H5N6, H5N7, H5N8, H5N9, H6N1, H6N2, H6N3, H6N4, H6N5, H6N7, H6N8, H6N9, H7N1, H7N2, H7N3, H7N4, H7N5, H7N6, H7N7, H7N8, H7N9, H8N1, H8N2, H8N3, H8N4, H8N5, H8N6, H8N7, H9N1, H9N2, H9N3, H9N4, H9N5, H9N6, H9N7, H9N8, H9N9, H10N1, H10N2, H10N3, H10N4, H10N5, H10N6, H10N7, H10N8, H10N9, H11N1, H11N2, H11N3, H11N4, H11N5, H11N6, H11N7, H11N8, H11N9, H12N1, H12N2, H12N3, H12N4, H12N5, H12N6, H12N7, H12N8, H12N9, H13N1, H13N2, H13N3, H13N4, H13N5, H13N6, H13N8, 1114N3, H14N5, H14N6, H15N8, H15N9, H16N3. In some forms the influenza virus is one of the strains H1N1, H1N2, H2N2, H3N1, H3N2, H5N1 and H7N7.

An example of a H1N1 strain is Influenza A virus strain A/Brisbane/59/2007 (H1N1), A/Puerto Rico/8/1934(H1N1) with Gene bank accession number NC 002016, NC 002017, NC 002018, NC 002019, NC 002020, NC 002021, NC 002022, NC 002023. Further examples of a H1N1 strain are Influenza A strain A/Brevig Mission/1/1918 H1N1) (Influenza A virus (strain A/South Carolina/1/1918 H1N1), Influenza A strain A/Russia:St.Petersburg/8/2006 H1N1, Influenza A strain A/USA:Texas/UR06-0195/2007 H1N1-strain A/Brevig Mission/1/1918 H1N1, Influenza A strain A/South Carolina/1/1918 H1N1, Influenza A strain A/Swine/Iowa/15/1930 H1N1, Influenza A strain A/Wilson-Smith/1933 H1N1, Influenza A strain A/WS/1933 H1N1, and strain A/USA:Phila/1935 H1N1. A further example of a H1N1 strain is Influenza A virus strain A/New Zealand:South Canterbury/35/2000 H1N1. An example of a H1N2 strain is Influenza A virus strain A/Xianfeng/3/1989 H1N2. Two examples of a H1N3 strain are Influenza A/duck/NZL/160/1976 H1N3 and strain A/Whale/Pacific ocean/19/1976 H1N3. An example of a H1N4 strain is Influenza A virus strain A/mallard/Netherlands/30/2006 H1N4. An example of a H1N5 strain is Influenza A virus strain A/pintail duck/ALB/631/1981 H1N5. An example of a H1N6 strain is Influenza A virus strain A/murre/Alaska/305/1976 H1N6. An example of a H1N7 strain is Influenza A virus A/swine/England/191973/92 H1N7. An example of a H1N8 strain is strain A/Egyptian goose/South Africa/AI1448/2007. An example of a H2N1 strain is Influenza A virus strain A/Japan/Bellamy/57 H2N1. An example of a H2N2 strain is Influenza A virus strain A/Korea/426/68 H2N2 with Gene bank accession numbers NC 007366, NC 007367, NC 007368, NC 007369, NC 007370, NC 007374, NC 007375, NC 007376, NC 007377, NC 007378, NC 007380, NC 007381 and NC 007382. Three further examples of a H2N2 strain are Influenza A strain A/Japan/305/1957 H2N2, A/Czech Republic/1/1966 H2N2 and strain A/Singapore/1/1957 H2N2. An example of a H2N3 strain is Influenza A virus strain A/mallard/Minnesota/Sg-00692/2008 H2N3. An example of a H2N4 strain is A/mallard/Alberta/149/2002 H2N4. An example of a H2N5 strain is Influenza A virus strain A/tern/Australia/1/04 H2N5. An example of a 1-12N6 strain is Influenza A virus strain A/thick-billed murre/Alaska/44145-199/2006 H2N6. An example of a H2N7 strain is Influenza A virus strain A/northern shoveler/California/HKWF1128/2007 H2N7. An example of a H2N8 strain is Influenza A virus strain A/turkey/CA/1797/2008 H2N8. An example of a H2N9 strain is Influenza A virus strain A/duck/Germany/1972 H2N9. An example of a H3N1 strain is Influenza A virus strain A/mallard duck/ALB/26/1976 H3N1. An example of a H3N2 strain is Influenza A virus strain A/New York/392/2004 H3N2 with Gene bank accession numbers NC 007371, NC 007372 and NC 007373. Five further example of a H3N2 strain are Influenza A virus strain NX-31 H3N2, strain A/Hong Kong/5/1983 H3N2, A/Rio/6/69 H3N2, A/Hong Kong/MA/1968 H3N2 and Influenza A virus strain A/Shanghai/N12/2007 H3N2. An example of a H3N3 strain is Influenza A virus strain A/duck/Hong Kong/22A/1976 H3N3. An example of a H3N4 strain is Influenza A virus strain A/mallard duck/ALB/1012/1979 H3N4. An example of a H3N5 strain is Influenza A virus strain A/northern shoveler/California/HKWF1046/2007 H3N5. An example of a H3N6 strain is Influenza A virus strain A/Chicken/Nanchang/9-220/2000 H3N6. Examples of a H3N8 strain are Influenza A strain A/Equine/Miami/1/1963 H3N8 and strain A/Duck/Ukraine/1/1963 H3N8. An example of a H3N9 strain is Influenza A virus strain A/swan/Shimane/227/01 H3N9.

An example of a H4N1 strain is Influenza A virus strain A/chicken/Singapore/1992(H4N1). An example of a H4N2 strain is Influenza A virus strain A/duck/Hong Kong/24/1976(H4N2). An example of a H4N3 strain is Influenza A virus strain A/mallard/Sweden/65/2005(H4N3). An example of a H4N4 strain is Influenza A virus strain A/Grey teal/Australia/2/1979 H4N4. An example of a H4N5 strain is Influenza A virus strain A/duck/Hokkaido/1058/2001 (H4N5). Two examples of a H4N6 strain are Influenza A virus strain A/Duck/Czechoslovakia/1956 H4N6 and Influenza A virus strain A/Duck/Alberta/28/1976 H4N6. An example of a H4N7 strain is Influenza A virus strain A/duck/Mongolia/583/02 H4N7. An example of a H4N8 strain is Influenza A virus strain A/Chicken/Alabama/1/1975 H4N8. An example of a H4N9 strain is Influenza A virus strain A/WDk/ST/988/2000(H4N9). An example of a H5N1 strain is Influenza A virus (A/Goose/Guangdong/1/96(H5N1)) with Gene bank accession numbers NC 007357, NC 007358, NC 007359, NC 007360, NC 007362, NC 007363, and NC 007364. Further examples of a H5N1 strain are Influenza A strain A/Duck/Hong Kong/2986.1/2000 H5N1, Influenza A strain A/Silky Chicken/Hong Kong/SF189/2001 H5N1, Influenza A strain A/Chicken/Hong KongNU562/2001 H5N1, Influenza A strain A/Chicken/Hong Kong/FY150/2001 H5N1, Influenza A strain A/Chicken/Hong Kong/715.5/2001 H5N1, Influenza A strain A/Guinea fowl/Hong Kong/38/2002 H5N1, Influenza A strain A/Chicken/Hong Kong/31.2/2002 H5N1, Influenza A strain A/Chicken/Hong Kong/37.4/2002 H5N1, Influenza A strain A/Silky Chicken/Hong KongNU100/2002 H5N1, Influenza A strain A/Chicken/Hong Kong/96.1/2002 H5N1, Influenza A strain A/Chicken/Hong KongNU22/2002 H5N1, Influenza A strain A/Teal/China/2978.1/2002 H5N1, Influenza A strain A/Hong Kong/212/2003 H5N1, Influenza A strain A/Chicken/Shantou/4231/2003 H5N1, and Influenza A strain A/Goose/Guangxi/345/2005 H5N1. An example of a H5N2 strain is Influenza A strain A/Chicken/Pennsylvania/1370/1983 H5N2. An example of a H5N3 strain is Influenza A strain A/duck/Malaysia/F119-3/97 H5N3. An example of a H5N4 strain is Influenza A strain A/environment/New York/200269-18/2002 H5N4. An example of a H5N5 strain is Influenza A strain A/duck/Massachusetts/Sg-00440/2005 H5N5. An example of a H5N6 strain is A/duck/Potsdam/2216-4/1984 H5N6. An example of a H5N7 strain is A/mallard/Denmark/64650/03 H5N7. An example of a H5N8 strain is strain A/Duck/Ireland/113/1983 H5N8. Two examples of a H5N9 strain are Influenza A strain A/Turkey/Ontario/7732/1966 H5N9 and strain A/chicken/Italy/22AM 998 H5N9.

An example of a H6N1 strain is A/chicken/Taiwan/PF1/02(H6N1). An example of a H6N2 strain is Influenza A strain A/chicken/California/1316/2001(H6N2). An example of a H6N5 strain is Influenza A strain A/Shearwater/Australia/1972 H6N5. An example of a H6N8 strain is Influenza A strain A/Turkey/Minnesota/501/1978 H6N8. An example of a H7N1 strain is Influenza A strain A/Fowl plague virus/Rostock/8/1934 H7N1. An example of a H7N2 strain is Influenza A strain A/duck/Hong Kong/293/1978(H7N2). An example of a H7N3 strain is Influenza A strain A/Turkey/Oregon/1971 H7N3. Five examples of a H7N7 strain are Influenza A strain A/Equine/C.Detroit/1/1964 H7N7, Influenza A strain A/Equine/Cambridge/1/1973 H7N7 and Influenza A strain A/Equine/Sao Paulo/1/1976 H7N7, Influenza A virus strain A/Equine/Prague/1/1956 H7N7 and Influenza A virus strain A/Chicken/Weybridge H7N7. An example of a H8N2 strain is Influenza A strain A/duck/Alaska/702/1991 (H8N2). An example of a H8N4 strain is Influenza A strain A/Turkey/Ontario/6118/1968 H8N4. An example of a H8N4 strain is Influenza A strain A/duck/Tsukuba/255/2005 (H8N5). An example of a H8N7 strain is Influenza A strain A/duck/Alaska/702/1991(H8N7).

An example of a H9N1 strain is Influenza A virus A/Duck/Shantou/2030/00(H9N1). An example of a H9N2 strain is Influenza A virus A/Hong Kong/1073/99(H9N2) with Gene bank accession numbers NC 004905, NC 004906, NC 004907, NC 004908, NC 004909, NC 004910, NC 004911, and NC 004912. An example of a H9N3 strain is Influenza A virus A/duck/Viet Nam/340/2001 H9N3. An example of a H9N4 strain is Influenza A virus A/shorebird/DE/231/2003 H9N4. An example of a H9N5 strain is Influenza A virus A/Duck/Hong Kong/702/79 H9N5. An example of a 119N7 strain is A/turkey/Scotland/70(H9N7). An example of a H9N8 strain is A/chicken/Korea/04164/2004(H9N8). An example of a H9N9 strain is A/turkey/France/03295/2003 H9N9. An example of a H10N1 strain is Influenza A virus A/duck/Hong Kong/938/80 H10N1. An example of a H10N2 strain is Influenza A virus A/duck/Alaska/658/1991 H10N2. An example of a H10N5 strain is Influenza A virus A/duck/Hong Kong/15/1976 H10N5. Examples of a H10N7 strain are Influenza A strain A/Chicken/Germany/n/1949 H10N7, strain A/Duck/Germany/1949 H10N7, and strain A/Duck/Manitoba/1/1953 H10N7. An example of a H10N7 strain is Influenza A virus strain A/Duck/Germany/1949 H10N7. An example of a H11N1 strain is Influenza A virus strain A/duck/Miyagi/47/1977 H11N1. An example of a 1111N2 strain is A/duck/Yangzhou/906/2002 H11N2. An example of a H11N3 strain is A/duck/Thailand/CU5388/2009 H11N3. An example of a H11N6 strain is Influenza A virus strain A/Duck/England/1/1956 H11N6. An example of a H11N8 strain is strain A/Duck/Ukraine/2/1960 H11N8. Two examples of a H11N9 strain are Influenza A strain A/Duck/Ukraine/1/1960 H11N9 and Influenza A strain A/Tern/Australia/G70C/1975 H11N9. An example of a H12N1 strain is A/mallard duck/Alberta/342/1983(H12N1). An example of a H12N2 strain is A/duck/Primorie/3691/02 H12N2. An example of a H12N3 strain is A/whooper swan/Mongolia/232/2005 H12N3. An example of a H12N5 strain is Influenza A virus strain A/Duck/Alberta/60/1976 H12N5. An example of a H12N6 strain is A/mallard/Alberta/221/2006 H12N6. An example of a H12N7 strain is A/duck/Victoria/30a/1981 H12N7. An example of a H12N8 strain is A/mallard/Netherlands/20/2005 H12N8. An example of a H12N9 strain is A/red-necked stint/Australia/5745/1981 H12N9.

An example of a H13N1 strain is A/bird feces/Illinois/185997-30/2007 H13N1. An example of a H13N2 strain is Influenza A virus strain A/Whale/Maine/328/1984 H13N2. An example of a H13N3 strain is A/shorebird/NJ/840/1986 H13N3. Two examples of a H13N6 strain are Influenza A virus strain A/Gull/Maryland/704/1977 H13N6 and strain A/Gull/Minnesota/945/1980 H13N6. An example of a H13N8 strain is A/black-headed gull/Sweden/1/2005 H13N8. An example of a H14N3 strain is A/mallard/Gur/263/82 H14N3. Three examples of a H14N5 strain are A/mallard/Gurjev/263/1982 H14N5, A/mallard/Astrakhan/266/1982 H14N5 and A/herring gull/Astrakhan/267/1982 H14N5. An example of a H14N6 strain is strain A/Mallard/Gurjev/244/1982 H14N6. An example of a H15N8 strain is A/duck/Australia/341/1983 H15N8. An example of a H15N9 strain is A/shearwater/West Australia/2576/79 H15N9. An example of a H16N3 strain is A/black-headed gull/Sweden/2/99 H16N3.

Such virus subtypes are distinguishable serologically, which means that antibodies specific for one subtype do not bind to another subtype with comparable high affinity. Nevertheless the nucleic acid positions characterizing the genes of an Influenza A virus according to the present invention apply to any Influenza A virus strain.

ii. Influenza Type B

The live-attenuated virus described herein can also be influenza type B virus. The live-attenuated influenza type B virus, including live-attenuated influenza type B virus in a pharmaceutical composition, can be based on any influenza B virus strain. Suitable virus strains include, but are not limited to Influenza B virus strain B/Maryland/1959, strain B/Yamagata/1/1973, strain B/Victoria/3/1985, strain B/USSR/100/1983, strain B/Tokyo/942/1996, strain B/Texas/4/1990, strain B/Singapore/222/1979, strain B/South Dakota/5/1989, strain B/Paris/329/1990, strain B/Leningrad/179/1986, strain B/Hong Kong/8/1973, strain B/Fukuoka/80/1981, strain B/Bangkok/163/1990, strain B/Beijing/1/1987, strain B/Switzerland/9359/99, strain B/Wisconsin/6/2006, strain B/West Virginia/01/2009, strain B/Washington/08/2009, strain B/Uruguay/NG/02, strain B/Texas/18/2001, strain B/Taiwan/S117/2005, strain B/Taiwan/3799/2006, strain B/Spain/WV45/2002, strain B/Seoul/232/2004, strain B/Rio Grande do Sul/57/2008, strain B/Quebec/517/98, strain B/Philippines/5072/2001, strain B/Oslo/1871/2002, strain B/Osaka/983/1997, strain B/Milan/05/2006, strain B/Johannesburg/116/01 or strain B/Arizona/12/2003.

iii. Codons Changed to Avian Codon Usage Bias

In one form, the live-attenuated viruses described herein include Influenza viruses in which at least one, at least two, at least three, at least four, at least five, at least six, at least seven, or at least eight of the genomic segments have been mutated so that at least one codon per segment with a human codon usage bias has been changed to a codon with an avian codon usage bias, such as avian virus codon usage bias.

The number of codons changed from human to avian codon usage bias per segment can vary. As many as 100 codons or more per segment can be changed. Typically, the number of codons changed, per segment, from human to avian viral codon usage bias is 3, 100, or any number between 3 and 100, or 15, 80, or any number between 15 and 80. Specific codon changes are indicated in Tables 6-8, and presented in SEQ ID NOS: 1-16.

For example, the viral RNA segment PB2 received a total of 62 codon substitutions, as presented in SEQ ID NO: 2 (avian-biased codons) when compared to SEQ ID NO: 1 (wild type) (represented, by convention, as DNA).

B. Methods of Making

1. Generating Live-Attenuated Viruses

To generate a live-attenuated virus, the unattenuated, wild type viral genome is screened to identify codon usage frequency and codons with human codon usage bias (Table 6). The codons with human codon usage bias are then identified for mutation. One or more of the identified codons are mutated to change the codons from having human codon usage bias to having avian codon usage bias. In order to avoid affecting critical viral RNA signal essential for the virus replication, mutations were introduced into the regions that (1) are not involved in vRNP packaging, (2) are not involved in splicing, and (3) do not encode multiple viral proteins. With the exception of the critical regions as described herein, the mutations are randomly, yet evenly, distributed in targeted viral genome. Specifically, these mutations were introduced into sites that are highly conserved at the amino acid level (>99%), but not at the nucleotide level.

i. Generating Viral Genome with Avian Codon Usage Bias

The codons identified for mutation from having a human codon usage bias to avian codon usage bias are typically generated using any suitable molecular biology techniques. Examples of suitable molecular biology techniques include targeted mutagenesis of nucleic acids, such as site-directed mutagenesis of the viral genome, DNA synthesis or RNA synthesis of a region of a genome, and other suitable methods. See, *Short Protocols in Molecular Biology.* Chapter 8, John Wiley & Sons, edited by Ausubel et al, 5th ed. 2002.

ii. Packaging the Genome into Viral Particles

Methods of making recombinant viruses with segmented or singular genomes are generally known in the art. These include methods with standard reverse genetic techniques and genomic manipulation in molecular biology (Hoffmann et al., *Proc. Natl. Acad. Sci. USA*, 97(11):6108-6113 (2000); Zhou et al., *J. Virol.*, 72(4):3241-3247 (1998)). All the synthetic genes are usually subcloned into expression constructs. The constructs are then used to contact, i.e., infect, the same host cell in vitro. The host cell then produces the packaged viruses containing the manipulated genome. The packaged viruses are then harvested and their titer determined using standard virology techniques, and used for further characterization.

In other forms, methods of making the live-attenuated viruses of the present disclosure include contacting the same host cell with a wild type virus and a region of a genome of a live-attenuated virus containing the mutated codons, the entire genome of a live-attenuated virus containing the mutated codons, or a live-attenuated virus containing the mutated codons, wherein the live-attenuated virus is of the same or different subtype, strain or species as the wild type virus. Generally, the host cell is contacted with a wild type virus and the live-attenuated virus of the same subtype, strain, or species as the wild type virus. In some forms, the host cell is contacted with a wild type virus and the live-attenuated virus of a different subtype, strain or species as the wild type virus.

iii. Quantifying Viral Particles

Methods of quantifying viral particles are well known in the art. Examples include plaque-based assays for determining virus concentration in terms of infectious dose. Viral plaque assays determine the number of plaque forming units (pfu) in a virus sample, which is one measure of virus quantity. The focus forming assay (FFA) is a variation of the plaque assay, but instead of relying on cell lysis in order to detect plaque formation, the FFA employs immunostaining techniques using fluorescently labeled antibodies specific for a viral antigen to detect infected host cells and infectious virus particles before an actual plaque is formed. The FFA is particularly useful for quantifying classes of viruses that do not lyse the cell membranes, as these viruses would not be amenable to the plaque assay. Another assay is Endpoint Dilution Assay (50% Tissue Culture Infective Dose ($TCID_{50}$)). $TCID_{50}$ is the measure of infectious virus titer. This endpoint dilution assay quantifies the amount of virus required to kill 50% of infected hosts or to produce a cytopathic effect in 50% of inoculated tissue culture cells.

C. Kits

Also provided is a kit or kits for immunization of a subject with a live-attenuated virus described herein. The kit comprises the live-attenuated virus, a pharmaceutically acceptable carrier, an adjuvant, an applicator, and an instructional material for the use thereof. In further forms, the live-attenuated virus can be one or more poliovirus, one or more rhinovirus, one or more influenza virus, etc. More than one virus may be preferred where it is desirable to immunize a host against a number of different isolates of a particular virus. The instructions can provide any information that is useful for directing the administration of the live-attenuated viruses.

D. Methods of Using

1. Use as Pharmaceutical Compositions

A live-attenuated virus presented herein can be used for the prophylactic treatment of viral infections, therapeutic treatment of viral infections, or both; that is, it can be used for the treatment of viral infections, prevention of viral infections, or both. The live-attenuated viruses can be administered as a pharmaceutical composition through any route that is known in the art. Generally, the pharmaceutical compositions can be administered, for example, intravenously, subcutaneously, intramuscularly or, intranasally. For such purposes, the virus of the pharmaceutical composition can be provided in a suitable injectable or inhalable form. A live-attenuated virus of the present disclosure can, in some forms, be included in a device for applying the virus in an inhalable or injectable form to a subject.

A pharmaceutical composition that includes a live-attenuated virus of the present disclosure can be manufactured in a manner that is itself known, e.g., by means of conventional mixing, dissolving, granulating, dragée-making, levigating, emulsifying, encapsulating, entrapping or lyophilising processes. The composition can be an immunogenic composition such as a vaccine. The respective vaccine forming the main constituent of the vaccine composition of the disclosure can include a single antigen, a combination of antigens, a single virus, or a combination of viruses—for example, at least two or three viruses of the same species, including one or more reassortant(s).

Certain forms of any of the instant immunization and therapeutic methods further comprise administering to the subject at least one adjuvant. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund's incomplete adjuvant (FIA), saponin, Quil A, and QS-21.

Exemplary routes of administration of a pharmaceutical composition of the disclosure include oral, transdermal, and parenteral delivery. Suitable routes of administration can, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

As an illustrative example, for injection, a pharmaceutical composition according to the present disclosure can be formulated as an aqueous solution, for example in physiologically compatible buffers such as Hanks's solution, Ringer's solution, or physiological saline buffer. For oral administration, a respective pharmaceutical composition can be formulated readily by combining the virus with pharmaceutically acceptable carriers well known in the art. Such carriers enable a virus of the invention to be formulated as tablets, pills, lozenges, dragées, capsules, liquids, gels, syrups, slurries, suspensions and the like, for oral ingestion by a patient to be treated.

Pharmaceutical preparations for oral use can be obtained by adding a solid excipient, optionally grinding a resulting mixture, and processing the mixture of granules, after adding suitable auxiliaries, if desired, to obtain tablets or dragée cores. Suitable excipients are, in particular, fillers such as sugars, including lactose, glucose, sucrose, mannitol, or sorbitol; starches and derivatives thereof, such as, corn starch, dextrin and wheat starch, rice starch, potato starch, hydroxypropyl starch, wheat starch, gelatine, gum tragacanth, methyl cellulose, hydroxypropylmethyl-cellulose, sodium carboxymethylcellulose, polyvinylpyrrolidone (PVP), or combinations thereof; cellulose preparations such as, for example, methylcellulose, carboxylmethylcellulose and hydroxypropylcellulose; inorganic compounds, such as sodium chloride, boric acid, calcium sulfate, calcium phosphate and precipitated calcium carbonate. If desired, disintegrating agents can be added, such as the cross-linked polyvinyl pyrrolidone, agar, or alginic acid or a salt thereof such as sodium alginate.

Dragée cores are provided with suitable coatings. For this purpose, concentrated sugar solutions can be used which may optionally contain gum arabic, talc, polyvinyl pyrrolidone, carbopol gel, polyethylene glycol, titanium dioxide, or combinations thereof; lacquer solutions; and suitable organic solvents or solvent mixtures. Dyestuffs or pigments can be added to the tablets or dragée coatings for identification or to characterize different combinations of virus doses. Suitable fluidizing agents include, but are not limited to, magnesium oxide, synthetic aluminium silicate, metasilicic acid, magnesium aluminium oxide, hydrous silicic acid, anhydrous silicic acid, talc, magnesium stearate, and kaolin. Suitable binding agents include, but are not limited to, polyethylene glycol, polyvinyl pyrrolidine, polyvinyl alcohol, gum arabic, tragacanth, sodium alginate, gelatine, and gluten. Suitable stabilisers include, but are not limited to, proteins, such as albumin, protamine, gelatine and globulin; and amino acids and salts thereof. Suitable thickeners include, but are not limited to, sucrose, glycerine, methylcellulose, and carboxymethylcellulose. Suitable pH adjusting agents include, but are not limited to, hydrochloric acid, sodium hydroxide, phosphates, citrates, and carbonates.

Pharmaceutical compositions that can be used orally include, but are not limited to, push-fit capsules made of gelatine, as well as soft, sealed capsules made of gelatine and a plasticiser, such as glycerol or sorbitol. The push-fit capsules can contain the live-attenuated virus in admixture with filler such as lactose, binders such as starches, lubricants (such as talc or magnesium stearate), or both, and, optionally, stabilizers. In soft capsules, the virus(es) can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, a respective pharmaceutical composition can take the form of tablets or lozenges formulated in conventional manner.

For administration by inhalation, a pharmaceutical composition for use according to the present disclosure may conveniently be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin, for use in an inhaler or insufflator can be formulated containing a powder mix of the virus and a suitable powder base such as lactose or starch.

A respective pharmaceutical composition can be formulated for parenteral administration by injection, e.g., by bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending agents, stabilizing agents, dispersing agents, or combinations thereof.

Pharmaceutical formulations for parenteral administration include aqueous solutions of the virus in water-soluble form. Additionally, suspensions of the virus can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran.

In some forms an active ingredient, such as a virus as described herein, can be in powder form for constitution with a suitable vehicle, e.g., sterile pyrogen-free (SPF) water, before use.

Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human.

2. Dosage

Dosages and desired concentrations of the attenuated viruses of the present disclosure can vary depending on the particular use envisioned. The determination of the appropriate dosage or route of administration is well within the skill of an ordinary physician. Animal experiments provide reliable guidance for the determination of effective doses for human prophylactic and therapeutic use. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

The amount or dose of the material administered should be sufficient to affect a therapeutic or prophylactic response in a subject over a reasonable time frame. For example, the dose of the material should be sufficient to prevent a symptomatic infection by the unattenuated wild type virus. The dose should be sufficient to stimulate the immune response, to treat or prevent wild type virus infections, or both.

Many assays for determining an administered dose are known in the art. For purposes of the present methods, an assay which includes comparing the anti-viral antibodies and immune cell types present in response to several different doses of the attenuated virus administered to a set of mammals can be performed. The dose also can be determined by the existence, nature and extent of any adverse side effects that might accompany the administration. A variety of factors, such as age, body weight, general health, diet, sex, material to be administered, route of administration, and the severity of the condition being treated can be considered when determining dosage.

The dosage of a live-attenuated virus vaccine for a subject such as a mammalian adult organism can be from about $10^2$ to about $10^{15}$, e.g., about $10^3$ to about $10^{12}$, about $10^3$ to about $10^{10}$, about $10^3$ to about $10^8$, about $10^5$ to about $10^8$, about $10^3$ to about $10^6$, about $10^4$ to about $10^8$, about $10^4$ to about $10^7$, about $10^4$ to about $10^6$ or about $10^4$ to about $10^5$ plaque forming units (PFU)/kg, or any range or value therein. However, the dosage should be a safe and effective amount as determined by conventional methods, using existing vaccines as a starting point.

A pharmaceutical composition for use in accordance with the present disclosure can be formulated in conventional manner using one or more pharmacologically acceptable carriers that include excipients and auxiliaries, which facilitate processing of the virus into preparations that can be used pharmaceutically. Proper formulation is dependent upon the selected route of administration. A composition, including its components, is said to be "pharmacologically acceptable" if its administration can be tolerated by a recipient subject. Such an agent is said to be administered in a "therapeutically effective amount" if the amount administered is physiologically significant. A composition of the present disclosure is physiologically significant if its presence results in a detectable change in the physiology of a recipient subject, e.g., enhances at least one primary or secondary humoral or cellular immune response against at least one strain of an infectious virus.

In some forms, the effective dose of the live-attenuated viruses and pharmaceutical compositions described herein can generally include about $10^2$ p.f.u., $10^3$ p.f.u., $10^4$ p.f.u., $10^5$ p.f.u., $10^6$ p.f.u., $10^7$ p.f.u., $10^8$ p.f.u., $10^9$ p.f.u., or more per dose per administration. The rate of administration can vary. Generally, the rate of administration can be, for example, from once a month, once every three months, once every six months, annually, or as needed for buster vaccinations.

EXAMPLES

Example 1. Generation of Synthetic Viral Genes and Recombinant Viruses

Materials and Methods

Influenza A/Brisbane/59/2007 (H1N1) was used as the prototype virus in this study. A dataset for each viral segment from viruses that are of human or avian origin was established in our previous studies (Wong et al., *BMC Evolutionary Biology*, 10:253 (2010)). The codon usage bias observed from each segment-specific dataset was compared to the corresponding counterpart (e.g. human PB2 vs avian PB2). To generate a recombinant A/Brisbane/59/2007 virus with the largest open reading frame (ORF) in each viral segment has an avian-like viral codon usage bias, the segment-specific codon usage frequency of wild-type A/Brisbane/59/2007 with those deduced from the avian influenza sequences was compared. The analysis allowed to determine the number of mutations required to be introduced into the prototype virus for changing its codon bias from human-like to avian-like (Tables 6 and 7 and SEQ ID NOs: 1-16). In order to avoid affecting critical viral RNA signal essential for the virus replication, mutations were introduced into the regions that are not involved in 1) vRNP packaging and 2) splicing and 3) encoding multiple viral proteins (Gog et al., *Nucleic Acids Research* 35(6):1897-1907 (2007); Moss et al., RNA, 17:991-1011 (2011)). With the exception of the critical regions as described herein, the mutations were randomly, yet evenly, distributed in targeted viral RNA segment (SEQ ID NOs: 1-16). Specifically, these mutations were introduced into sites that are highly conserved at the amino acid level (>99%), but not at the nucleotide level.

Recombinant influenza viruses were generated using standard reverse genetic techniques (Hoffmann et al., *Proc. Natl. Acad. Sci. USA*, 97(11):6108-6113 (2000)). All the synthetic genes were subcloned into a dual viral RNNprotein expression construct (pHW2000) (Hoffmann et al., *Proc. Natl. Acad. Sci. USA*, 97(11):6108-6113 (2000)).

Results

Overall, 2 sets of viral genomes of A/Brisbane/59/2007, one for the wild-type viral sequences and one with avian-like codon usage bias, were synthesized. The mutated viral sequences were synthesized commercially. The wild-type and mutant viral RNA sequences are presented as SEQ ID NOS:1-16 (represented, by convention, as DNA). A total of 373 nucleotide mutations, corresponding to 351 codon mutations were introduced in the A/Brisbane/59/07 (H1N1) genome (Table 7) and all of these nucleotide changes were silent mutations. After introducing these mutations in the viral genome, the resultant A/Brisbane/59/2007 mutant has a viral genome encoding wild-type A/Brisbane/59/2007 viral proteins, but with the largest ORF of each segment having an avian-like viral codon usage bias. The nucleotide frequency, dinucleotide frequency and free energy of the mutated ORFs were also studied. In general, the mutated sequences were found to be more similar to those observed from avian sequences.

Wild-type virus, a mutant with 8 mutated segments (hereafter called as 8-mut) and mutants with 1-4 mutated segments were generated (Table 8). The rescued viruses were amplified in embryonated eggs and the identities of these viruses were confirmed by sequencing.

TABLE 6

Construction of A/Brisbane/59/07 (H1N1) influenza virus with avian codon usage bias.

| Segment | No. of mutations (Nucleotides)[a] | No. of mutations (Codon)[b] |
|---|---|---|
| PB2 | 62 (2.65%) | 62 (8.17%) |
| PB1 | 77 (3.29%) | 69 (9.11%) |
| PA | 65 (2.91%) | 61 (8.52%) |
| HA | 46 (2.59%) | 38 (6.73%) |
| NP | 31 (1.98%) | 30 (6.02%) |
| NA | 47 (3.21%) | 47 (10.00%) |
| M | 27 (2.63%) | 27 (10.71%) |
| NS | 18 (2.02%) | 17 (7.39%) |
| Total | 373 (2.74%) | 351 (8.26%) |

[a]Percentages were calculated by dividing the number of nucleotide mutations by the full length of the respective segment.
[b]Percentages were calculated by dividing the number of codon mutations by the number of amino acids of the corresponding protein. For PB1, M and NS segments, the minor protein products PB1-F2, M2, and NS2 proteins were excluded in the calculations, as no mutations was introduced to those regions.

TABLE 7

Number of mutations introduced into the ORFs of A/Brisbane/59/2007.

| From: | To: | Number |
|---|---|---|
| PB2 | | |
| AAA | AAG | 6 |
| AAT | AAC | 7 |
| ACT | ACC | 1 |
| ACT | ACA | 2 |
| ACT | ACG | 1 |
| AGA | AGG | 2 |
| ATT | ATC | 4 |
| ATT | ATA | 1 |

TABLE 7 -continued

Number of mutations introduced into the ORFs of A/Brisbane/59/2007.

| From: | To: | Number |
|---|---|---|
| CCT | CCC | 2 |
| CGG | CGA | 1 |
| CTA | CTG | 2 |
| CTT | CTG | 2 |
| GAA | GAG | 6 |
| GAT | GAC | 4 |
| GCG | GCA | 1 |
| GCT | GCA | 1 |
| GTA | GTG | 2 |
| TAC | TAT | 4 |
| TCA | TCG | 2 |
| TCA | TCC | 1 |
| TTA | TTG | 6 |
| TTT | TTC | 4 |
| Total | | 62 |

PB1

| From: | To: | Number |
|---|---|---|
| AAA | AAG | 10 |
| ACC | ACA | 5 |
| ACC | ACG | 2 |
| ACT | ACA | 5 |
| ACT | ACG | 2 |
| AGA | AGG | 4 |
| AGT | AGC | 2 |
| ATA | ATC | 3 |
| ATT | ATC | 3 |
| CGA | CGC | 1 |
| CGA | CGG | 1 |
| GCA | GCG | 2 |
| GCA | GCC | 1 |
| GGC | GGA | 5 |
| GGG | GGA | 2 |
| GGT | GGA | 4 |
| GTA | GTG | 1 |
| TCT | TCG | 1 |
| TCT | AGC | 1 |
| TTA | CTC | 3 |
| TTA | CTG | 3 |
| TTG | CTG | 3 |
| TTT | TTC | 5 |
| Total | | 69 |

PA

| From: | To: | Number |
|---|---|---|
| AAT | AAC | 7 |
| ACA | ACT | 2 |
| ACA | ACG | 2 |
| ATT | ATC | 3 |
| CAA | CAG | 2 |
| CAC | CAT | 1 |
| CCT | CCC | 1 |
| CGT | CGG | 1 |
| GAG | GAA | 12 |
| GAT | GAC | 1 |
| GCT | GCC | 6 |
| GGA | GGG | 2 |
| GTA | GTG | 3 |
| GTA | GTC | 2 |
| TCA | AGT | 1 |
| TCA | TCT | 3 |
| TCA | TCG | 2 |
| TCC | TCT | 1 |
| TGT | TGC | 1 |
| TTA | CTA | 2 |
| TTG | CTT | 1 |
| TTG | CTC | 1 |
| TTG | CTG | 1 |
| TTT | TTC | 3 |
| Total | | 61 |

HA

| From: | To: | Number |
|---|---|---|
| AAA | AAG | 4 |
| AAC | AAT | 1 |
| ACT | ACA | 1 |
| AGC | TCA | 1 |
| AGG | AGA | 1 |
| AGT | TCA | 1 |
| ATC | ATA | 1 |
| CCA | CCT | 2 |

TABLE 7-continued

Number of mutations introduced into the ORFs of A/Brisbane/59/2007.

| From: | To: | Number |
|---|---|---|
| CCA | CCC | 1 |
| CTG | CTA | 1 |
| CTG | CTC | 1 |
| CTT | CTC | 2 |
| GAA | GAG | 2 |
| GCC | GCA | 1 |
| GGA | GGG | 1 |
| GGT | GGC | 1 |
| GTA | GTG | 4 |
| GTA | GTT | 1 |
| GTC | GTT | 1 |
| TAT | TAC | 2 |
| TCC | TCA | 2 |
| TGT | TGC | 2 |
| TTA | CTC | 3 |
| TTG | CTC | 1 |
| Total | | 38 |

NP

| From: | To: | Number |
|---|---|---|
| AAT | AAC | 1 |
| ACA | ACT | 1 |
| AGC | AGT | 1 |
| CAA | CAG | 2 |
| CAC | CAT | 1 |
| CCC | CCG | 1 |
| CGC | CGT | 1 |
| CGG | CGA | 1 |
| CTT | CTG | 1 |
| GAG | GAA | 1 |
| GAT | GAC | 2 |
| GCC | GCG | 1 |
| GGA | GGG | 1 |
| GGT | GGG | 1 |
| GTA | GTT | 3 |
| GTC | GTT | 1 |
| TAC | TAT | 1 |
| TCA | TCG | 1 |
| TCT | TCC | 1 |

TABLE 7-continued

Number of mutations introduced into the ORFs of A/Brisbane/59/2007.

| From: | To: | Number |
|---|---|---|
| TTA | CTG | 1 |
| TTG | CTG | 4 |
| TTT | TTC | 2 |
| Total | | 30 |

NA

| From: | To: | Number |
|---|---|---|
| AAC | AAT | 2 |
| ACC | ACG | 1 |
| ACC | ACT | 1 |
| AGA | AGG | 2 |
| ATA | ATC | 1 |
| ATA | ATT | 1 |
| CAT | CAC | 1 |
| CAA | CAG | 4 |
| CCG | CCA | 2 |
| CCT | CCA | 1 |
| CCT | CCC | 1 |
| CGT | CGC | 1 |
| CGA | CGG | 1 |
| CTA | CTG | 1 |
| GAA | GAG | 1 |
| GCA | GCG | 1 |
| GCA | GCT | 2 |
| GGA | GGG | 6 |
| GGC | GGT | 2 |
| GTT | GTA | 4 |
| TAC | TAT | 2 |
| TCA | TCC | 4 |
| TGT | TGC | 2 |
| TTA | TTG | 1 |
| TTC | TTT | 2 |
| Total | | 47 |

AA

| From: | To: | Number |
|---|---|---|
| AAG | AAA | 1 |
| AAT | AAC | 3 |
| ACC | ACT | 1 |
| AGA | AGG | 1 |
| AGC | AGT | 1 |
| ATA | ATC | 1 |

TABLE 7 -continued

Number of mutations introduced into the ORFs of A/Brisbane/59/2007.

| From: | To: | Number |
|---|---|---|
| CAA | CAG | 2 |
| CGA | CGG | 1 |
| CTT | CTA | 3 |
| GAC | GAT | 1 |
| GCC | GCG | 1 |
| GCT | GCG | 1 |
| GGG | GGA | 1 |
| GGG | GGT | 1 |
| GTA | GTG | 1 |
| TAT | TAC | 2 |
| TCT | TCA | 1 |
| TCT | TCC | 1 |
| TGT | TGC | 1 |
| TTA | TTG | 2 |
| Total | | 27 |

NS

| From: | To: | Number |
|---|---|---|
| AAT | AAC | 1 |
| ACT | ACG | 1 |
| AGG | AGA | 3 |
| CAA | CAG | 1 |
| CCC | CCA | 1 |
| CGG | CGA | 1 |
| GAA | GAG | 1 |
| GGC | GGT | 2 |
| GTT | GTG | 2 |
| TCG | TCA | 1 |
| TGT | TGC | 1 |
| TTC | TTT | 1 |
| TTG | CTC | 1 |
| Total | | 17 |

TABLE 8

Codon bias mutants generated in this study.

| Segment | No. of mutations (Nucleotides)[a] | No. of mutations (Codon)[b] |
|---|---|---|
| PB2 | 62 (2.65%) | 62 (8.17%) |
| PB1 | 77 (3.29%) | 69 (9.11%) |
| PA | 65 (2.91%) | 61 (8.52%) |
| HA | 46 (2.59%) | 38 (6.73%) |
| NP | 31 (1.98%) | 30 (6.02%) |
| NA | 47 (3.21%) | 47 (10.00%) |
| M | 27 (2.63%) | 27 (10.71%) |
| NS | 18 (2.02%) | 17 (7.39%) |
| Total | 373 (2.74%) | 351 (8.26%) |

[a]WT: Wild-type segment; M: mutated segment

The position for each of the mutated nucleotides, and the nucleotide changes relative to the wild type genomic sequence of the A/Brisbane/59/07 virus in the 8-mut virus, are presented in Tables 9, 10, and 11. Complete sequences for each of the segments of the wild type A/Brisbane/59/07 viral genome and the corresponding 8-mut viral genome are presented as SEQ ID NOS: 1-16.

Complete sequences for each of the segments of the wild type A/Puerto Rico/8/34 (A/PR/8/34, or PR/8) viral genome and the corresponding 8-mut viral genome are presented as SEQ ID NOS: 17-32.

TABLE 9

List of nucleotide changes and their position in the 8-mut (MUT) virus relative to the nucleotides in the same position in the wild type A/Brisbane/59/07 (WT) viral genomic sequences for segments PB2, PB1, and PA. Ntd = nucleotide.

Genomic Segments

| PB2 | | | PB1 | | | PA | | |
|---|---|---|---|---|---|---|---|---|
| Ntd Position | Ntd in WT: SEQ ID NO: 1 | Ntd in MUT: SEQ ID NO: 2 | Ntd Position | Ntd in WT: SEQ ID NO: 3 | Ntd in MUT: SEQ ID NO: 4 | Ntd Position | Ntd in WT: SEQ ID NO: 5 | Ntd in MUT: SEQ ID NO: 6 |
| 137 | A | T | 140 | T | C | 197 | A | G |
| 152 | T | C | 197 | T | C | 227 | C | T |
| 182 | A | G | 224 | T | C | 269 | A | G |
| 212 | A | G | 233 | T | C | 278 | T | A |
| 254 | T | C | 235 | A | G | 284 | A | G |
| 290 | T | C | 295 | A | G | 302 | T | C |
| 341 | G | A | 303 | T | C | 341 | C | T |
| 404 | A | T | 311 | T | C | 362 | T | C |
| 410 | T | G | 359 | T | C | 416 | A | G |
| 485 | A | G | 368 | A | T | 431 | C | T |
| 494 | A | C | 446 | T | C | 440 | T | C |
| 521 | A | C | 448 | A | G | 461 | A | C |
| 566 | T | C | 500 | A | G | 491 | A | G |
| 596 | A | G | 524 | T | C | 506 | A | G |
| 611 | A | G | 526 | A | G | 523 | A | G |
| 632 | T | C | 535 | G | T | 638 | C | T |

TABLE 9-continued

List of nucleotide changes and their position in the 8-mut (MUT) virus relative to the nucleotides in the same position in the wild type A/Brisbane/59/07 (WT) viral genomic sequences for segments PB2, PB1, and PA. Ntd = nucleotide.

| Genomic Segments | | | | | | | | |
|---|---|---|---|---|---|---|---|---|
| PB2 | | | PB1 | | | PA | | |
| Ntd Position | Ntd in WT: SEQ ID NO: 1 | Ntd in MUT SEQ ID NO: 2 | Ntd Position | Ntd in WT: SEQ ID NO: 3 | Ntd in MUT: SEQ ID NO: 4 | Ntd Position | Ntd in WT: SEQ ID NO: 5 | Ntd in MUT: SEQ ID NO: 6 |
| 698 | A | G | 554 | C | T | 650 | A | G |
| 722 | G | A | 569 | G | T | 656 | T | G |
| 764 | T | C | 596 | A | G | 671 | A | G |
| 785 | A | G | 614 | T | G | 689 | T | C |
| 800 | C | T | 626 | A | T | 710 | C | G |
| 812 | A | G | 638 | T | G | 712 | A | G |
| 887 | T | C | 659 | T | C | 731 | C | T |
| 917 | A | G | 668 | T | G | 761 | A | G |
| 923 | T | C | 670 | A | G | 791 | G | A |
| 983 | T | C | 698 | G | T | 806 | A | G |
| 1028 | A | G | 734 | A | T | 821 | T | C |
| 1043 | C | T | 758 | A | G | 842 | T | C |
| 1091 | A | G | 759 | G | C | 878 | A | G |
| 1142 | T | C | 760 | A | T | 911 | A | G |
| 1187 | T | C | 785 | A | G | 950 | T | C |
| 1271 | A | G | 881 | T | C | 962 | C | T |
| 1307 | T | C | 893 | A | G | 1004 | T | A |
| 1403 | T | C | 911 | G | C | 1016 | A | G |
| 1424 | A | G | 973 | A | G | 1043 | A | G |
| 1472 | T | C | 998 | A | T | 1079 | C | T |
| 1484 | T | C | 1016 | A | T | 1163 | C | T |
| 1505 | A | T | 1058 | G | T | 1187 | T | G |
| 1547 | A | G | 1068 | G | T | 1211 | A | G |
| 1580 | A | T | 1115 | T | G | 1265 | A | G |
| 1613 | T | C | 1130 | T | G | 1271 | T | C |
| 1664 | A | G | 1133 | A | G | 1280 | A | G |
| 1682 | A | C | 1163 | A | T | 1331 | C | T |
| 1700 | G | A | 1223 | T | C | 1342 | A | G |
| 1766 | T | C | 1247 | A | G | 1370 | T | A |
| 1775 | T | C | 1286 | A | G | 1418 | T | A |
| 1805 | A | G | 1304 | A | G | 1670 | T | C |
| 1826 | A | G | 1343 | T | G | 1685 | C | A |
| 1883 | T | C | 1363 | A | G | 1687 | A | G |
| 1919 | A | G | 1409 | G | T | 1703 | A | G |
| 1958 | A | G | 1430 | A | C | 1763 | T | A |
| 1964 | A | G | 1460 | T | C | 1764 | G | C |
| 1976 | T | C | 1478 | T | C | 1765 | A | T |
| 2084 | T | C | 1556 | A | G | 1769 | A | G |
| 2102 | A | G | 1574 | T | G | 1826 | G | A |
| 2120 | T | C | 1595 | A | G | 1847 | T | C |
| 2144 | A | G | 1607 | T | C | 1868 | C | T |
| 2193 | T | C | 1616 | C | T | 1916 | T | A |
| 2213 | G | A | 1634 | G | T | 1937 | T | C |
| 2240 | T | C | 1652 | T | G | 1979 | C | T |
| 2279 | T | C | 1654 | A | G | 1996 | A | G |
| | | | 1676 | T | C | 2003 | A | G |
| | | | 1691 | T | C | 2045 | A | G |
| | | | 1700 | G | T | 2105 | A | G |
| | | | 1715 | G | C | 2132 | C | T |
| | | | 1730 | A | C | | | |
| | | | 1757 | T | C | | | |
| | | | 1769 | A | T | | | |
| | | | 1814 | T | C | | | |
| | | | 1838 | A | C | | | |
| | | | 1880 | A | T | | | |
| | | | 1934 | G | T | | | |
| | | | 1940 | T | C | | | |
| | | | 1943 | G | T | | | |
| | | | 1955 | T | C | | | |
| | | | 2015 | A | T | | | |
| | | | 2253 | A | G | | | |

TABLE 10

List of nucleotide changes and their position in the 8-mut (MUT) virus relative to the nucleotides in the same position in the wild type A/Brisbane/59/07 (WT) viral genomic sequences for segments HA, NP, and NA. Ntd = nucleotide.

| Genomic Segments | | | | | | | | |
|---|---|---|---|---|---|---|---|---|
| HA | | | NP | | | NA | | |
| Ntd Position | Ntd in WT: SEQ ID NO: 7 | Ntd in MUT: SEQ ID NO: 8 | Ntd Position | Ntd in WT: SEQ ID NO: 9 | Ntd in MUT: SEQ ID NO: 10 | Ntd Position | Ntd in WT: SEQ ID NO: 11 | Ntd in MUT: SEQ ID NO: 12 |
| 185 | T | C | 261 | A | G | 282 | G | A |
| 221 | T | C | 294 | T | C | 294 | G | C |
| 227 | G | T | 372 | G | A | 312 | A | T |
| 260 | T | A | 501 | A | G | 339 | T | C |
| 305 | A | G | 539 | A | G | 363 | T | C |
| 338 | T | G | 558 | A | G | 372 | A | T |
| 340 | A | G | 600 | A | C | 462 | A | G |
| 350 | T | C | 624 | T | A | 483 | T | C |
| 395 | A | T | 633 | G | A | 501 | T | A |
| 434 | A | G | 666 | T | A | 519 | T | C |
| 467 | T | C | 705 | G | A | 540 | T | C |
| 551 | T | C | 725 | A | G | 546 | T | G |
| 596 | G | T | 747 | A | G | 552 | A | G |
| 597 | C | G | 798 | T | C | 558 | G | A |
| 598 | T | A | 942 | T | C | 597 | G | A |
| 623 | T | C | 944 | A | G | 606 | A | G |
| 644 | A | G | 950 | A | G | 630 | T | A |
| 692 | A | G | 1011 | T | C | 654 | A | T |
| 701 | G | T | 1026 | A | G | 684 | G | A |
| 737 | G | A | 1041 | A | G | 705 | C | T |
| 758 | C | T | 1056 | G | A | 714 | G | A |
| 776 | G | A | 1068 | T | A | 732 | T | G |
| 785 | T | A | 1124 | A | G | 738 | G | A |
| 812 | T | C | 1143 | A | C | 762 | T | C |
| 902 | G | T | 1152 | G | C | 801 | T | C |
| 998 | C | G | 1158 | G | A | 840 | T | A |
| 1040 | T | C | 1221 | T | A | 861 | A | C |
| 1112 | T | C | 1236 | G | C | 882 | G | A |
| 1148 | T | G | 1356 | C | T | 894 | T | A |
| 1172 | T | C | 1383 | C | T | 909 | T | C |
| 1175 | A | G | 1431 | T | C | 918 | T | C |
| 1253 | C | G | | | | 927 | T | G |
| 1255 | A | G | | | | 942 | C | T |
| 1337 | T | C | | | | 960 | A | G |
| 1376 | A | T | | | | 969 | T | C |
| 1377 | C | G | | | | 981 | A | G |
| 1378 | T | A | | | | 987 | T | C |
| 1418 | T | A | | | | 1026 | T | C |
| 1424 | A | G | | | | 1035 | T | C |
| 1463 | G | T | | | | 1074 | T | G |
| 1484 | C | T | | | | 1080 | G | A |
| 1508 | T | G | | | | 1092 | T | G |
| 1510 | A | G | | | | 1101 | A | T |
| 1562 | T | G | | | | 1155 | T | C |
| 1564 | A | G | | | | 1221 | A | T |
| 1634 | A | G | | | | | | |

TABLE 11

List of nucleotide changes and their position in the 8-mut (MUT) virus relative to the nucleotides in the same position in the wild type A/Brisbane/59/07 (WT) viral genomic sequences for segments M and NS. Ntd = nucleotide.

| Genomic Segments | | | | | |
|---|---|---|---|---|---|
| M | | | NS | | |
| Ntd Position | Ntd in WT: SEQ ID NO: 13 | Ntd in MUT: SEQ ID NO: 14 | Ntd Position | Ntd in WT: SEQ ID NO: 15 | Ntd in MUT: SEQ ID NO: 16 |
| 343 | C | T | 391 | G | A |
| 352 | T | C | 415 | G | A |
| 385 | A | C | 421 | C | T |

TABLE 11-continued

List of nucleotide changes and their position in the 8-mut (MUT) virus relative to the nucleotides in the same position in the wild type A/Brisbane/59/07 (WT) viral genomic sequences for segments M and NS. Ntd = nucleotide.

| | Genomic Segments | | | | |
|---|---|---|---|---|---|
| | M | | | NS | |
| Ntd Position | Ntd in WT: SEQ ID NO: 13 | Ntd in MUT: SEQ ID NO: 14 | Ntd Position | Ntd in WT: SEQ ID NO: 15 | Ntd in MUT: SEQ ID NO: 16 |
| 415 | G | A | 442 | C | G |
| 430 | T | C | 444 | A | G |
| 442 | C | T | 445 | C | T |
| 482 | T | C | 466 | A | G |
| 505 | T | C | 517 | A | G |
| 511 | T | C | 526 | G | A |
| 520 | A | T | 538 | T | C |
| 535 | G | A | 544 | G | T |
| 550 | A | G | 565 | C | T |
| 565 | A | T | 574 | T | C |
| 586 | G | A | 580 | A | C |
| 631 | A | T | 592 | A | C |
| 643 | A | G | 604 | C | T |
| 646 | A | G | 664 | C | T |
| 658 | T | G | 685 | A | C |
| 667 | G | C | | | |
| 694 | A | T | | | |
| 700 | T | C | | | |
| 703 | A | G | | | |
| 730 | A | G | | | |
| 742 | A | G | | | |
| 757 | A | G | | | |
| 823 | T | C | | | |
| 829 | C | A | | | |

Example 2. The 8-Mut Virus is Attenuated in Mammalian Cells and in Mice

Materials and Methods

Virus replication kinetics of the WT and 8-mut viruses were determined in mammalian cells (MDCK and A549 cells) and embryonated eggs. To evaluate whether this virus was attenuated in mice, groups of 5 female BALB/C mice were infected intranasally with 6.75×10$^5$ p.f.u. of the WT or 8-mut virus. To determine whether the 8-mut virus still capable of inducing neutralizing antibodies in vivo, serum samples from infected mice were examined by microneutralization assay at 28 days post-infection. Groups of female BALB/c mice (N=3) were infected intranasally with 6.75× 10$^5$ p.f.u. of WT or 8-mut viruses. Sera were collected at 28 day post-infection for microneutralization assay against WT, and 8-mut viruses. Equal volume of sera from each mouse under the same group was pooled for the analysis. Sera were heat inactivated and serially 2-fold diluted from 1:10 to 1:1280. Sera were added to neutralize 100 TCID$_{50}$/35 µl of virus to prevent them from infecting MDCK cells. After 2 hours of neutralization, the mixture was added to MDCK cells and cytopathic effects were observed after 3 days. The reciprocal of the highest dilution of serum that neutralized at least 50% of virus infectivity was taken as the titer.

For the TCID$_{50}$ assay, the virus was diluted with 0.5 log serial dilutions and used to inoculate 4 wells of MDCK cells. After 3 days, the presence of infectious virus in each well was judged by observing the cytopathic effects on MDCK cells. The viral titer was determined using the Reed and Muench method. 1 TCID$_{50}$ represents the amount of virus will produce cytopathic effect in 50% of cell cultures inoculated.

In addition, bronchoalveolar lavage (BAL) fluid was collected from immunized mice at day 7 post-infection for immune cell profiling.

Expression of viral proteins in infected human A549 cells was also studies. Cells were mock-infected (mock) or infected with wild-type (WT) or 8-mut A/Brisbane/59/2007 virus at 5 multiplicity of infection (m.o.i.) and harvested at 8 hours post-infection. Total cell lysates were analyzed by Western blot using viral protein-specific antibodies as indicated. Beta-actin was used as a protein loading control.

Results

Figure 1A:
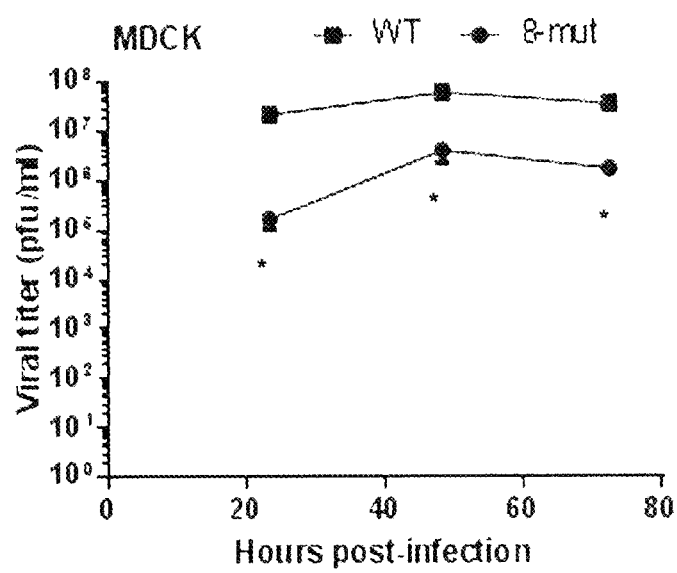
FIGS. 1A, 1B and 1C are graphs showing growth kinetics of WT and 8-mut viruses in canine MDCK cells (0.001 multiplicity of infection (m.o.i.), FIG. 1A), human A549 cells (0.01 m.o.i., FIG. 1B) and embryonated eggs (100 plaque forming units, FIG. 1C) Tissue culture supernatants or allanotic fluids were collected at 24, 48 and 72 hours post-infection. Viral titers were determined by plaque assays. * indicates p-value <0.05.
Figure 1B:
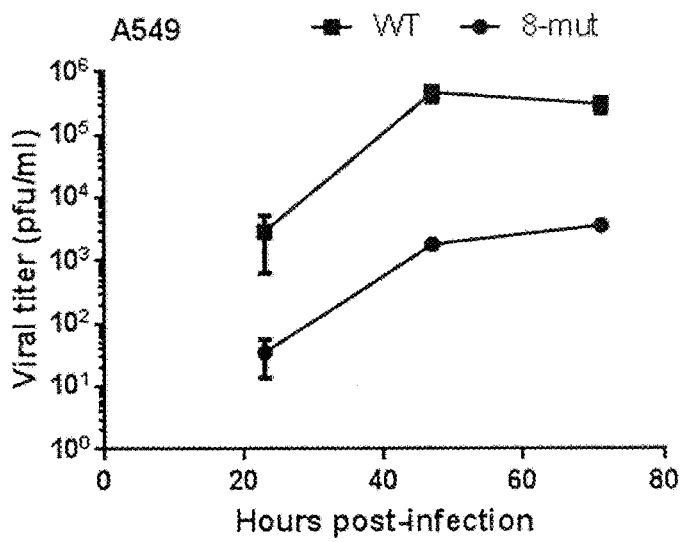
Figure 1C:
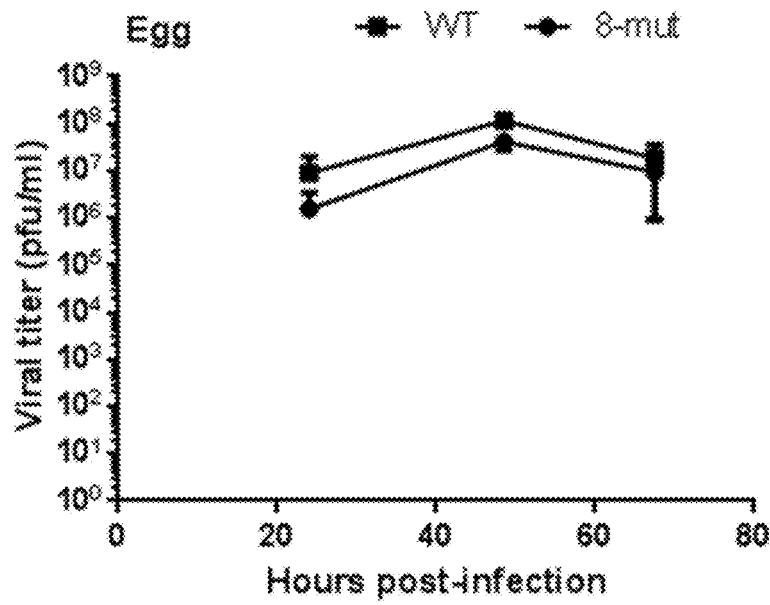

The replication of 8-mut virus was found to be attenuated in MDCK cells (FIG. 1A, >1 log). The 8-mut was even more attenuated in A549 cells (FIG. 1B) and it virus titers were at least 2 log less than the wild type. By contrast, the wild type and 8-mut virus have comparable titers in eggs (FIG. 1C). In addition, the plaque size of 8-mut virus was found to be smaller than the wild type in MDCK cells. The expression of wild-type and mutated genes were confirmed in infected humanA549 human cells. All the mutated genes were translated into proteins, as confirmed by Western blotting, indicating the mutated genes are all functional.

Figure 2A:
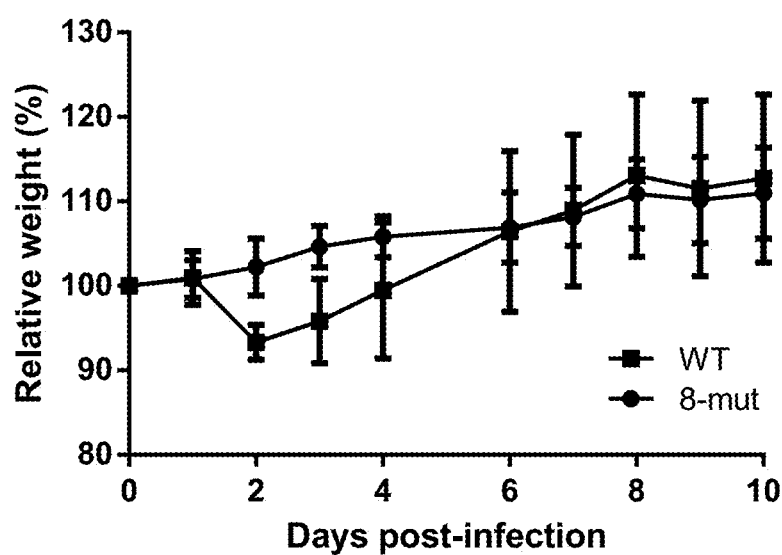
FIG. 2A is a graph showing change in relative weight (%) over time (days post-infection) of WT-virus and 8-mut virus-infected mice. Groups of female BALB/c mice (N=5 per group) were infected intranasally with $6.75 \times 10^5$ plaque forming unit (p.f.u.) of WT or 8-mut viruses. Body weight was monitored for 10 days and data represent mean±SD.
Figure 2B:
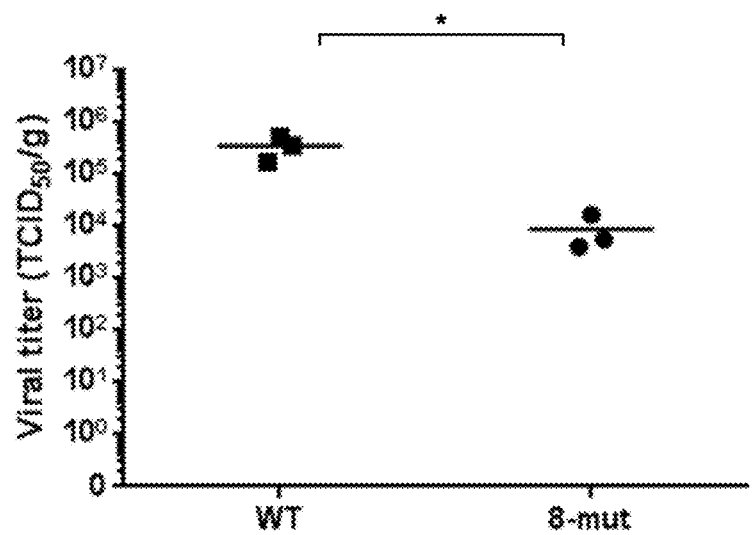
FIG. 2B is a graph showing viral titer ($TCID_{50}$/g) in the lungs of mice infected with WT or 8-mut virus. Lungs from infected mice were harvested at 3 days post-infection and viral titers were determined by standard $TCID_{50}$ on MDCK cells. Symbols represent data from individual mice. * indicates p-value<0.05.

Mice infected with the WT virus showed transient weight loss while those infected with the 8-mut virus did not show any weight loss or sickness (FIG. 2A). To examine their replication in mice, viral titers in lung tissues harvested at day 3 and day 7 post-infection were titrated by TCID$_{50}$ assay. The viral titers in mice infected with the 8-mut were about 40 times lower than those observed from the WT-infected mice (FIG. 2B), indicating that the 8-mut is attenuated in mice. No infectious virus was detected in mice infected with the WT or 8-mut viruses at day 7 post-infection (data not shown).

Figure 3:
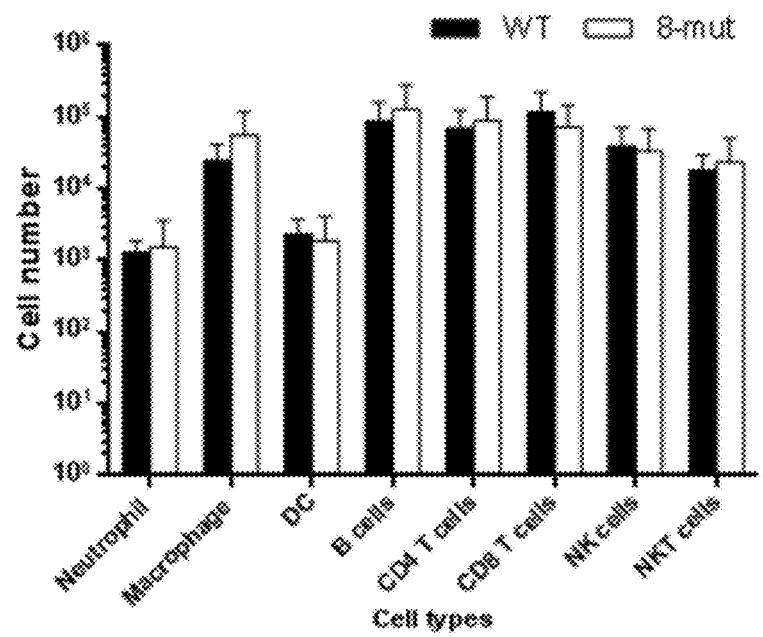
FIG. 3 is a graph of the number of innate and adaptive immune cell types in bronchoalveolar lavage fluid of mice infected with either WT or 8-mut viruses. The fluid was harvested at day 7 post-infection and stained with a mixture of antibodies for innate and adaptive immune cells, and analyzed by flow cytometry. Data represent total cell numbers (mean±SD).

Mice infected with the WT or 8-mut were found to have similar neutralizing titers against both WT and 8-mut (antibody titer: 1:640 to 1:1280) (Table 12). As indicated in FIG. 3, both WT and 8-mut virus infections could induce highly similar immune cell profiles in mice.

Overall, these results indicated the 8-mut was attenuated in various mammalian models. But its replication in eggs was not affected. Mice infected the 8-mut had no obvious clinical signs and developed robust antibody-mediated and cell-mediated responses.

TABLE 12

Data from microneutralization assay.

| Vaccination | Virus | |
| --- | --- | --- |
| | WT | 8-mut |
| WT | 1:640 | 1:1280 |
| 8-mut | 1:1280 | 1:1280 |

Example 3. The 8-Mut Virus Protects Mice from Viral Challenge

Materials and Methods

In order to determine whether the 8-mut can induce immune protection in mice, infected mice were subsequently subjected to a homologous or a heterologous challenge. Groups of 6 BALB/c mice were vaccinated intranasally with $6.75 \times 10^5$ p.f.u. of 8-mut virus, or were mock-vaccinated with PBS. Vaccinated or mock vaccinated mice were challenged with $4.3 \times 10^5$ p.f.u. of mouse-adapted A/Brisbane/59/07 virus (MA-WT) virus at day 28 post-vaccination. Lung tissues from treated mice were harvested at day 3 and 7 post-challenge for viral titration and immunohistochemistry staining.

Results

Figure 4A:
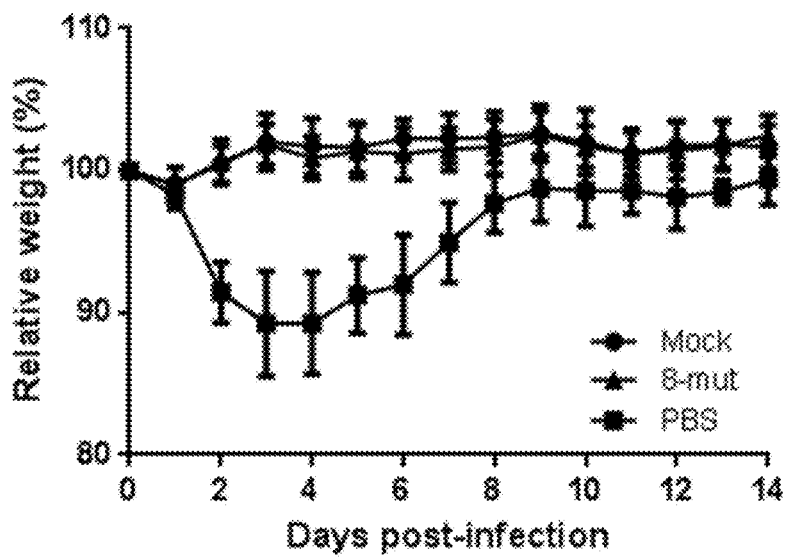
FIG. 4A is a graph showing a change in relative weight (%) at various days post-challenge in mice infected with mock infection (●), or previously vaccinated with 8-mut virus (▲), or PBS (■). Female BALB/c mice were vaccinated intranasally with PBS or $6.75 \times 10^5$ p.f.u. of 8-mut virus. At day 28 post-vaccination, mice were challenged with $4.3 \times 10^5$ p.f.u. of MA-WT virus or mock control. Body weights of 6 mice were monitored for 14 days and data represent means±SD.
Figure 4B:
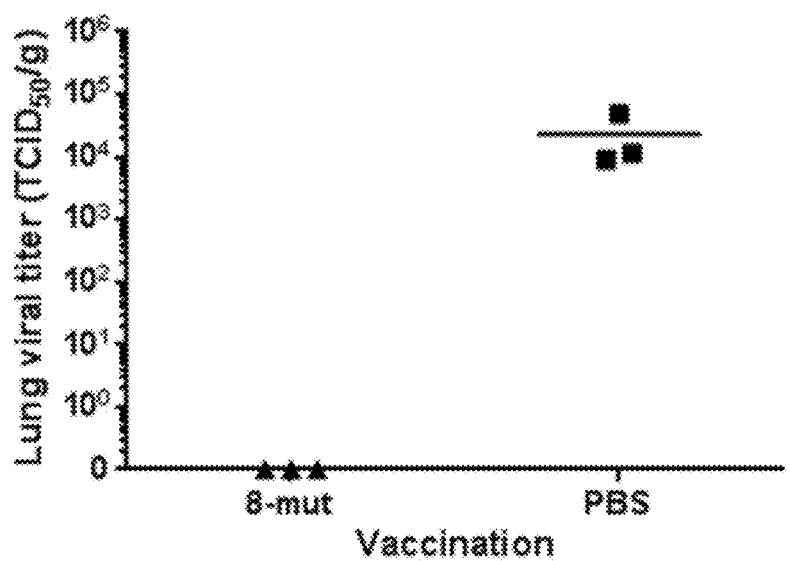
FIG. 4B is a graph showing the viral titer ($TCID_{50}$/g) in mouse lungs harvested 3 days post-challenge. Lungs were harvested from 3 mice at 3 days post-challenge and viral titers were determined by standard $TCID_{50}$ on MDCK cells. Symbols represent data from individual mice.

As the WT virus could only cause a mild weigh loss in mice (FIG. 2A), a more pathogenic mouse-adapted A/Brisbane/59/07 virus (MA-WT) (Xu et al., *PLoS ONE*, 6(12): e28901 (2011)) was used in the challenge. The PBS-vaccinated mice displayed moderate ruffling fur and mild hunching posture, and had significant weight loss (FIG. 4A). By contrast, the vaccinated mice showed no symptoms and no weight loss. High levels of virus replication were detected in PBS-treated, but not in vaccinated, mice at day 3 post-infection (FIG. 4B). In addition, cells expressing influenza NP proteins were only detected in mock-vaccinated mice at day 3 post-challenge. Influenza virus-positive cells were not detected in both groups at day 7 post-challenge. However, consolidation of the lung was observed in mock-vaccinated mice, but not in mice vaccinated with the 8-mut virus.

Figure 5A:
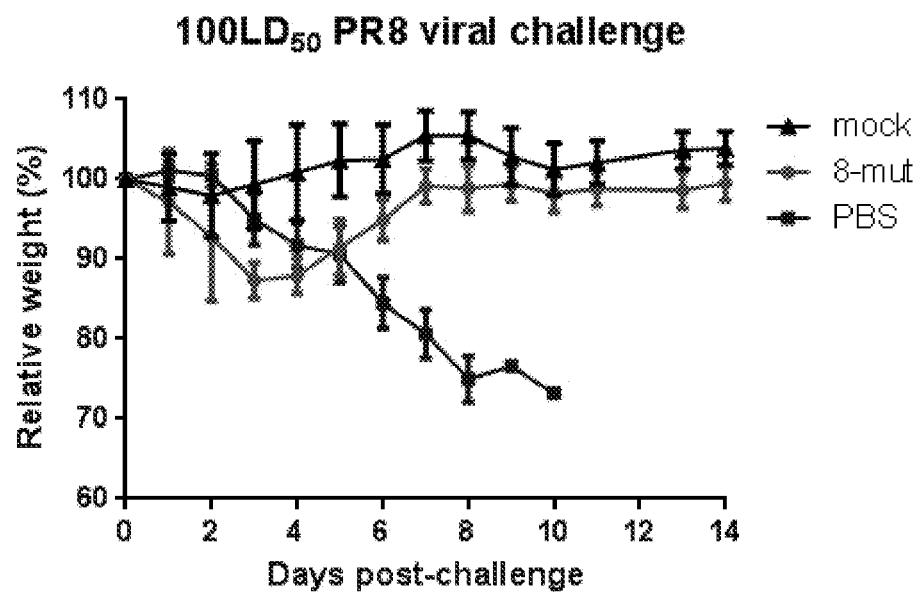
FIG. 5A is a graph showing a change in relative weight (%) at various days post-challenge of mice vaccinated intranasally with PBS (■) (mock vaccinated control) or $6.75 \times 10^5$ p.f.u. of 8-mut virus (●). At day 28 post-vaccination, mice were challenged with A/PR/8/34 ($100LD_{50}$; ~$2.1 \times 10^4$ p.f.u.) virus or mock control. Body weights of 6 mice were monitored for 14 days and data represent means±SD.
Figure 5B:
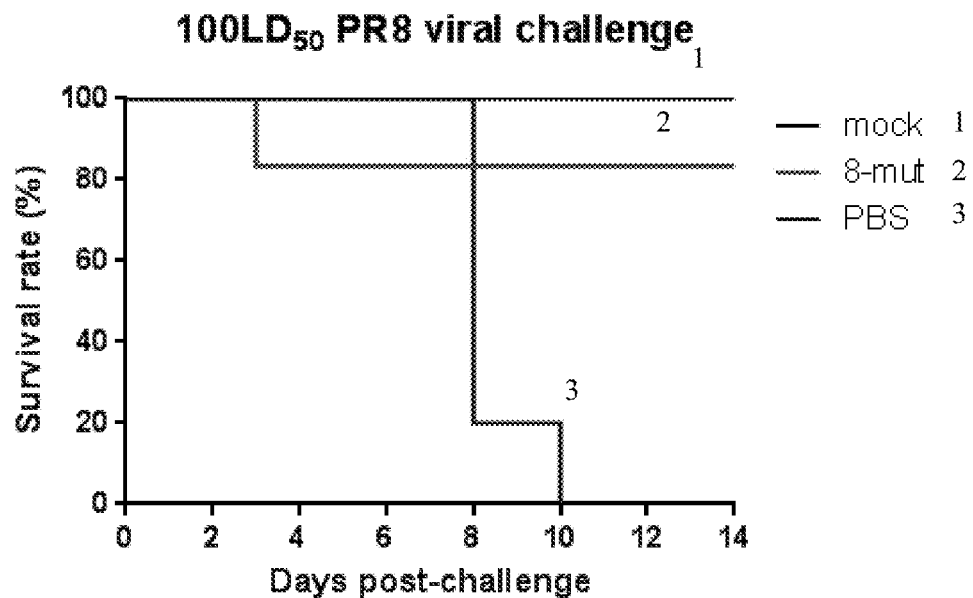
FIG. 5B shows the survival rate after challenge by A/PR/8/34 virus (mock, 1, 8-mut, 2, and PBS, 3). Group 1 is mock control. Mice are PBS vaccinated and challenged with PBS (mock). Group 2 is 8-mut vaccinated and challenged with PR8 virus. Group 3 is PBS vaccinated and challenged with PR8 virus.

A heterologous challenge (i.e. infected virus of different genetic background) in vaccinated mice was also conducted. Mice were vaccinated as described above. Mice were challenged with a highly lethal virus strain (A/PR/8/1934; H1N1) at an extremely high lethal dose (100 $LD_{50}$). All the mock-vaccinated control mice reached the humane experimental endpoint (>25% weight loss) and euthanized. By contrast, only 1 out of the 6 vaccinated mice died from the challenge (FIGS. 5A and 5B). The 8-mut was capable of inducing protective effects against infection caused by a heterologous virus. Therefore, the 8-mut virus was able to generate a heterosubtypic immune protection in the host.

Figures 6, 7A:
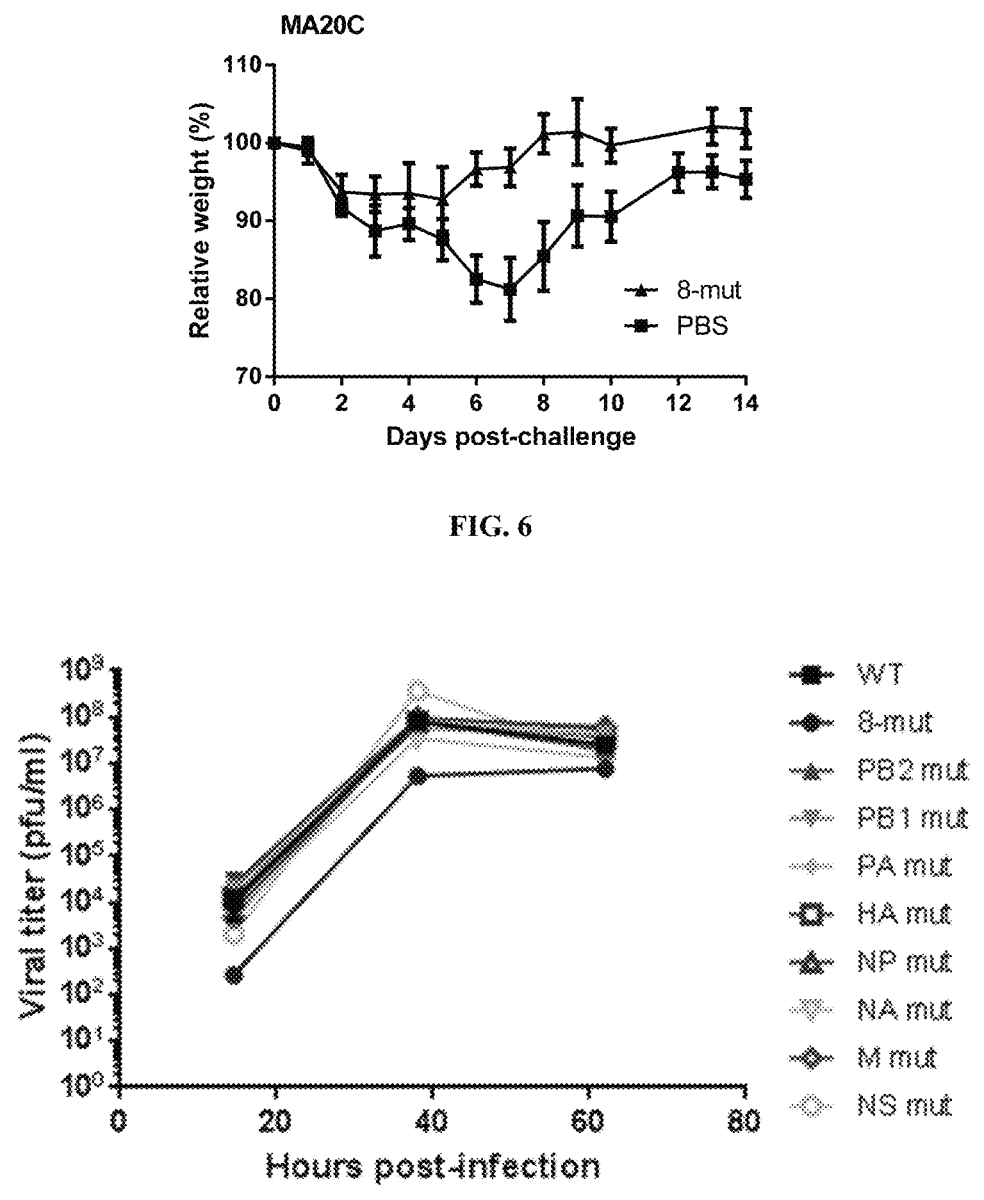

A heterologous challenge with a virus of different viral subtype in vaccinated mice was also performed. The mice were vaccinated with the 8-mut virus as described above (subtype H1N1, see Example 1). The mice were then challenged with $6.71 \times 10^5$ PFU of MA20C virus (mouse-adapted A/HK/68; subtype H3N2) 28 days post-vaccination. Body weights of 6 mice were monitored for 14 days. Vaccinated mice had less weight loss and earlier recovery (FIG. 6). Data represent mean±SD. * indicates p-value <0.05, ** indicates p-value <0.001.

Mice vaccinated with the 8-mut were be protected from H3N2 infections (FIG. 6), indicating that codon bias mutants can induce heterosubtypic protection. These results show that the 8-mut virus can induce protective effects against a homologous/heterologous virus challenge.

These broadly reactive vaccine-induced responses demonstrate that the disclosed strategy and methods can be used for producing vaccine capable of producing broad protective immunity.

Example 4. The Level of Virus Attenuation can be Manipulated

To exclude the possibility that the above virus attenuation was solely caused by one of the mutated viral segments, viruses with different combinations of wild-type and mutated segments (Table 8) were rescued and their replication kinetics in MDCK cells were studied.

Figure 7B:
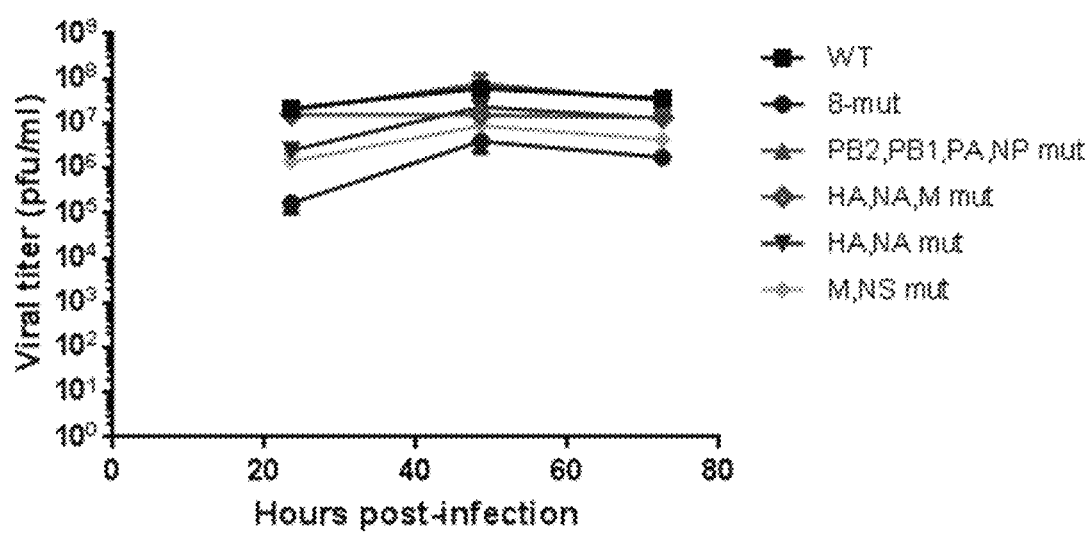

There was no significant difference between the growth of WT virus and viruses with 1 mutated segment (FIG. 7A). Viruses carrying a few mutated segments (e.g. HA/NA/M and M/NS) were found to have moderate growth attenuation, but their replication rates were still significantly higher than the one of 8-mut (FIG. 7B). In addition, mutants with 1-4 mutated viral segments were all found to have plaque sizes similar to those of WT virus. Altogether, these results indicated that the attenuation of 8-mut in mammalian cells was caused by the introduction of multiple mutated viral segments. More importantly, these results further indicated that the level of virus attenuation can be manipulated by introducing different number of mutated segments in the viral genome.

Example 5. The 8-Mut Virus as a Master-Virus for Vaccine Production

Materials and Methods

In order to achieve a high viral yield in eggs, wild-type seasonal influenza viruses are often reassorted with a master strain to generate vaccine strains for commercial vaccine productions (i.e. HA and NA segments derived from a seasonal strain and PB2, PB1, PA, NP, M and NS segments derived from a master strain). To determine whether the 8-mut virus has a potential to be used as master strain for making vaccine strain, recombinant viruses with their HA and NA segments derived from other influenza A viruses (H1N1: A/PR/8/1934; H3N2: A/HK/1/1968) and all the other segments from the 8-mut virus (i.e. PB2, PB1, PA, NP, M and NS segments) were generated as described in Example 1.

Results

Figure 8A:
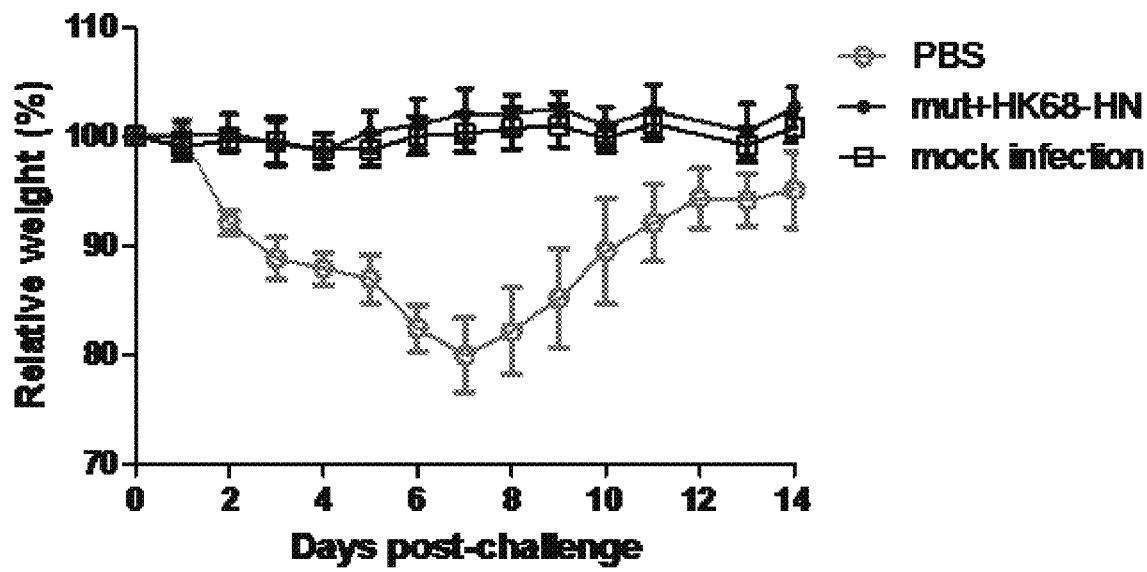
FIG. 8A is a graph showing a change in relative weight (%) of mice at different days post-challenge with a recombinant 8-mut+HK68-HN virus. A recombinant virus (mut+HK68-HN) with hemagglutinin (HA) and neuraminidase (NA) gene segments of wild-type A/HK/1/68 virus (subtype H3N2) and all the internal gene segments of the 8-mut virus (8-mut of A/Brisbane/57/07 virus, subtype H1N1) was made. Mice were treated with PBS and a H3N2 codon bias mutant ($1 \times 10^5$ p.f.u./dose) at day 0. Vaccinated mice were challenged with wild-type H3N2 virus or mock infection at day 28 post-infection. Group 1 is mock infection. Mice are PBS vaccinated and challenged with PBS (mock). Group 2 is mut+HK68-HN vaccinated and challenged with wild-type H3N2 virus. Group 3 is PBS vaccinated and challenged with wild-type H3N2 virus.
Figure 8B:
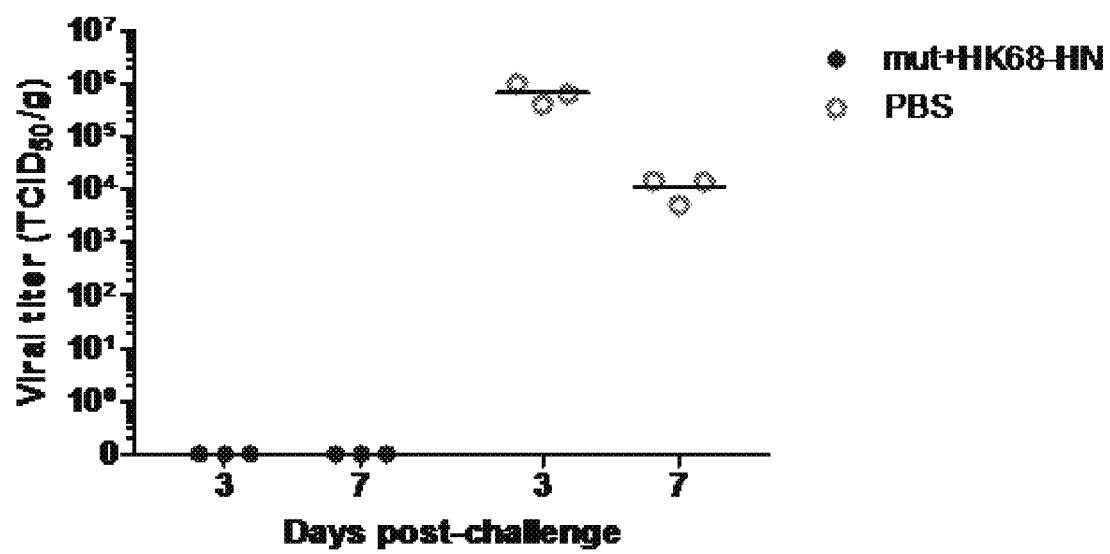
FIG. 8B is a graph showing lung viral titer ($TCID_{50}$/g) in mice at 3 days or 7 days post-challenge.

Both of the resultant recombinant viruses could achieve good viral yields in eggs and their yields are comparable to those of their corresponding controls at 48 hour post-infection (Table 13). More importantly, all of these recombinant mutants were found to be attenuated in mammalian cells. Such attenuation in mammalian cells, however, was not observed in the controls. Mice vaccinated with mut+ HK68-HN virus were completely protected from challenged with mouse-adapted A/HK/1/1968 virus (FIGS. 8A and 8B). These results demonstrated that our strategy might able to generate master viral strains for vaccine productions.

TABLE 13

Viral titer of infected MDCK cells and eggs with recombinant viruses coding genes from the same viral subtype (mut + PR8-HN) or different viral subtypes (mut + HK68-HN).

| Subtype | Mutant | Origin of PB2, PB1, PA, NP, M and NS segments | Origin of HA and NA segments | Titre (MDCK)* | Titre (Egg)* |
|---|---|---|---|---|---|
| H1N1 | Control | WT H1N1 (Brisbane/07) | A/PR/8/34 (H1N1) | 9.50E+06 | 2.40E+07 |
|  | Mut + PR8 HN | 8-mut (Brisbane/07) | A/PR/8/34 (H1N1) | 1.90E+03 | 7.40E+06 |
| H3N2 | Control | WT H1N1(Brisbane/07) | A/HK/1/68 (H3N2) | 6.90E+06 | 5.90E+06 |
|  | Mut + HK68 HN | 8-mut (Brisbane/07) | A/HK/1/68 (H3N2) | 4.20E+04 | 4.60E+06 |

*Viral titers were determined at 48 hour post-infection.

Figure 9A:
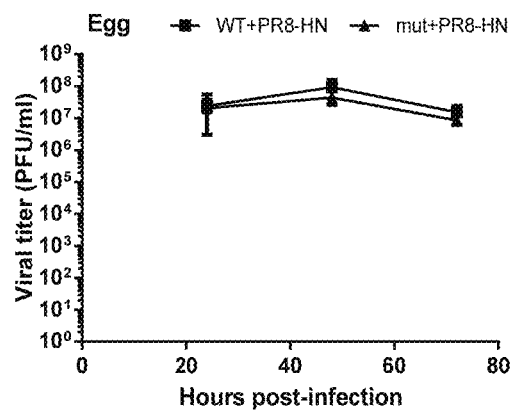
FIGS. 9A-9C are graphs showing growth kinetics of a recombinant virus with internal genes derived from the Brisbane/07 virus (subtype H1N1), and the surface glycoproteins HA and NA derived from the A/PR/8/34 virus (subtype H1N1) (WT+PR8-HN, (■)) and a recombinant virus with internal genes derived from the 8-mut and the surface glycoproteins HA and NA derived from the wild type PR8 virus (Mut+PR8 HN, (▲)). The growth kinetics were measured in viral titer (PFU/ml) as a function of time (hours post-infection). The embryonated eggs were infected with 100 PFU (FIG. 9A); the A549 cells were infected at 0.01 m.o.i.
Figure 9B:
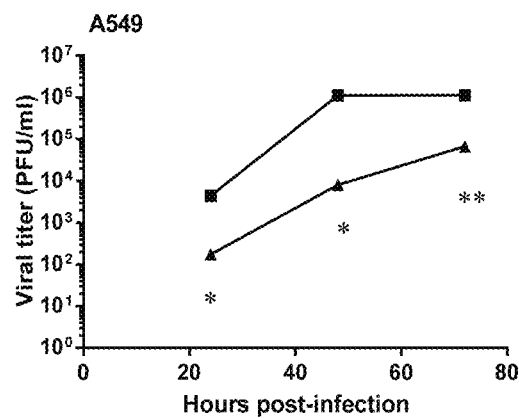
Figure 9C:
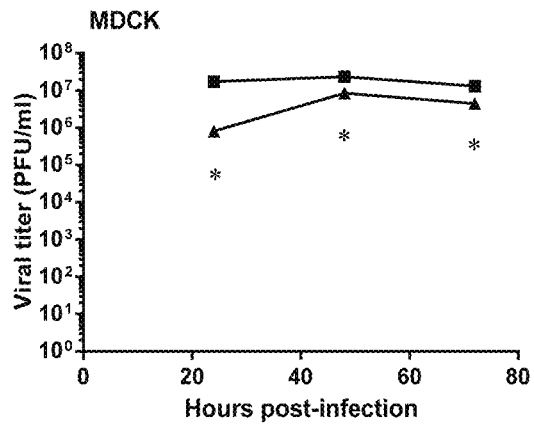
Figure 10:
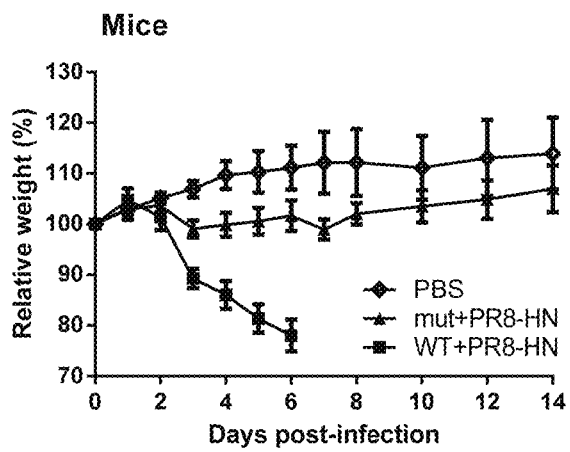
FIG. 10 is a graph showing the change in the relative weight (%) of mice over days post-infection with WT+PR8-HN (■), Mut+PR8 HN (▲), or PBS (●). Groups of 6

The growth rate of the Mut+PR8 HN mutant was attenuated in mammalian systems (FIGS. 9B and 9C). The virus was significantly attenuated in human A549 cells (FIG. 9B), and slightly attenuated in MDCK (canine kidney) cells (FIG. 9C). By contrast, this mutant was not attenuated in egg (FIG. 9A). The Mut+PR8 HN mutant was also significantly attenuated in mice (FIG. 10).

The growth rate of the Mut+HK68 HN was tested in human A549 cells and eggs. This mutant was much attenuated in mammalian cells (FIGS. 11A and 11B).

Example 6. Construction of an 8-Mut A/PR/8/34 Influenza Virus with Avian Codon Usage Bias Materials and Methods Using the approach described in Example 1, a codon bias mutant of A/PR/8/34 virus was generated (SEQ ID NOs: 17-32, and Table 14).

Results

This virus is a well-known master strain for vaccine production. The yield of this mutant in eggs was found to be identical to the wild-type level (FIG. 12). In addition, the mutant was confirmed to be attenuated in mice (FIG. 13A). The pathogenicity of the wild type A/PR/8/34 (PR8 WT) virus and its codon bias mutant (PR8 mut) was tested. Mice infected with 100 PFU/dose of the PR8 mut recovered from the infection, while those infected with the same dose of A/PR/8/34 wild type virus did not (FIG. 13B).

TABLE 14

Construction of A/PR/8/34 influenza virus with avian codon usage bias.

| Segment | No. of mutations (Nucleotides)[a] | No. of mutations (Codon)[b] |
|---|---|---|
| PB2 | 49 (2.09%) | 42 (5.53%) |
| PB1 | 71 (3.03%) | 68 (8.98%) |
| PA | 65 (2.91%) | 60 (8.38%) |
| HA | 40 (2.25%) | 35 (6.19%) |
| NP | 47 (3.00%) | 41 (8.23%) |
| NA | 49 (3.47%) | 46 (9.79%) |
| M | 23 (2.24%) | 23 (9.13%) |
| NS | 10 (1.12%) | 10 (4.35%) |
| Total | 354 (2.61%) | 325 (7.65%) |

[a] Percentages were calculated by dividing the number of nucleotide mutations by the full length of the respective segment.
[b] Percentages were calculated by dividing the number of codon mutations by the number of amino acids of the corresponding protein. For M and NS segments, the M2, and NS2 proteins were excluded in the calculations, as no mutations were introduced to those regions.

FIGS. 14A and 14B demonstrate that mice vaccinated with the avian codon usage bias mutant of the wild-type A/PR/8/34 virus (PR8 mut) were protected from 10× the lethal dose of the wild-type A/PR/8/34 virus.

These results demonstrate (1) the feasibility of using the avian codon usage bias to generate attenuated viruses with different genetic backgrounds and (2) the use of A/PR/8/34 mutant as a master strain for vaccine production.

Example 7. The Mutated A/PR/8/34 Influenza Virus with Avian Codon Usage Bias can Form a Master Strain for Vaccinations Materials and Methods The methods are as described in Examples 1 and 5.

Results

A recombinant virus was generated by using all the internal genes of the mutated A/PR/8/34 influenza virus with avian codon usage bias (PB2, PB1, PA, NP, M and NS) and the surface glycoprotein genes (HA and NA) of the highly pathogenic A/Indonesia/5/2005 (H5N1). The virus was successfully rescued. This recombinant virus can serve as a master strain for vaccinating against highly pathogenic viral subtypes.

Overall, the Examples show generation of at least two different 8-mut viruses capable of producing both homosubtypic and heterosubtypic immune protection when the viruses are used as vaccines. These results are summarized in Table 15 below.

These results, together with those from the codon bias mutant of A/Brisbane/59/2007, demonstrate the features and usefulness of the approach described herein to generate live-attenuated virus strains and master strains for vaccine production.

TABLE 15

Mutated viruses produced and the immune protection observed when the viruses were used as vaccines in mice.

| Subtype | Mutant Virus | Segments mutated | Wild type segments | Immune Protection | Reference |
|---|---|---|---|---|---|
| H1N1 | 8-mut (A/Brisbane/59/2007) | PB2, PB1, PA, HA, NP, NA, M, NS | | Homosubtypic | FIGS. 2A 2B, 5A and 5B |
| | | | | Heterosubtypic | FIG. 6 |
| H1N1-H1N1 | Recombinant: 8-mut (A/Brisbane/59/2007) and wild type A/PR/8/34 (Mut + PR8-HN) | PB2, PB1, PA, NP, M, and NS | HA and NA of wild type A/PR/8/34 | Homosubtypic | |
| H1N1-H3N2 | Recombinant: 8-mut (A/Brisbane/59/2007) and wild type A/HK/1/68 (Mut + HK68-HN) | PB2, PB1, PA, NP, M, and NS | HA and NA of wild type A/HK/1/68 | Heterosubtypic | FIG. 8A |
| H1N1 | 8-mut (A/PR/8/34) | PB2, PB1, PA, HA, NP, NA, M, NS | | Homosubtypic | FIGS. 14A and 14B |
| H1N1-H5N1 | Recombinant: 8-mut (A/PR/8/34) and wild type A/Indonesia/5/2005 (Mut + I5-HN) | PB2, PB1, PA, NP, M, and NS | HA and NA of wild type A/Indonesia/5/2005 | Heterosubtypic | |

The SEQ ID NOS 1-32 referenced herein are sequences for the following wild type (WT) and mutated viral segments:
SEQ ID NO:1—A/Brisbane/59/2007 WT PB2
SEQ ID NO:2—A/Brisbane/59/2007 mutated PB2
SEQ ID NO:3—A/Brisbane/59/2007 WT PB1
SEQ ID NO:4—A/Brisbane/59/2007 mutated PB1
SEQ ID NO:5—A/Brisbane/59/2007 WT PA
SEQ ID NO:6—A/Brisbane/59/2007 mutated PA
SEQ ID NO:7—A/Brisbane/59/2007 WT HA
SEQ ID NO:8—A/Brisbane/59/2007 mutated HA
SEQ ID NO:9—A/Brisbane/59/2007 WT NP
SEQ ID NO:10—A/Brisbane/59/2007 mutated NP
SEQ ID NO:11—A/Brisbane/59/2007 WT NA
SEQ ID NO:12—A/Brisbane/59/2007 mutated NA
SEQ ID NO:13—A/Brisbane/59/2007 WT M
SEQ ID NO:14—A/Brisbane/59/2007 mutated M
SEQ ID NO:15—A/Brisbane/59/2007 WT NS
SEQ ID NO:16—A/Brisbane/59/2007 mutated NS
SEQ ID NO:17—A/Puerto Rico/8/34 WT PB2
SEQ ID NO:18—A/Puerto Rico/8/34 mutated PB2
SEQ ID NO:19—A/Puerto Rico/8/34 WT PB1
SEQ ID NO:20—A/Puerto Rico/8/34 mutated PB1
SEQ ID NO:21—A/Puerto Rico/8/34 WT PA
SEQ ID NO:22—A/Puerto Rico/8/34 mutated PA
SEQ ID NO:23—A/Puerto Rico/8/34 WT HA
SEQ ID NO:24—A/Puerto Rico/8/34 mutated HA
SEQ ID NO:25—A/Puerto Rico/8/34 WT NP
SEQ ID NO:26—A/Puerto Rico/8/34 mutated NP
SEQ ID NO:27—A/Puerto Rico/8/34 WT NA
SEQ ID NO:28—A/Puerto Rico/8/34 mutated NA
SEQ ID NO:29—A/Puerto Rico/8/34 WT M
SEQ ID NO:30—A/Puerto Rico/8/34 mutated M
SEQ ID NO:31—A/Puerto Rico/8/34 WT NS
SEQ ID NO:32—A/Puerto Rico/8/34 mutated NS It is understood that the disclosed method and compositions are not limited to the particular methodology, protocols, and reagents described as these may vary. It is also to be understood that the terminology used herein is for the purpose of describing particular forms only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a codon" includes a plurality of such codons, reference to "the live-attenuated" is a reference to one or more live-attenuated viruses and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, to "about" another particular value, or both. When such a range is expressed, also specifically contemplated and considered disclosed is the range from the one particular value, to the other particular value, or both, unless the context specifically indicates otherwise. Similarly, when values are expressed as approximations, by use of the antecedent "about," it will be understood that the particular value forms another, specifically contemplated form that should be considered disclosed unless the context specifically indicates otherwise. It will be further understood that the endpoints of each of the ranges are significant both in relation to the other endpoint, and independently of the other endpoint unless the context specifically indicates otherwise.

It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these forms are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. may include numerous options and alternatives, this should not be construed as, and is not an admission that, such options and alternatives are equivalent to each other or, in particular, are obvious alternatives. Thus, for example, a list of different mutated codons does not indicate that the listed mutated codons are obvious one to the other, nor is it an admission of equivalence or obviousness.

Those skilled in the art will recognize, or be able to ascertain using no more than routine experimentation, many equivalents to the specific forms of the method and compositions described herein. Such equivalents are intended to be encompassed by the following claims.

We claim:

1. A live-attenuated virus comprising a genome genetically engineered from a wild type virus to have mutated codons having an avian viral codon usage bias, the mutated codons having an avian viral codon usage bias present at conserved sites at the amino acid level and absent from genomic regions involving packaging or splicing, or overlapping reading frames encoding multiple proteins.

2. The live-attenuated virus of claim 1, wherein the mutated codons having an avian viral codon usage bias are synonymous substitutions.

3. The live-attenuated virus of claim 1, wherein the mutated codons having an avian viral codon usage bias are silent mutations.

4. The live-attenuated virus of claim 1, wherein the live-attenuated virus does not have any amino acid mutations relative to the wild type virus.

5. The live-attenuated virus of claim 1, wherein the mutated codons having an avian viral codon usage bias are randomly but evenly distributed in the genome excluding the genomic regions involving packaging or splicing, or overlapping reading frames encoding multiple proteins.

6. The live-attenuated virus of claim 1, wherein the mutated codons having an avian viral codon usage bias are present in at least one gene, in at least two genes, in at least three genes, in at least four genes, in at least five genes, in at least six genes, in at least seven genes, or in at least eight genes.

7. The live-attenuated virus of claim 1, wherein the live-attenuated virus has slower replication in a mammalian host but not in an avian host, when compared to the replication of the wild type virus in the respective hosts.

8. The live-attenuated virus of claim 1, wherein the live-attenuated virus produces antibody-mediated immunity similar to that produced by the wild type virus.

9. The live-attenuated virus of claim 1, wherein the live-attenuated virus produces cell-mediated immunity similar to that produced by the wild type virus.

10. The live-attenuated virus of claim 1, wherein the live-attenuated virus produces antibody-mediated immunity and cell-mediated immunity similar to that produced by the wild type virus.

11. The live-attenuated virus of claim 1, wherein the live-attenuated virus replicates at substantially the same rate at 33° C. and at 37° C.

12. The live-attenuated virus of claim 1, wherein the live-attenuated virus produces a protective immune response in a mammalian host against homologous and heterologous viral challenges.

13. The live-attenuated virus of claim 1, wherein the wild type virus is influenza type A or influenza type B.

14. The live-attenuated virus of claim 13, wherein the live-attenuated virus is 8-mut.

15. The live-attenuated virus of claim 1, wherein the live-attenuated virus does not have any temperature-sensitive mutations relative to the wild type virus.

16. The live-attenuated virus of claim 1, wherein the live-attenuated virus is a master strain.

17. A vaccine composition comprising the live-attenuated virus of claim 1.

18. The vaccine composition of claim 17, further comprising a carrier.

19. The vaccine composition of claim 18, further comprising an adjuvant.

20. The live-attenuated virus of claim 1, wherein the wild type virus is a mammalian virus.

21. The live-attenuated virus of claim 1, wherein the wild type virus is a mammalian influenza virus.

22. The live-attenuated virus of claim 1, wherein the wild type virus is a human virus.

23. The live-attenuated virus of claim 1, wherein the wild type virus is a human influenza virus.

* * * * *

SEQUENCE LISTING

```
<160> NUMBER OF SEQ ID NOS: 32

<210> SEQ ID NO 1
<211> LENGTH: 2341
<212> TYPE: DNA
<213> ORGANISM: Influenza virus

<400> SEQUENCE: 1
agcaaaagca ggtcaattat attcaatatg gaaagaataa aagagctaag gaatttgatg     60
tcacaatctc gcactcgcga gatacttacc aaaactactg tagaccacat ggccataatc    120
aagaaataca catcaggaag acaggagaaa aacccatcac ttaggatgaa atggatgatg    180
gcaatgaaat acccaattac agctgataaa aggataacgg aaatgattcc tgaaagaaat    240
gagcatggac agacattatg gagtaaggtg aatgatgccg gatcagaccg agtgatggta    300
tcacccctgg ctgtgacatg gtggaacaga aatggaccag tggcaagtac tattcactat    360
ccaaaaatct acaaaactta ctttgaaaag gttgaaaggt taaaacaagg aacctttggc    420
cctgtacact ttagaaacca agtcaaaata cgccgaagag tcgacataaa tcctggtcat    480
gcagacctca gcgccaagga ggcacaggat gtaattatgg aagttgtttt ccctaatgaa    540
gtaggagcca gaatactaac atcagaatcg caattaacga taaccaagga gaaaaaagaa    600
gaactccaga attgcaaaat ttcccctttg atggttgcat acatgttaga gagggaactt    660
gtccgcaaaa caagatttct cccggttgca ggtggaacaa gcagtgtgta cattgaagtt    720
ttgcatttaa cacaggggac atgctgggag cagatgtaca ctccaggtgg ggaggtgagg    780
aatgatgatg ttgatcaaag cctaattatt gctgctagga acatagtgag aagagctgca    840
gtatcagcag atccactagc atctttatta gaaatgtgcc atagcacaca gattggtgga    900
acaaggatgg tggatattct caggcaaaat ccaacagaag aacaagctgt ggatatatgc    960
aaggcagcaa tggggctgag aatcagctca tccttcagtt ttggcggatt cacatttaag   1020
agaacaagtg gatcatcagt caaaagggag gaagaagtgc tcacgggcaa tctgcaaaca   1080
ttgaaactaa ccgtgcatga gggatatgaa gagttcacaa tggttgggaa aagggcaaca   1140
```

```
gctatactca gaaaagcaac caggagattg attcaactaa tagtgagtgg aagagacgaa    1200
caatcaatag tcgaagcaat agttgtagca atggtattct cacaagaaga ttgcatggta    1260
aaagcagtta gaggtgatct gaatttcgtt aatagagcga atcagcggtt gaatcccatg    1320
catcaactat tgagacattt tcagaaggat gctaaagtac ttttcttaaa ttggggagtt    1380
gaacctattg acaatgtgat gggaatgatt gggatattac ctgatatgac tccaagtacc    1440
gagatgtcaa tgagaggagt gagagtcagc aaaatgggtg tagatgaata ctccaatgct    1500
gaaagggtag tggtaagcat tgaccgtttt ttgagagtcc gggaccaaag aggaaatgta    1560
ctactgtctc cagaggaagt aagtgaaaca caagggacag agaaactgac aataacttac    1620
tcttcatcaa tgatgtggga gattaatggc cctgagtcag tcttgatcaa tacctatcag    1680
tggatcatca gaaactggga gactgttaaa attcagtggt ctcagaatcc tacgatgctg    1740
tacaataaaa tggaatttga accatttcag tctctagtcc ccaaggccat tagaggccaa    1800
tacagtgggt tgttagaac tctattccaa caaatgaggg atgtgcttgg acttttgac    1860 acaactcaga taataaaact tcttcccttt gcagccgctc ctccaaagca aagcagaatg    1920
caattctcgt cattaactgt gaatgtgagg ggatcaggaa tgagaatact tgtgaggggt    1980
aattctccag tattcaacta caacaagact accaagagac tcacagtcct cggaaaggat    2040
gctggcactt taactgaaga cccagatgaa ggcacagctg gagtggaatc tgcggttcta    2100 agggattcc tcattttagg caagaagat agaagatatg gccagcatt aagcatcaat    2160 gaattgagca accttgcgaa aggggaaaaa gctaatgtgc taattgggca aggggatgta    2220
gtgttggtaa tgaaacgaaa acgggactct agcatactta ctgacagcca gacagcgacc    2280
aaaagaattc ggatggccat caattaattt cgaataattt aaaaacgacc ttgtttctac    2340
t                                                                    2341
```

<210> SEQ ID NO 2
<211> LENGTH: 2341
<212> TYPE: DNA
<213> ORGANISM: Influenza virus

<400> SEQUENCE: 2

```
agcaaaagca ggtcaattat attcaatatg gaaagaataa aagagctaag gaatttgatg     60
tcgcaatctc gcactcgcga gatacttacc aaaaactactg tggaccacat ggccataatc    120
aagaaatata catcaggaag acaggagaag aacccatcac ttaggatgaa atggatgatg    180
gcaatgaaat acccaatcac agctgataaa aggataacgg agatgattcc tgaaagaaac    240
gagcatggac agacattgtg gagtaaggtg aatgatgccg atcagaccg agtgatggta    300 tcacccctgg ctgtgacatg gtggaacaga atggaccag tggcaagtac tattcactat    360
ccaaagatct acaaaaccta cttcgaaaag gttgaaaggt taaaacaagg aacctttggc    420
cccgtacact ttagaaaacca agtcaaaata cgccgaaggg tcgacataaa tcctggtcat    480
gcagacctca gcgccaagga ggcacaggat gtaatcatgg aagttgtttt ccctaacgaa    540
gtaggagcca gaatactaac atcagagtcg caattgacga taaccaagga gaaaaaagaa    600
gaactccaga attgcaagat tcccccttg atggttgcat atatgttaga gagggaactg    660
gtccgcaaaa caagattcct cccggttca ggtggaacaa gcagtgtgta cattgaagtt    720
ttgcatttga cacaggggac atgctgggag cagatgtaca caccaggtgg ggaggtgagg    780
aatgatgatg ttgaccaaag cctaattatt gctgctagga caatagtgag aagagcagca    840
gtatcagcag atcCactggc atcttattg gaaatgtgcc atagcacaca gattggtgga    900
```

```
acaaggatgg tggatatcct caggcaaaat ccaacagagg aacaagctgt ggatatatgc    960
aaggcagcaa tggggctgag aatcagctca tccttcagtt ttggcggatt cacatttaag   1020
agaacaagtg gatcgtcagt caaaagggag aagaagtgc tcacgggcaa cctgcaaaca    1080
```
(Note: line "agaacaagtg..." as printed)
```
ttgaaactaa ccgtgcatga gggatatgaa gagttcacaa tggttgggaa agggcaaca    1140
gctatactca gaaaggcaac caggagattg attcaactaa tagtgagtgg aagagacgag   1200
caatcaatag tcgaagcaat agttgtagca atggtattct cacaagaaga ctgcatggta   1260
aaagcagtta gaggtgatct gaatttcgtt aatagagcaa atcagcggtt gaaccccatg   1320
catcaactat tgagacattt tcagaaggat gctaaagtgc ttttcttaaa ttggggagtt   1380
gaacctattg acaatgtgat gggaatgatt gggatattgc ctgacatgac tccaagtacc   1440
gagatgtcaa tgaggggagt gagagtcagc aaaatgggtg tagatgaata ctccaatgct   1500
gaaagggtag tggtaagcat tgaccgtttc ttgagagtcc gagaccaaag aggaaacgta   1560
ctactgtctc cagaggaggt aagtgaaaca caagggacag agaaactgac aataacttat   1620
tcttcatcaa tgatgtggga gatcaatggc cctgagtcag tcttgatcaa tacctatcag   1680
tggatcatca gaaactggga gactgttaag attcagtggt ctcagaatcc cacgatgctg   1740
tacaacaaaa tggaatttga accatttcag tctctggtcc ccaaggccat tagaggccaa   1800
tacagtgggt tgttagaac gctattccaa caaatgaggg atgtgctggg gactttcgac   1860
acaactcaga taataaaact tcttcccttt gcagccgctc ctccaaagca aagcagaatg   1920
caattctcgt ccttaacagt gaatgtgagg ggatcaggaa tgagaatact tgtgaggggt   1980
aattctccag tattcaacta taacaagact accaagagac tcacagtcct cggaaaggat   2040
gctggcactt tgactgaaga cccagatgaa ggcacagctg gagtggagtc tgcggttcta   2100
aggggattcc tcattttagg caaagaagac agaagatatg ggccagcatt aagcatcaac   2160
gaattgagca accttgcgaa aggggaaaag gctaatgtgc taatagggca aggggatgta   2220
gtgttggtaa tgaaacgaaa acgggactct agcatactta ctgacagcca gacagcgacc   2280
aaaagaattc ggatggccat caattaattt cgaataattt aaaaacgacc ttgtttctac   2340
t                                                                  2341
```

<210> SEQ ID NO 3
<211> LENGTH: 2341
<212> TYPE: DNA
<213> ORGANISM: Influenza virus

<400> SEQUENCE: 3

```
agcgaaagca ggcaaaccat ttgaatggat gtcaatccga cattactttt cttaaaagtg    60
ccagcacaaa atgctataag cacaactttt cctatactg gtgaccctcc ttacagccat    120
gggacaggaa caggatacac catggataca gtcaacagga cacaccagta ctcagaaaga    180
ggaagatgga caaaaaatac cgaaactgga gcaccgcaac ttaacccaat tgatggtcca    240
ctaccggaag acaatgaacc aagtggctat gcccaaacag attgtgtatt agaagcaatg    300
gctttccttg aagaatccca tcccggtatc tttgaaaact cttgtattga acaatggag    360
gttgttcagc aaacaagggt ggacaaactg acacaaggca gacagaccta tgactggact    420
ctaaatagga accagcctgc tgccacagca ttggcaaaca ctatagaagt attcagatca    480
aacggcctca tagcaaatga atctgggagg ctaatagact tccttaaaga tgtaatggag    540
tcgatggaca gaggcgaagt agaggtcaca actcattttc aaagaaagag gagagtgaga    600
```

| | |
|---|---|
| gacaatgtaa ctaaaaaaat ggtgacccaa agaacaatag gcaaaagaa acataaatta | 660 |
| gacaaaagaa gttacctaat tagggcatta accctgaaca caatgaccaa agatgctgag | 720 |
| aggggaaac taaaacgcag agcaattgca accccaggaa tgcaaataag ggggtttgta | 780 |
| tactttgttg agacactggc aagaagcata tgtgaaaagc ttgaacaatc aggattgcca | 840 |
| gttggaggaa atgagaagaa agcaaagtta gcaaatgttg taaggaagat gatgaccaac | 900 |
| tcccaggaca ctgaaatttc tttcaccata accggagata cacaaaatg gaacgagaat | 960 |
| caaacccta gaatgttctt ggccatgatc acatatataa ccaaaaatca gcctgaatgg | 1020 |
| ttcagaaatg ttctaagtat tgctccaata atgttttcaa acaagatggc gagactaggt | 1080 |
| aaggggtaca tgtttgaaag caagagtatg aaactgagaa ctcaaatacc tgcagagatg | 1140 |
| ctagctaaca tagatttgaa atatttcaat gattcaacta aaagaaaat tgaaaaaatc | 1200 |
| cgaccattat aatagatgg aactgcatca ttgagtcctg gaatgatgat gggcatgttc | 1260 |
| aatatgttga gcaccgtctt gggcgtctcc attctgaatc ttgggcaaaa gagatacacc | 1320 |
| aagactactt actggtggga tggtcttcaa tcgtctgatg attttgcttt gattgtgaat | 1380 |
| gcacccaact atgcaggaat tcaagctgga gttgacaggt tttatcgaac ctgtaagctg | 1440 |
| ctcggaatta atatgagcaa aaagaagtct tacataaaca gaacaggtac ctttgaattc | 1500 |
| acgagcttt tctatcgtta tgggtttgtt gccaatttca gcatggagct tcctagtttt | 1560 |
| ggggtgtctg gggtcaatga atctgcagac atgagtattg gagtcactgt catcaaaaac | 1620 |
| aatatgataa acaatgacct tggcccagca actgctcaaa tggcccttca gttatttata | 1680 |
| aaagattaca ggtacactta tcgatgccac cgaggtgaca cacaaataca aacccggaga | 1740 |
| tcatttgaga taaagaaact atgggaccaa accgctcaa agctgggct gttggtctct | 1800 |
| gatggaggcc ccaatttata taacattaga aatctccata ttcctgaagt ttgcttgaaa | 1860 |
| tgggagttga tggatgagga ttaccagggg cgtttatgca acccattaaa cccgtttgtc | 1920 |
| agccataaag agattgaatc agtgaacaat gcagtgataa tgccggcaca tggtccagcc | 1980 |
| aaaaatatgg agtatgacgc tgttgcaaca acacactcct gggtccccaa aagaaatcga | 2040 |
| tccatttga acacgagcca aaggggata cttgaagatg agcaaatgta tcagaggtgc | 2100 |
| tgcaatttat ttgaaaaatt cttcccaagt agctcataca aagaccagt tggaatatcc | 2160 |
| agtatggtag aggctatggt ctcaagagcc cgaattgatg cacggattga tttcgaatct | 2220 |
| ggacggataa agaaagagga atttgctgag atcatgaaga tctgttccac cattgaagac | 2280 |
| ctcagacggc aaaaatgagg aatttggctt gtccttcatg aaaaaatgcc ttgtttctac | 2340 |
| t | 2341 |

<210> SEQ ID NO 4
<211> LENGTH: 2341
<212> TYPE: DNA
<213> ORGANISM: Influenza virus

<400> SEQUENCE: 4

| | |
|---|---|
| agcgaaagca ggcaaaccat ttgaatggat gtcaatccga cattactttt cttaaaagtg | 60 |
| ccagcacaaa atgctataag cacaactttc ccttatactg gtgaccctcc ttacagccat | 120 |
| gggacaggaa caggatacac catggataca gtcaacagga cacaccagta ctcagaaaga | 180 |
| ggaagatgga caaaaaatac cgaaactgga gcaccgcaac ttaacccaat tgatggtcca | 240 |
| ctaccggaag acaatgaacc aagtggctat gcccaaacag attgtgtatt agaagcaatg | 300 |
| gctttccttg aagaatccca tccggaatc tttgaaaact cttgtattga aacaatggag | 360 |

```
gttgttcagc aaacaagggt ggacaagctg acacaaggaa ggcagacata tgactggact    420
ctaaatagga accagcctgc tgccacagca ttggcaaaca aatagaagt attcagatca     480 aacggcctca tagcaaatga atcggggagg ctaatagact tccttaagga tgtaatggag   540
tcgatggaca gaggcgaagt agaggtcaca acacattttc aaaggaagag gagagtgaga   600
gacaatgtaa cgaaaaaaat ggtgacgcaa agaacaatag gaaaaagaa gcataaatta    660 gacaagagaa gttacctaat tagggcactc accctgaaca caatgacaaa agatgctgag   720
aggggaaaac taaagcgcag agcaatcgca accccaggaa tgcaaatcag ggggtttgta   780
tacttcgttg agacactggc aagaagcata tgtgaaaagc ttgaacaatc aggattgcca   840
gttggaggaa atgagaagaa agcgaagtta gcaaatgttg tgaggaagat gatgaccaac   900
tcccaggaca cggaaatttc tttcaccata acaggagata acacaaaatg gaacgagaat   960
caaaacccta gaatgttcct ggccatgatc acatatatca ccaaaaatca gcctgaatgg  1020
ttcagaaatg ttctaagcat tgctccaata atgttctcaa acaagatggc gagactaggt  1080
aaggggtaca tgttcgaaag caagagtatg aaactgagga ctcaaatacc tgcagagatg  1140
ctagctaaca tagatttgaa atatttcaat gattcaacaa aaagaaaat tgaaaaaatc    1200 cgaccattac tcatagatgg aactgcctca ttgagtcctg aatgatgat gggcatgttc   1260 aatatgttga gcacagtctt gggagtctcc attctgaatc ttgggcaaaa agatacacc   1320 aagacaactt actggtggga tggacttcaa tcgtctgatg attttgctct gattgtgaat   1380
gcacccaact atgcaggaat tcaagctgga gttgacaggt tttatcgaac gtgtaagctg   1440
ctcggaatca atatgagcaa gaagaagtct tacataaaca gaacaggtac ctttgaattc   1500
acgagctttt tctatcgtta tgggtttgtt gccaatttca gcatggagct tcctagcttt   1560
ggggtgtctg gggtcaatga aagcgcagac atgagtattg gagtcacagt catcaaaaac   1620
aatatgataa acaatgacct tggaccagca actgctcaaa tggcccttca gctctttata   1680
aaggattaca ggtacactta tcgctgccac cgaggagaca cacaaatcca aacccggaga   1740
tcattcgaga taaagaaact atgggaccaa acacgctcaa aagctggact gttggtctct   1800
gatggaggac ccaatctgta taacattaga aatctccata tccctgaagt ttgcttgaaa   1860
tgggagttga tggatgagga ttaccagggg cgtctgtgca acccattaaa cccgtttgtc   1920
agccataaag agattgaatc agtgaacaat gcagtgataa tgccggcaca tggaccagcc   1980
aagaatatgg agtatgacgc tgttgcaaca acacactcct gggtccccaa gagaaatcgg   2040
tccattctga cacgagcca agggggata cttgaagatg agcaaatgta tcagaggtgc    2100
tgcaatctgt ttgaaaagtt cttcccaagt agctcataca aaggccagt tggaatatcc   2160 agtatggtag aggctatggt ctcaagagcc cgaattgatg cgcggattga tttcgaatct   2220
ggacggataa agaaagagga atttgctgag atcatgaaga tctgttccac cattgaagac   2280
ctcagacggc aaaaatgagg aatttggctt gtccttcatg aaaaaatgcc ttgtttctac   2340
t                                                                  2341

<210> SEQ ID NO 5
<211> LENGTH: 2233
<212> TYPE: DNA
<213> ORGANISM: Influenza virus

<400> SEQUENCE: 5
agcaaaagca ggtactgatt cgaaatggaa gattttgtac gacaatgctt caatccgatg    60
```

-continued

| | |
|---|---|
| attgtcgagc ttgcagaaaa agcaatgaaa gagtatggag aggacctgaa atcgaaaca | 120 |
| aacaaatttg cagcaatatg cacccacttg gaagtgtgct tcatgtattc agattttcat | 180 |
| ttcatcaatg agcaaggcga atcaataata gtagagcctg aggacccaaa tgcactttta | 240 |
| aagcacagat ttgagataat agagggacga gatcgtacaa tggcatggac agttgtaaac | 300 |
| agtatttgca acaccacagg agctgagaaa ccaaagtttc tgccagatct gtatgattac | 360 |
| aaagagaata gattcatcga gattggagtg acaaggaggg aagttcacat atactatctg | 420 |
| gaaaaggcca acaaaattaa atctgagaag acacacattc acattttctc attcaccggc | 480 |
| gaagaaatgg ccacaaaggc cgattacact ctcgatgaag aaagcagagc taggattaaa | 540 |
| accagattgt tcaccataag acaagaaatg gcaagcagag gtctttggga ctcctttcgt | 600 |
| cagtccgaaa gaggcgaaga aacaattgaa gaaagatttg aaatcacagg acaatgcgc | 660 |
| aggctcgctg accaaagcct tccgccgaac ttctcctgca ttgagaattt tagagcctat | 720 |
| gtggatggat ttgaaccgaa cggctacatt gagggcaagc tttctcaaat gtccaaagaa | 780 |
| gtaaatgcta gaattgagcc tttttgaaa acaacacctc gaccaattag acttccgaat | 840 |
| ggccctcctt gttttcagcg gtcaaaattc ctgctgatgg attctttaaa attaagcatt | 900 |
| gaggatccaa atcatgaagg tgaggggata ccactatatg atgcaatcaa gtgtatgaga | 960 |
| acattctttg gatggaaaga acccactgtt gtcaagccac acgagaaggg aataaatccg | 1020 |
| aattatctgt tgtcgtggaa gcaagtattg gaagagctgc aggacattga gagtgaggag | 1080 |
| aggattccaa gaacaaaaaa catgaaaaaa actagtcagc taaagtgggc acttggtgag | 1140 |
| aacatggcac cagagaaggt ggattttgat gactgtaaag atataagcga tttgaagcaa | 1200 |
| tatgacagtg acgaacctga attaagatca ttttcaagtt ggatccagaa tgagttcaac | 1260 |
| aaggcatgcg agctgaccga ttcaatctgg atagagcttg atgagattgg agaagatgtg | 1320 |
| gctccgattg aacacattgc aagcatgaga aggaattact tcacagctga ggtgtcccat | 1380 |
| tgcagagcca cagaatatat aatgaagggg gtatacatta atactgcttt gctcaatgca | 1440 |
| tcctgtgcag caatggatga tttccaacta attcccatga taagcaaatg tagaactaaa | 1500 |
| gagggaagga gaaagaccaa tttgtacggc ttcatcgtaa aaggaagatc tcacttaagg | 1560 |
| aatgacaccg atgtggtaaa cttttgtgagc atggagtttt ccctcactga cccaagactt | 1620 |
| gagccacaca atgggagaa gtactgcgtt cttgagatag gagatatgct tctaaggagt | 1680 |
| gcaataggcc aagtgtcaag gcccatgttc ttgtatgtaa ggacaaatgg aacctcaaaa | 1740 |
| attaaaatga atggggaat ggagatgagg cgttgcctcc tccaatccct ccaacaaata | 1800 |
| gagagcatga ttgaagctga gtcctctgtc aaagagaaag acatgacaaa agagtttttt | 1860 |
| gagaataaat cagaaacatg gcccattgga gagtcaccaa aaggagtgga agaaggttcc | 1920 |
| attgggaaag tatgcaggac actgttggct aagtcagtat tcaatagcct gtatgcatct | 1980 |
| ccacaattag aaggattttc agctgagtca agaaagttgc tcctcattgt tcaggctctt | 2040 |
| agggacaatc tggaacctgg gaccttgat cttgggggc tatatgaagc aattgaggag | 2100 |
| tgcctgatta atgatccctg ggttttgctt aatgcttctt ggttcaactc cttcctaaca | 2160 |
| catgcattga gatagctgag gcaatgctac tatttgttat ccatactgtc caaaaagta | 2220 |
| ccttgtttct act | 2233 |

<210> SEQ ID NO 6
<211> LENGTH: 2233
<212> TYPE: DNA
<213> ORGANISM: Influenza virus

<400> SEQUENCE: 6

```
agcaaaagca ggtactgatt cgaaatggaa gattttgtac gacaatgctt caatccgatg      60
attgtcgagc ttgcagaaaa agcaatgaaa gagtatggag aagacctgaa atcgaaaca     120
aacaaattcg cagcaatatg cacccacttg gaagtgtgct tcatgtattc agattttcat    180
ttcatcaacg agcaaggcga atcaataata gtagagcctg aggacccaaa cgcacttcta    240
aagcacagat ttgaaataat agagggacga gatcgtacaa tggcatggac agttgtgaac    300
agtatttgca acaccactgg agctgagaaa ccaaagtttc tgccagatct gtatgattac    360
aaagaaaata gattcatcga gattggggtg acaaggaggg aagttcatat atactatctg    420
gaaaaggcca acaaaattaa atctgagaag acacacattc acatcttcag tttcaccggc    480
gaagaaatgg ccacaaaggc cgattacact ctcgatgaag aaagcagagc caggattaaa    540
accagacttt tcaccataag acaggaaatg gcaagcagag gtctttggga ctcctttcgt    600
cagtccgaaa gaggcgaaga acaattgaa gaaagatttg aaatcacagg acaatgcgc     660
aggctcgctg accaaagcct tccgccgaac ttctcctgca ttgagaattt tagagcctat    720
gtggatggat ttgaaccgaa cggctacatt gagggcaagc tttctcaaat gtccaaagaa    780
gtaaatgcta gaattgagcc ttttttgaaa acaactcctc gaccaattag acttccgaat    840
ggccctcctt gttttcagcg gtctaaattc ctgctgatgg attctttaaa actaagcatt    900
gaagatccaa atcatgaagg tgagggggata ccactatatg atgcaatcaa gtgcatgaga    960
acgttcttcg gatggaaaga acccactgtt gtcaagccac acgagaaggg aataaatccg   1020
aactatctgt tgtcgtggaa gcaagtcttg gaagagctgc aggacattga agtgaggag    1080
aggattccaa gaacaaaaaa catgaaaaaa actagtcagc taaagtgggc acttggtgag   1140
aacatggcac cagaaaaggt ggattttgat gactgtaaag atataagcga cttgaagcaa   1200
tatgacagtg acgaacccga attaagatct ttttcaagtt ggatccagaa tgagttcaac   1260
aaggcatgcg aactgaccga ttcgatctgg atagagcttg atgagattgg agaagatgtg   1320
gccccgattg aacacattgc aagcatgaga aggaactact tcacagctga ggtgtcccat   1380
tgcagagcca cggaatatat aatgaagggg gtgtacatta atactgcctt gctcaatgca   1440
tcttgtgcag caatggatga tttccaacta atccccatga taagcaaatg tagaactaaa   1500
gaaggaagga gaaagaccaa tctctacggc ttcatcgtaa aagggagatc tcacttaagg   1560
aacgacaccg atgtggtcaa cttcgtgagc atggaattt ccctcactga cccaagactt   1620
gagccacaca aatgggagaa gtactgcgtt cttgagatag gagatatgct tctaaggagt   1680
gcaataggcc aagtgtcaag gcccatgttc ctgtatgtaa ggacaaacgg aacctcaaaa   1740
atcaaaatga aatggggaat ggagatgagg cggtgcctcc tccaatccct ccagcaaata   1800
gaaagcatga ttgaagccga gtcctctgtc aaagagaaag acatgacaaa agagttttt    1860
gagaataaat cggaaacatg gcccattgga gaatcaccaa aggagtggga agaaggttcc   1920
attgggaaag tgtgcaggac actgttggcc aagtctgtat tcaacagcct gtatgcatct   1980
ccacaattag aaggattttc agctgaatca agaaagttgc tcctcattgt tcaggccctt   2040
agggacaatc tggaacctgg gacctttgat cttgggggc tatatgaagc aattgaggag   2100
tgcctgatta atgatccctg ggttttgctt aatgcttctt ggttcaactc cttcctaaca   2160
catgcattga gatagctgag gcaatgctac tatttgttat ccatactgtc caaaaagta   2220
ccttgttct act                                                        2233
```

<210> SEQ ID NO 7
<211> LENGTH: 1776
<212> TYPE: DNA
<213> ORGANISM: Influenza virus

<400> SEQUENCE: 7
agcaaaagca ggggaaaata aaagcaacca aaatgaaagt aaaactactg gtcctgttat 60
gcacatttac agctacatat gcagacacaa tatgtatagg ctaccatgct aacaactcga 120
ccgacactgt tgacacagta cttgaaaaga atgtgacagt gacacactct gtcaacctgc 180
ttgagaacag tcacaatgga aaactatgtc tattaaaagg aatagcccca ctacaattgg 240
gtaattgcag cgttgccggg tggatcttag gaaacccaga atgcgaatta ctgatttcca 300
aggagtcatg gtcctacatt gtagaaaaac caaatcctga gaatggaaca tgttacccag 360
ggcatttcgc tgactatgag gaactgaggg agcaattgag ttcagtatct tcatttgaga 420
ggttcgaaat attccccaaa gaaagctcat ggcccaacca caccgtaacc ggagtgtcag 480
catcatgctc ccataatggg gaaagcagtt tttacagaaa tttgctatgg ctgacgggga 540
agaatggttt gtacccaaac ctgagcaagt cctatgcaaa caacaaagaa aaagaagtcc 600
ttgtactatg ggtgttcat cacccgccaa acataggtaa ccaaaaggcc ctctatcata 660
cagaaaatgc ttatgtctct gtagtgtctt cacattatag cagaaaattc accccagaaa 720
tagccaaaag acccaaagta agagatcaag aaggaagaat caattactac tggactctgc 780
ttgaacccgg ggatacaata atatttgagg caaatggaaa tctaatagcg ccaagatatg 840
ctttcgcact gagtagaggc tttggatcag gaatcatcaa ctcaaatgca ccaatggata 900
aatgtgatgc gaagtgccaa acacctcagg gagctataaa cagcagtctt cctttccaga 960
acgtacaccc agtcacaata ggagagtgtc caaagtatgt caggagtgca aaattaagga 1020
tggttacagg actaaggaac atcccatcca ttcaatccag aggtttgttt ggagccattg 1080
ccggtttcat tgaagggggg tggactggaa tggtagatgg ttggtatggt tatcatcatc 1140
agaatgagca aggatctggc tatgctgcag atcaaaaaag cacacaaaat gccattaatg 1200
ggattacaaa caaggtgaat tctgtaattg agaaaatgaa cactcaattc acagcagtgg 1260
gcaaagaatt caacaaattg gaaagaagga tggaaaactt gaataaaaaa gttgatgatg 1320
ggtttataga catttggaca tataatgcag aactgttggt tctactggaa aatgaaagga 1380
ctttggattt ccatgactcc aatgtgaaga atctgtatga gaaagtaaaa agccagttaa 1440
agaataatgc taaagaaata ggaaatgggt gttttgaatt ctatcacaag tgtaacgatg 1500
aatgcatgga gagtgtaaag aatggaactt atgactatcc aaaatattcc gaagaatcaa 1560
agttaaacag ggagaaaatt gatggagtga aattggaatc aatgggagtc tatcagattc 1620
tggcgatcta ctcaacagtc gccagttctc tggttctttt ggtctccctg gggcaatca 1680 gcttctggat gtgttccaat gggtctttac agtgtagaat atgcatctaa gaccagagtt 1740
tcagacatat aaggaaaaaa cacccttgtt tctact 1776

<210> SEQ ID NO 8
<211> LENGTH: 1776
<212> TYPE: DNA
<213> ORGANISM: Influenza virus

<400> SEQUENCE: 8
agcaaaagca ggggaaaata aaagcaacca aaatgaaagt aaaactactg gtcctgttat 60
gcacatttac agctacatat gcagacacaa tatgtatagg ctaccatgct aacaactcga 120

```
ccgacactgt tgacacagta ctcgaaaaga atgtgacagt gacacactct gtcaacctgc    180
ttgagaacag tcacaatgga aaactatgtc tactcaaagg aatagcccca ctacaattgg    240
gtaattgcag cgttgccggg tggatcctcg gaaacccaga atgcgaatta ctaatttcca    300
aggagtcatg tcatacatt gtagaaaaac caaatcctga aatggaaca tgctaccctg      360 ggcatttcgc tgactatgag gaactgaggg agcaattgtc atcagtatct tcatttgaga    420
ggttcgaaat attccccaag gaaagctcat ggcccaacca caccgtaacc ggagtgtcag    480
catcatgctc ccataatggg gaaagcagtt tttacagaaa tctcctatgg ctgacgggga    540
agaatggttt gtacccaaac ctgagcaagt cctatgcaaa caacaaagaa aaagaagtcc    600
tcgtgctatg gggtgttcat cacccgccca acataggtaa ccaaaaggcc ctctatcata    660
cagagaatgc ttatgtctct gtagtgtctt cacattatag cagaaaattc accccagaaa    720
tagccaaaag acccaaggta agagatcaag aaggaagaat caattactac tggactctcc    780
ttgaacccgg ggatacaata atatttgagg caaatggaaa tctaatagcg ccaagatatg    840
ctttcgcact gagtagaggc tttggatcag gaataatcaa ctcaaatgca ccaatggata    900
aatgtgatgc gaagtgccaa acacctcagg agctataaa cagcagtctt cctttccaga    960
acgtgcaccc agtcacaata ggagagtgtc ctaagtatgt taggagtgca aaattaagaa   1020
tggttacagg actaaggaat atcccatcca ttcaatccag aggtttgttt ggagcaattg   1080
ccggcttcat tgaaggggggg tggactggaa tggtagatgg ttggtatggt taccatcatc   1140
agaatgagca agggtctggc tatgctgcag atcaaaaatc aacacaaaat gccattaatg   1200
ggattacaaa caaggtgaat ctgtgattg agaaaatgaa cactcaattc acagcagtgg    1260
gcaaagaatt caacaaattg gaagaagga tggaaaactt gaataaaaag gttgatgatg    1320
ggtttataga catttggaca tacaatgcag aactgttggt tctactggaa aatgaaagga   1380
cattggattt ccatgactcc aatgtgaaga atctgtatga aaagtgaaa agccagctca    1440 agaataatgc taaagaaata ggaaatgggt gctttgaatt ctatcacaag tgtaacgatg   1500
aatgcatgga gagtgttaag aatgaaactt atgactatcc aaaatattca gaagagtcaa   1560
agttaaacag ggagaaaatt gatggagtga agttggaatc aatgggagtc tatcagattc   1620
tggcgatcta ctcaacagtc gccagttctc tggttctttt ggtctccctg ggggcaatca   1680
gcttctggat gtgttccaat gggtctttac agtgtagaat atgcatctaa gaccagagtt   1740
tcagacatat aaggaaaaaa cacccttgtt tctact                              1776

<210> SEQ ID NO 9
<211> LENGTH: 1565
<212> TYPE: DNA
<213> ORGANISM: Influenza virus

<400> SEQUENCE: 9
agcaaaagca gggtagataa tcactcactg agtgacatca aagttatggc gtcccaaggc     60
accaaacggt cttacgaaca gatggagact gatgggggaac gccagaatgc aactgaaatc   120
agagcatccg tcggaagaat gattggtgga attgggcgat tctacatcca aatgtgcacc   180
gagcttaagc tcaatgatta tgagggacgg ctgatccaga acagcttaac aatagagaga    240
atggtgctct ctgctttga tgagaggaga aataaatatc tagaggaaca tcccagcgcg    300
gggaaagatc ctaagaaaac tggaggaccc atatacaaga gagtagatgg aaagtgggtg    360
agggaactcg tcctttatga caaagaagaa ataaggcgga tttggcgcca agccaacaat     420
```

```
ggtgatgatg caacggctgg tttgactcac attatgatct ggcattctaa tttgaatgat      480
acaacttacc agaggacaag agctcttgtc cgcaccggaa tggatcccag gatgtgctct      540
ttgatgcaag gttcaactct ccctagaaga tctggagcag caggcgccgc agtcaaagga      600
gtcgggacaa tggtattgga gttaatcagg atgatcaaac gtgggatcaa tgaccgaaac      660
ttctggaggg gtgagaatgg aagaaaaaca aggattgctt atgagagaat gtgcaacatt      720
ctcaaaggaa aatttcaaac agctgcacaa aaagcaatga tggaccaagt gagagaaagc      780
cggaacccag gaaatgctga gatcgaagat ctcacttttc tggcacggtc tgcactcata      840
ttgagaggat cagttgctca caagtcttgc ctgcctgcct gtgtgtatgg accagcgta       900 gccagtgggt atgacttcga aaaagagggt tactcttttgg taggagtaga ccctttcaaa      960
ctgcttcaaa ccagtcaggt atacagtcta attagaccaa cgagaatcc cgcacacaag       1020 agccagttgg tgtggatggc atgcaattct gctgcatttg aagatctaag agtgtcaagc      1080
ttcatcagag gaacaagagt acttccaagg gggaagctct ccactagagg agtacaaatt      1140
gcttcaaatg aaaacatgga tgctattgtg tcaagtactc ttgaactgag aagcagatac      1200
tgggccataa gaaccagaag tggagggaac actaatcaac aaagggcctc tgcgggccaa      1260
atcagcacac aacctacgtt ttctgtgcag agaaacctcc catttgacaa agcaaccatc      1320
atggcagcat tctctgggaa tacagaggga agaacatcag acatgagggc agaaatcata      1380
aagatgatgg aaagtgcaag accagaagaa gtgtccttcc aggggcgggg agtctttgag      1440
ctctcggacg aaagggcaac gaacccgatc gtgccctcct ttgacatgag taatgaagga      1500
tcttatttct tcggagacaa tgcagaggag tacgacaatt aatgaaaaat acccttgttt      1560
ctact                                                                  1565

<210> SEQ ID NO 10
<211> LENGTH: 1565
<212> TYPE: DNA
<213> ORGANISM: Influenza virus

<400> SEQUENCE: 10
agcaaaagca gggtagataa tcactcactg agtgacatca aagttatggc gtcccaaggc       60
accaaacggt cttacgaaca gatggagact gatggggaac gccagaatgc aactgaaatc      120
agagcatccg tcgggagaat gattggtgga attgggcgat tctacatcca aatgtgcacc      180
gaacttaagc tcaatgatta tgagggacga ctgatccaga acagcttaac aatagagaga      240
atggtgctct ctgcttttga tgagaggaga aataaatatc tagaggaaca tcccagcgcg      300
gggaaagatc ctaagaaaac tggaggaccg atatacaaga gagttgatgg aaagtgggtg      360
agggaactcg tcctttatga caagaagaa ataaggcgga tttggcgtca agcgaacaat      420
ggggatgatg caacggctgg tctgactcac attatgatct ggcattctaa tttgaatgat      480
acaacttacc agaggactag agctcttgtt cgcaccggaa tggaccccag gatgtgctcc      540
ttgatgcaag gttcgactct ccctagaaga tctggagcag caggcgccgc agtcaaagga      600
gtcgggacaa tggtactgga gctgatcagg atgatcaaac gtgggatcaa tgaccgaaac      660
ttctggaggg gtgagaatgg aagaaaaaca aggattgctt atgagagaat gtgcaacatt      720
ctcaaaggaa aatttcaaac agctgcacaa aaagcaatga tggaccaggt gagagaaagc      780
cggaacccag gaaatgctga gatcgaagat ctcacttttc cggcacggtc tgcactcata      840
ctgagaggat cagttgctca taagtcttgc ctgcctgcct gtgtgtatgg accagcgtt       900 gccagtgggt atgacttcga aaaagagggt tattctttgg ttggagtaga ccctttcaaa      960
```

| | |
|---|---:|
| ctgctgcaaa ccagtcaggt atacagtcta attagaccaa acgagaaccc cgcacacaag | 1020 |
| agccagctgg tgtggatggc atgcaattct gctgcatttg aagacctaag agtgtcaagc | 1080 |
| ttcatcagag gaacaagagt acttccaagg gggaagctct ccactagagg agtacaaatt | 1140 |
| gcttcaaatg aaaacatgga tgctattgtg tcaagtactc ttgaactgag aagtagatac | 1200 |
| tgggccataa gaaccagaag tggagggaac actaatcaac aaagggcctc tgcgggccaa | 1260 |
| atcagcacac agcctacgtt ttctgtgcag agaaacctcc cattcgacaa agcaaccatc | 1320 |
| atggcagcat tctctgggaa tacagaggga agaacatcag acatgagggc agaaatcata | 1380 |
| aagatgatgg aaagtgcaag accagaagaa gtgtccttcc aggggcgggg agtctttgag | 1440 |
| ctctcggacg aaagggcaac gaacccgatc gtgcccctcct ttgacatgag taatgaagga | 1500 |
| tcttatttct tcggagacaa tgcagaggag tacgacaatt aatgaaaaat acccttgttt | 1560 |
| ctact | 1565 |

<210> SEQ ID NO 11
<211> LENGTH: 1462
<212> TYPE: DNA
<213> ORGANISM: Influenza virus

<400> SEQUENCE: 11

| | |
|---|---:|
| agcaaaagca ggagtttaaa atgaacccaa atcaaaagat aataaccatt ggatcaatca | 60 |
| gtatagcaat cggaataatt agtctaatgt tgcaaatagg aaatattatt tcaatatggg | 120 |
| ctagtcactc aatccaaact ggaagtcaaa acaacactgg aatatgcaac caaagaatca | 180 |
| tcacatatga aaacagcacc tgggtgaatc acacatatgt taatattaac aacactaatg | 240 |
| ttgttgctgg agaggacaaa acttcagtga cattggctgg caattcatct ctttgttcta | 300 |
| tcagtggatg ggctatatac acaaaagaca acagcataag aattggctcc aaaggagatg | 360 |
| tttttgtcat aagagaacct ttcatatcat gttctcactt ggaatgcaga accttttttc | 420 |
| tgacccaagg cgctctatta aatgacaaac attcaaatgg gaccgtaaag gacagaagtc | 480 |
| cttatagggc cttaatgagc tgtcctctag gtgaagctcc gtccccatac aattcaaagt | 540 |
| tcgaatcagt tgcatggtca gcaagcgcat gccatgatgg catgggctgg ttaacaatcg | 600 |
| gaatttctgg tccagacaat ggagctgtgg ctgtactaaa atacaacgga ataataactg | 660 |
| gaaccataaa aagttggaaa aagcaaatat taagaacaca agagtctgaa tgtgtctgta | 720 |
| tgaacgggtc atgtttcacc ataatgaccg atggcccgag taataaggcc gcctcgtaca | 780 |
| aaattttcaa gatcgaaaag ggaaaggtta ctaaatcaat agagttgaat gcacccaatt | 840 |
| ttcattatga ggaatgttcc tgttacccag acactggcat agtgatgtgt gtatgcaggg | 900 |
| acaactggca tggttcaaat cgaccttggg tgtcttttaa tcaaaacttg gattatcaaa | 960 |
| taggatacat ctgcagtgga gtgttcggtg acaatccgcg tcccgaagat ggagagggca | 1020 |
| gctgcaatcc agtgactgtt gatggagcaa acggagtaaa agggttttca tacaaatatg | 1080 |
| ataatggtgt ttggatagga aggaccaaaa gtaacagact tagaaagggg tttgagatga | 1140 |
| tttgggatcc taatggatgg acaaataccg acagtgattt ctcagtgaaa caggatgttg | 1200 |
| tagcaataac tgattggtca gggtacagcg aagtttcgt ccaacatcct gagttaacag | 1260 |
| gattggactg tataagacct tgcttctggg ttgagttagt cagagggctg cctagagaaa | 1320 |
| atacaacaat ctggactagt gggagcagca tttcttttg tggcgttaat agtgatactg | 1380 |
| caaactggtc ttggccagac ggtgctgagt tgccgttcac cattgacaag tagttcgttg | 1440 |

```
aaaaaaactc cttgtttcta ct                                               1462
```

<210> SEQ ID NO 12
<211> LENGTH: 1462
<212> TYPE: DNA
<213> ORGANISM: Influenza virus

<400> SEQUENCE: 12

```
agcaaaagca ggagtttaaa atgaacccaa atcaaaagat aataaccatt ggatcaatca        60
gtatagcaat cggaataatt agtctaatgt tgcaaatagg aaatattatt tcaatatggg       120
ctagtcactc aatccaaact ggaagtcaaa acaacactgg aatatgcaac caaagaatca       180
tcacatatga aaacagcacc tgggtgaatc acacatatgt taatattaac aacactaatg       240
tagttgctgg agaggacaaa acttcagtga cattggctgg caattcatct ctttgttcta       300
tcagtgggtg ggctatatac acaaaagaca acagcataag aattggctcc aaaggagatg       360
tatttgtcat cagagaacct tttatatcct gttctcactt ggaatgcaga accttttttc       420
tgacccaggg cgctctgtta aatgacaaac attcaaatgg accgtaaag acaggagtc         480
cctatagggc ttgatgagc tgccctctag gtgaagctcc atccccatac aattccaagt        540
tcgagtcagt tgcgtggtca gcaagcgctt gccatgatg tatgggctgg ttaacaatcg        600
ggatttctgg tccagacaat ggtgctgtgg ctgtactaaa atacaacgga ataataactg       660
ggaccataaa aagttggaaa aagcaaatat taagaacaca ggagtctgaa tgtgtctgta       720
tgaatgggtc ctgtttcacc ataatgactg atggcccaag taataaggcc gcctcgtata       780
aaattttcaa gatcgaaaag gggaaggtaa ctaaatcaat agagttgaat gctcccaatt       840
ttcattatga ggaatgctcc tgttatccag acactggcat agtgatgtgt gtatgcaggg       900
acaattggca cggttccaat cggccttggg tgtcttttaa tcagaacttg gattatcaaa       960
ttggatacat ctgcagtggg gtgttcggtg acaatccgcg ccccgaagat ggagagggca      1020
gctgcaatcc agtgactgtt gatggagcaa acggagtaaa agggttttca tacaaatatg      1080
ataatggtgt atggataggg aggaccaaaa gtaacagact taggaagggg tttgagatga      1140
tttgggatcc aaatgatgg acaaatacgg acagtgattt ttcagtgaaa caggatgttg      1200
tagcaataac tgattggtca gggtacagcg ggagtttcgt ccagcatcct gagttaacag      1260
gattggacta tataagacct tgcttctggg ttgagttagt cagagggctg cctagagaaa      1320
atacaacaat ctggactagt gggagcagca tttcttttg tggcgttaat agtgatactg      1380
caaactggtc ttggccagac ggtgctgagt tgccgttcac cattgacaag tagttcgttg      1440
aaaaaaactc cttgtttcta ct                                               1462
```

<210> SEQ ID NO 13
<211> LENGTH: 1027
<212> TYPE: DNA
<213> ORGANISM: Influenza virus

<400> SEQUENCE: 13

```
agcaaaagca ggtagatatt gaaagatgag tcttctaacc gaggtcgaaa cgtacgttct        60
ctctatcatc ccgtcaggcc ccctcaaagc cgagatcgca cagagacttg aagatgtatt       120
tgctggaaag aataccgatc ttgaggctct catggagtgg ctaaagacaa gaccaatcct       180
gtcacctctg actaagggga ttttaggatt tgtgttcacg ctcaccgtgc ccagtgagcg       240
aggactgcag cgtagacgct ttgtccaaaa tgcccttaat gggaatgggg atccaaataa       300
tatggacaga gcagtcaaac tttatcgaaa gcttaagagg gagataacat ccatggggc       360
```

-continued

```
caaagaaata gcactcagtt attctgctgg tgcacttgcc agttgtatgg gactcatata      420
caacaggatg ggggctgtga ccaccgaatc agcatttggc cttatatgtg caacctgtga      480
acagattgcc gactcccagc ataagtctca caggcaaatg gtaacaacaa ccaatccatt      540
aataagacat gagaacagaa tggttctggc agcactaca gctaaggcta tggagcaaat      600
ggctggatcg agcgaacaag cagctgaggc catggaggtt gctagtcagg ccaggcagat      660
ggtgcaggca atgagagcca ttgggactca tcctagctct agcactggtc tgaaaaatga      720
tctccttgaa aatttacagg cctatcagaa acgaatgggg gtgcagatgc aacgattcaa      780
gtgatcctct tgttgttgcc gcaagtataa ttgggattgt gcacttgata ttgtggatta      840
ttgatcgcct ttttccaaa agcatttatc gtatctttaa acacggttta aaaagagggc       900
cttctacgga aggagtacca gagtctatga gggaagaata tcgagaggaa cagcagaatg      960
ctgtggatgc tgacgatgat cattttgtca gcatagagct agagtaaaaa actaccttgt     1020
ttctact                                                                1027
```

<210> SEQ ID NO 14
<211> LENGTH: 1027
<212> TYPE: DNA
<213> ORGANISM: Influenza virus

<400> SEQUENCE: 14

```
agcaaaagca ggtagatatt gaaagatgag tcttctaacc gaggtcgaaa cgtacgttct       60
ctctatcatc ccgtcaggcc ccctcaaagc cgagatcgca cagagacttg aagatgtatt      120
tgctggaaag aataccgatc ttgaggctct catggagtgg ctaaagacaa gaccaatcct      180
gtcacctctg actaagggta ttttgggatt tgtgttcacg ctcaccgtgc ccagtgagcg      240
aggactgcag cgtagacgct ttgtccaaaa cgcccttaat gggaacgggg atccaaacaa      300
tatggacaga gcagtcaaac tttaccggaa gctaaagagg gagataacat tccatggggc      360
gaaagaaatc gcactcagtt actccgctgg tgcactagcc agttgtatgg gactcatata      420
caacaggatg ggggctgtga ctaccgaatc agcatttggc ctaatatgtg caacctgcga      480
acagattgcc gattcccagc ataagtcaca caggcagatg gtgacaacaa ccaatccatt      540
gataagacat gagaacagaa tggttctggc agcactaca gctaaagcta tggagcagat      600
ggctggatcg agtgaacaag cagctgaggc catggaggtt gcgagtcagg ccaggcagat      660
ggtgcaggca atgagggcca ttggaactca tcctagctct agcactggtc tgaaaaatga      720
tctccttgaa aatttacagg cctatcagaa acgaatgggg gtgcagatgc aacgattcaa      780
gtgatcctct tgttgttgcc gcaagtataa ttgggattgt gcacttgata ttgtggatta      840
ttgatcgcct ttttccaaa agcatttatc gtatctttaa acacggttta aaaagagggc       900
cttctacgga aggagtacca gagtctatga gggaagaata tcgagaggaa cagcagaatg      960
ctgtggatgc tgacgatgat cattttgtca gcatagagct agagtaaaaa actaccttgt     1020
ttctact                                                                1027
```

<210> SEQ ID NO 15
<211> LENGTH: 890
<212> TYPE: DNA
<213> ORGANISM: Influenza virus

<400> SEQUENCE: 15

```
agcaaaagca gggtggcaaa gacataatgg attcccacac tgtgtcaagc tttcaggtag       60
```
attgcttcct ttggcatgtc cgcaaacaag ctgcagacca agatctaggc gatgccccct 120
tccttgatcg gcttcgccga gatcagaagt ctctaaaggg aagaggcagc actctcggtc 180
tgaacatcga aacagctact tgtgttggaa agcaaatagt agagaggatt ctgaaagaag 240
aatccgatga ggcacttaaa atgaccatgg cctccgcact tgcttcgcgg tacctaactg 300
acatgactgt tgaagaaatg tcaagggact ggttcatgct catgcccaag caaaaagtgg 360
ctggccctct ttgtgtcaga atggaccagg caataatgga taagaacatc atactgaaag 420
cgaatttcag tgtgattttt gaccggttgg agaatctgac attactaagg gctttcaccg 480
aagagggagc aattgttggc gaaatttcac cattgccttc ttttccagga catactaatg 540
aggatgtcaa aaatgcaatt ggggtcctca tcgggggact tgaatggaat gataacacag 600
ttcgagtctc tgaaactcta cagagattcg cttggagaag cagtaatgag actgggggac 660
ctccattcac tacaacacag aaacggaaaa tggcgggaac aactaggtca gaagtttgaa 720
gaagtaagat ggctgattga agaagtgagg cataaattga agacgacaga gaatagtttt 780
gagcaaataa catttatgca agcattacag ctattatttg aagtggaaca agagattaga 840
acgttttcgt ttcagcttat ttagtgataa aaaacaccct tgtttctact 890

<210> SEQ ID NO 16
<211> LENGTH: 890
<212> TYPE: DNA
<213> ORGANISM: Influenza virus

<400> SEQUENCE: 16
agcaaaagca gggtggcaaa gacataatgg attcccacac tgtgtcaagc tttcaggtag 60
attgcttcct ttggcatgtc cgcaaacaag ctgcagacca agatctaggc gatgccccct 120
tccttgatcg gcttcgccga gatcagaagt ctctaaaggg aagaggcagc actctcggtc 180
tgaacatcga aacagctact tgtgtgggaa agcaaatagt agagagaatt ctgaaagaag 240
aatccgatga ggcacttaaa atgaccatgg cctccgcact tgcttcacgg tacctaacgg 300
acatgactgt ggaagagatg tcaagagact ggttcatgct catgccaaag cagaaagtgg 360
ctggtcctct ttgcgtcaga atggaccagg caataatgga taagaacatc atactgaaag 420
cgaacttcag tgtgattttt gaccgactcg agaatctgac attactaaga gcttttaccg 480
aagagggagc aattgttggt gaaatttcac cattgccttc ttttccagga catactaatg 540
aggatgtcaa aaatgcaatt ggggtcctca tcgggggact tgaatggaat gataacacag 600
ttcgagtctc tgaaactcta cagagattcg cttggagaag cagtaatgag actgggggac 660
ctccattcac tacaacacag aaacggaaaa tggcgggaac aactaggtca gaagtttgaa 720
gaagtaagat ggctgattga agaagtgagg cataaattga agacgacaga gaatagtttt 780
gagcaaataa catttatgca agcattacag ctattatttg aagtggaaca agagattaga 840
acgttttcgt ttcagcttat ttagtgataa aaaacaccct tgtttctact 890

<210> SEQ ID NO 17
<211> LENGTH: 2341
<212> TYPE: DNA
<213> ORGANISM: Influenza virus

<400> SEQUENCE: 17
agcgaaagca ggtcaattat attcaatatg gaaagaataa aagaactacg aaatctaatg 60
tcgcagtctc gcacccgcga gatactcaca aaaaccaccg tggaccatat ggccataatc 120
aagaagtaca catcaggaag acaggagaag aacccagcac ttaggatgaa atggatgatg 180

```
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag    1020
agaacaagcg gatcatcagt caagagagag gaagaggtgc ttacgggcaa tcttcaaaca    1080
ttgaagataa gagtgcatga gggatatgaa gagttcacaa tggttgggag aagagcaaca    1140
gccatactca gaaaagcaac caggagattg attcagctga tagtgagtgg gagagacgaa    1200
cagtcgattg ccgaagcaat aattgtggcc atggtatttt cacaagagga ttgtatgata    1260
aaagcagtca gaggtgatct gaatttcgtc aatagggcga atcaacgatt gaatcctatg    1320
catcaacttt taagacattt tcagaaggat gcgaaagtgc tttttcaaaa ttggggagtt    1380
gaacctatcg acaatgtgat gggaatgatt gggatattgc cgacatgac tccaagcatc    1440 gagatgtcaa tgagaggagt gagaatcagc aaaatgggtg tagatgagta ctccagcacg    1500
gagagggtag tggtgagcat tgaccgtttt ttgagaatcc gggaccaacg aggaaatgta    1560
ctactgtctc ccgaggaggt cagtgaaaca cagggaacag agaaactgac aataacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca aagtagaatg    1920
cagttctcct catttactgt gaatgtgagg ggatcaggaa tgagaatact tgtaaggggc    1980
aattctcctg tattcaacta taacaaggcc acgaagagac tcacagttct cggaaaggat    2040
gctggcactt taactgaaga cccagatgaa ggcacagctg gagtggagtc cgctgttctg    2100 agggattcc tcattctggg caaagaagac aagagatatg gccagcact aagcatcaat    2160 gaactgagca accttgcgaa aggagagaag gctaatgtgc taattgggca aggagacgtg    2220
gtgttggtaa tgaaacggaa acgggactct agcatactta ctgacagcca gacagcgacc    2280
aaaagaattc ggatggccat caattagtgt cgaatagttt aaaaacgacc ttgtttctac    2340
t                                                                   2341
```

<210> SEQ ID NO 18
<211> LENGTH: 2341
<212> TYPE: DNA

<213> ORGANISM: Influenza virus

<400> SEQUENCE: 18
agcgaaagca ggtcaattat attcaatatg gaaagaataa aagaactacg aaatctaatg 60
tcgcagtctc gcacccgcga gatactcaca aaaaccaccg tggaccatat ggccataatc 120
aagaagtaca catcaggaag acaggagaag aacccagcac ttaggatgaa atggatgatg 180
gcaatgaaat atccaattac agcagacaag aggataacgg aaatgattcc tgagagaaat 240
gagcaaggac aaactttatg gagtaaaatg aatgatgccg gatcagaccg agtgatggta 300
tcacctctgg ctgtgacatg gtggaatagg aatggaccaa taacaaatac agttcactat 360
ccaaaaatct acaaaactta ttttgaaaga gtcgaaaggc taaagcatgg aaccttcggc 420
cctgtccatt ttagaaacca agtcaaaata cgtcggagag ttgacataaa tcctggtcat 480
gcagatctca gtgccaagga ggcacaggat gtaatcatgg aagttgtttt ccctaacgaa 540
gttggagcca ggatactaac aagtgaatcg caactaacga taaccaaaga gaagaaagaa 600
gaactccagg attgcaaaat ttctccgttg atggttgcat acatgttgga gagagaactg 660
gtccgcaaaa cgagattcct cccagtagct ggtggaacaa gcagtgtgta cattgaagtg 720
ttgcacttga ctcaaggaac atgctgggaa caaatgtata ctccaggagg ggaagttagg 780
aatgatgatg ttgatcaaag cttgattatc gctgctagga acatagtgag aagagctgca 840
gtatcagcag atccgctagc atctttattg gagatgtgcc acagcacaca gattggtggg 900
attaggatgg tagacatctt aaggcagaac ccaacagaag agcaagcagt ggatatatgc 960
aaggctgcaa tgggactgag aattagctca tccttcagtt tcggtggatt cacatttaaa 1020
agaacaagcg gatcatcagt caagagagag gaagaggtgc ttacgggcaa tttgcaaaca 1080
ttgaagataa gagtgcatga ggggtatgaa gagttcacaa tggttgggag acgggcaaca 1140
gcaatactca gaaaagcaac caggagattg attcagctga tagtgagtgg gcgcgacgaa 1200
cagtcgattg cagaagcaat aattgtggcc atggtattct cacaagagga ttgtatgata 1260
aaagcagtca gaggtgatct gaatttcgtc aacagggcga atcaacgatt gaatcctatg 1320
caccaacttt taagacattt tcagaaggat gctaaagtgc tctttcaaaa ttggggagtt 1380
gaacccatcg acaacgtgat gggaatgatt gggatattgc ccgacatgac tccaagcatc 1440
gagatgtcaa tgagaggagt gagaatcagc aaaatgggtg tagatgagta ctccagcaca 1500
gagagggtag tggtaagcat tgaccgtttt ttgaggatcc gggaccaacg aggaaatgta 1560
ctactgtctc ccgaggaggt cagtgaaaca caggggacag agaaactgac aataacttac 1620
tcatcgtcaa tgatgtggga gattaatggc cctgaatcag tgttggtcaa tacctatcaa 1680
tggatcatca gaaactggga aactgttaaa attcagtggt cccagaaccc cacaatgcta 1740
tacaataaaa tggaattcga accatttcag tctttagtac ctaaggcaat tagaggccaa 1800
tacagtgggt ttgtaagaac tctgttccaa caaatgaggg acgtgcttgg gacatttgat 1860
accgcacaga taataaaatt gcttcccttc gcagccgctc caccaaagca aagtagaatg 1920
cagttctcat catttactgt gaatgtgagg ggctcaggaa tgagaatact tgtaaggggc 1980
aattctcccg tattcaacta taacaaggcc acgaagagac tcacagttct cggaaaggat 2040
gctggcactt taactgaaga cccagatgaa ggcacagctg gagtggagtc cgctgttctg 2100
aggggattcc tcattctggg caaagaagac aagagatatg ggccagcact aagcatcaat 2160
gaactgagca accttgcgaa aggagagaag gctaatgtgc taattgggca aggagacgtg 2220
gtgttggtaa tgaaacggaa acgggactct agcatactta ctgacagcca gacagcgacc 2280

| aaaagaattc ggatggccat caattagtgt cgaatagttt aaaaacgacc ttgtttctac | 2340 |
| t | 2341 |

<210> SEQ ID NO 19
<211> LENGTH: 2341
<212> TYPE: DNA
<213> ORGANISM: Influenza virus

<400> SEQUENCE: 19

| agcgaaagca ggcaaaccat ttgaatggat gtcaatccga ccttactttt cttaaaagtg | 60 |
| ccagcacaaa atgctataag cacaactttc ccttatactg gagaccctcc ttacagccat | 120 |
| gggacaggaa caggatacac catggatact gtcaacagga cacatcagta ctcagaaaag | 180 |
| ggaagatgga caacaaacac cgaaactgga gcaccgcaac tcaacccgat tgatgggcca | 240 |
| ctgccagaag acaatgaacc aagtggttat gcccaaacag attgtgtatt ggaggcgatg | 300 |
| gctttccttg aggaatccca tcctggtatt tttgaaaact cgtgtattga acgatggag | 360 |
| gttgttcagc aaacacgagt agacaagctg acacaaggcc gacagaccta tgactggact | 420 |
| ctaaatagaa accaacctgc tgcaacagca ttggccaaca atagaagt gttcagatca | 480 |
| aatggcctca cggccaatga gtctggaagg ctcatagact tccttaagga tgtaatggag | 540 |
| tcaatgaaca agaagaaat ggggatcaca actcattttc agagaaagag acgggtgaga | 600 |
| gacaatatga ctaagaaaat gataacacag agaacaatgg gtaaaagaa gcagagattg | 660 |
| aacaaaagga gttatctaat tagagcattg accctgaaca caatgaccaa agatgctgag | 720 |
| agagggaagc taaaacggag agcaattgca acccccaggga tgcaaataag ggggtttgta | 780 |
| tactttgttg agacactggc aaggagtata tgtgagaaac ttgaacaatc agggttgcca | 840 |
| gttggaggca atgagaagaa agcaaagttg gcaaatgttg taaggaagat gatgaccaat | 900 |
| tctcaggaca ccgaactttc tttcaccatc actggagata acaccaaatg gaacgaaaat | 960 |
| cagaatcctc ggatgttttt ggccatgatc acatatatga ccagaaatca gcccgaatgg | 1020 |
| ttcagaaatg ttctaagtat tgctccaata atgttctcaa acaaaatggc gagactggga | 1080 |
| aaggggtata tgtttgagag caagagtatg aaacttagaa ctcaaatacc tgcagaaatg | 1140 |
| ctagcaagca tcgatttgaa atatttcaat gattcaacaa gaagaagat tgaaaaaatc | 1200 |
| cgaccgctct aatagaggg gactgcatca ttgagccctg aatgatgat gggcatgttc | 1260 |
| aatatgttaa gcactgtatt aggcgtctcc atcctgaatc ttggacaaaa gagatacacc | 1320 |
| aagactacta ctggtggga tggtcttcaa tcctctgacg atttttgctct gattgtgaat | 1380 |
| gcacccaatc atgaagggat tcaagccgga gtcgacaggt tttatcgaac ctgtaagcta | 1440 |
| cttggaatca atatgagcaa gaaaaagtct tacataaaca gaacaggtac atttgaattc | 1500 |
| acaagttttt tctatcgtta tgggtttgtt gccaatttca gcatggagct tcccagttttt | 1560 |
| ggggtgtctg ggatcaacga gtcagcggac atgagtattg gagttactgt catcaaaaac | 1620 |
| aatatgataa acaatgatct tggtccagca acagctcaaa tggcccttca gttgttcatc | 1680 |
| aaagattaca ggtacacgta ccgatgccat ataggtgaca cacaaataca aacccgaaga | 1740 |
| tcatttgaaa taaagaaact gtgggagcaa acccgttcca agctggact gctggtctcc | 1800 |
| gacggaggcc caatttata caacattaga aatctccaca ttcctgaagt ctgcctaaaa | 1860 |
| tgggaattga tggatgagga ttaccagggg cgtttatgca acccactgaa cccatttgtc | 1920 |
| agccataaag aaattgaatc aatgaacaat gcagtgatga tgccagcaca tggtccagcc | 1980 |

| | |
|---|---|
| aaaaacatgg agtatgatgc tgttgcaaca acacactcct ggatccccaa agaaatcga | 2040 |
| tccatcttga atacaagtca agaggagta cttgaggatg aacaaatgta ccaaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 20
<211> LENGTH: 2341
<212> TYPE: DNA
<213> ORGANISM: Influenza virus

<400> SEQUENCE: 20

| | |
|---|---|
| agcgaaagca ggcaaaccat ttgaatggat gtcaatccga ccttactttt cttaaaagtg | 60 |
| ccagcacaaa atgctataag cacaacattc ccttatactg gagaccctcc ttacagccat | 120 |
| gggacaggaa caggatacac catggatact gtcaacagga cacatcagta ctcagaaaag | 180 |
| ggaagatgga caacaaacac cgaaactgga gcaccgcaac tcaacccgat tgatgggcca | 240 |
| ctgccagaag acaatgaacc aagtggttat gcccaaacag attgtgtatt ggaggcgatg | 300 |
| gctttccttg aggaatccca ccctggtatt tttgaaaact cgtgtattga acgatggag | 360 |
| gttgttcagc aaacacgagt agacaagctg acacaaggca ggcagacgta tgactggaca | 420 |
| ctaaatagaa accaacctgc tgcaacagct ttggccaaca atagaagt gttcagatca | 480 |
| aatggcctca cggccaatga gtctggaagg ctcatagact cctcaaggaa tgtaatggag | 540 |
| tcaatgaaca agaagaaat ggggataaca actcactttc agagaaagag acgggtgaga | 600 |
| gacaatatga caagaaaat gataacacag agaacaatgg gtaagaagaa gcagagattg | 660 |
| aacaaaagga gttatctaat tagagcattg acgctgaaca caatgaccaa agacgctgag | 720 |
| agaggaaagc taaaacggag ggcaattgca accccaggaa tgcaaataag ggggttgtg | 780 |
| tactttgttg agacactggc aaggagtata tgtgagaagc ttgaacaatc aggattgcca | 840 |
| gttggaggaa atgagaagaa agcaaagttg gcaaatgttg taaggaagat gatgacaaat | 900 |
| tctcaggaca cggaactttc tttcaccatc actggagata caccaagtg gaacgaaaac | 960 |
| cagaatcctc ggatgttttt ggccatgatc acatatatga caagaaatca cccgaatgg | 1020 |
| ttcagaaatg ttctaagcat tgctccgata atgttctcaa acaaaatggc gaggctggga | 1080 |
| aagggtata tgttcgagag caagagtatg aaacttagaa cacaaatacc tgcagaaatg | 1140 |
| ctagcaagca tcgatttgaa atatttcaat gattcaacaa gaagaagat tgaaaaaatc | 1200 |
| cgaccgctct aatagaggg gactgcatca ctgagccctg aatgatgat gggcatgttc | 1260 |
| aacatgttaa gcacagtatt aggcgtctcc atcctgaatc tcggacaaaa gagatacacc | 1320 |
| aagactactt actggtggga tggacttcaa tcatctgacg atttgctct gattgtgaat | 1380 |
| gcacccaatc atgaaggaat tcaagccgga gtcgacaggt tctatcgaac atgtaagcta | 1440 |
| cttggaataa atatgagcaa gaaaagtct tacataaaca gaacaggtac atttgaattc | 1500 |
| acaagctttt tctatcgtta tgggtttgtt gctaatttca gcatggagct tccgagtttt | 1560 |
| ggggtgtctg gaatcaacga gtcagcggac atgagcattg gagttacagt catcaaaaac | 1620 |
| aatatgataa acaatgatct tggaccagca acagctcaaa tggccctcca gttgttcatc | 1680 |
| aaagattaca ggtacacgta ccgatgccat ataggagaca cacaaataca aacccgcaga | 1740 |

```
tcatttgaaa taaagaaact gtgggagcaa acccgttcga aagctggact gctggtctcc    1800
gacggaggcc caaatctata caacattagg aatctccaca ttcctgaagt ctgcctaaag    1860
tgggaactga tggatgagga ttaccagggg cgcttatgca acccactgaa cccatttgtc    1920
agccacaaag aaattgaatc aatgaacaat gcagtgatga tgccagcaca tggaccagcc    1980
aaaaacatgg agtatgatgc tgttgcaaca acacactcgt ggatccccaa agaaatagg     2040 tccatcctaa atacaagtca aaggggagta cttgaggatg aacaaatgta ccaaggtgc     2100 tgcaatctat ttgaaaaatt cttccccagc agttcataca ggagaccagt cggaatatcc    2160
agcatggtgg aggctatggt ttccagagcc cgcattgatg cacggattga tttcgaatct    2220
ggaaggataa agaaagaaga gttcactgag atcatgaaga tctgttccac cattgaagag    2280
ctcagacggc aaaaatagtg aatttagctt gtccttcatg aaaaaatgcc ttgtttctac    2340
t                                                                    2341

<210> SEQ ID NO 21
<211> LENGTH: 2233
<212> TYPE: DNA
<213> ORGANISM: Influenza virus

<400> SEQUENCE: 21
agcgaaagca ggtactgatc caaaatggaa gattttgtgc gacaatgctt caatccgatg      60
attgtcgagc ttgcggaaaa aacaatgaaa gagtatgggg aggacctgaa atcgaaaca     120 aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca cactacagg ggctgagaaa ccaaagtttc taccagattt gtatgattac    360
aaggagaata gattcatcga aattggagta caaggagag aagttcacat atactatctg    420
gaaaaggcca ataaaattaa atctgagaaa acacacatcc acattttctc gttcactggg    480
gaagaaatgg ccacaaaggc agactacact ctcgatgaag aaagcagggc taggatcaaa    540
accagactat tcaccataag acaagaaatg gccagcagag gcctctggga ttccttttcgt    600 cagtccgaga gaggagaaga gacaattgaa gaaaggtttg aaatcacagg aacaatgcgt    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac    1380
tgcagagcca cagaatacat aatgaaggga gtgtacatca atactgcctt gcttaatgca    1440
```

-continued

| | |
|---|---|
| tcttgtgcag caatggatga tttccaatta attccaatga taagcaagtg tagaactaag | 1500 |
| gagggaaggc gaaagaccaa cttgtatggt ttcatcataa aaggaagatc ccacttaagg | 1560 |
| aatgacaccg acgtggtaaa cttttgtgagc atggagtttt ctctcactga cccaagactt | 1620 |
| gaaccacata aatgggagaa gtactgtgtt cttgagatag gagatatgct tataagaagt | 1680 |
| gccataggcc aggtttcaag gcccatgttc ttgtatgtga aacaaatgg aacctcaaaa | 1740 |
| attaaaatga aatggggaat ggagatgagg cgttgcctcc tccagtcact tcaacaaatt | 1800 |
| gagagtatga ttgaagctga gtcctctgtc aaagagaaag acatgaccaa agagttcttt | 1860 |
| gagaacaaat cagaaacatg gcccattgga gagtccccca aaggagtgga ggaaagttcc | 1920 |
| attgggaagg tctgcaggac tttattagca aagtcggtat tcaacagctt gtatgcatct | 1980 |
| ccacaactag aaggattttc agctgaatca agaaaactgc ttcttatcgt tcaggctctt | 2040 |
| agggacaacc tggaacctgg gacctttgat cttgggggc tatatgaagc aattgaggag | 2100 |
| tgcctgatta atgatccctg gtttttgctt aatgcttctt ggttcaactc cttccttaca | 2160 |
| catgcattga gttagttgtg gcagtgctac tatttgctat ccatactgtc caaaaaagta | 2220 |
| ccttgtttct act | 2233 |

<210> SEQ ID NO 22
<211> LENGTH: 2233
<212> TYPE: DNA
<213> ORGANISM: Influenza virus

<400> SEQUENCE: 22

| | |
|---|---|
| agcgaaagca ggtactgatc caaaatggaa gattttgtgc gacaatgctt caatccgatg | 60 |
| attgtcgagc ttgcggaaaa aacaatgaaa gagtatgggg aggacctgaa atcgaaaca | 120 |
| aacaaattcg cagcaatatg cacgcacttg gaagtatgct tcatgtattc tgattttcac | 180 |
| ttcatcaacg agcaaggcga gtcaataatc gtagaacttg gtgatccaaa tgcactattg | 240 |
| aagcacagat ttgaaataat cgaaggaaga gatcgcacaa tggcctggac agtagtgaac | 300 |
| agtatttgca acactaccgg ggctgagaaa ccaaagtttc taccagattt gtatgattac | 360 |
| aaggaaaata gattcatcga aattggagtg acaaggagag aagttcacat atactatctg | 420 |
| gaaaaggcca acaaaattaa atctgagaaa acacacatcc acatttttctc gttcactggg | 480 |
| gaagaaatgg caacaaaggc agactacact ctcgatgaag aaagcagggc taggataaaa | 540 |
| accagactat tcaccataag acaagaaatg gccagcagag gcctctggga ttcctttcgt | 600 |
| cagtccgaga gaggagaaga gacaattgaa gaaaggtttg aaatcacagg aacaatgcgt | 660 |
| aagcttgccg accaaagtct cccgccgaac ttctccagcc ttgaaaattt tagagcctat | 720 |
| gtggatggat tcgaaccgaa cggctacatt gagggcaagc tgtctcaaat gtccaaagaa | 780 |
| gtaaatgcta gaattgaacc ttttcttgaaa acaacacctc gaccacttag actaccgaat | 840 |
| gggcctcccct gctctcagcg gtccaaattc ctgctgatgg atgccttaaa attaagcatt | 900 |
| gaagacccaa gtcatgaagg cgagggaata ccgctatacg atgcaatcaa atgcatgcgg | 960 |
| acattctttg gtggaaggaa acccaatgtt gttaaaccac atgaaaaggg aataaatcca | 1020 |
| aactatcttc tgtcatggaa gcaagtgctg cagaactgc aggacattga gatgaggag | 1080 |
| aaaattccaa agactaaaaa tatgaagaaa accagtcagc taaagtgggc actaggtgag | 1140 |
| aacatggcac cagaaaaggt agactttgac gactgtaaag atgtaggtga tctgaagcaa | 1200 |
| tatgattcga tgaaccaga attgaggtcg cttgcaagtt ggattcagaa tgagttaac | 1260 |
| aaggcatgcg aactgaccga ttctagctgg atagagctcg atgaaattgg agaagatgtg | 1320 |

```
gctccaatag aacacattgc aagcatgaga aggaactatt tcacatcaga ggtgtctcat   1380
tgcagggcca ccgaatacat aatgaaagga gtgtacatca atactgccct gcttaatgca   1440
tcttgtgcag caatggatga tttccaactc attccaatga taagcaagtg tcggactaag   1500
gaggggaggc gaaagaccaa cttgtatggt ttcatcataa aaggaagatc ccatttaagg   1560
aatgacaccg acgtggtgaa ctttgtgagc atggagtttt ctctcactga ccctagactt   1620
gaaccacata aatgggagaa gtactgtgtc cttgagatag gagatatgct cataagaagt   1680
gccataggcc aggtttcaag gcccatgttc ttgtatgtga aacaaacgg aacctcaaaa   1740 attaaaatga aatggggaat ggagatgagg cgctgcctcc tccagtcact tcaacaaatt   1800
gagagcatga ttgaagcgga gtcctctgtc aaagagaaag acatgaccaa agagttcttt   1860
gaaaacaaat cagaaacatg gcccattgga gaatccccca aaggcgtgga ggaaagttcc   1920
attgggaagg tctgcaggac tttattagca aaatcggtct tcaacagctt gtatgcatct   1980
ccacaactag aaggcttttc agctgaatca cgaaaactgc ttcttatcgt tcaggcgctt   2040
agggacaacc tggaacctgg gacctttgat cttgggggc tatatgaagc aattgaggag   2100
tgcctgatta atgatccctg ggttttgctc aatgcttctt ggttcaactc cttccttaca   2160
catgcattga gttagttgtg gcagtgctac tatttgctat ccatactgtc caaaaaagta   2220
ccttgtttct act                                                     2233

<210> SEQ ID NO 23
<211> LENGTH: 1775
<212> TYPE: DNA
<213> ORGANISM: Influenza virus

<400> SEQUENCE: 23
agcaaaagca ggggaaaata aaacaacca aatgaaggc aaacctactg gtcctgttat    60
gtgcacttgc agctgcagat gcagacacaa tatgtatagg ctaccatgcg aacaattcaa   120
ccgacactgt tgacacagta ctcgagaaga atgtgacagt gacacactct gttaacctgc   180
tcgaagacag ccacaacgga aaactatgta gattaaaagg aatagcccca ctacaattgg   240
ggaaatgtaa catcgccgga tggctcttgg gaaacccaga atgcgaccca ctgcttccag   300
tgagatcatg gtcctacatt gtagaaacac caaactctga gaatggaata tgttatccag   360
gagatttcat cgactatgag gagctgaggg agcaattgag ctcagtgtca tcattcgaaa   420
gattcgaaat atttcccaaa gaaagctcat ggcccaacca aacacaaac ggagtaacgg   480 cagcatgctc ccatgagggg aaaagcagtt tttacagaaa tttgctatgg ctgacggaga   540
aggagggctc atacccaaag ctgaaaaatt cttatgtgaa caaaaaaggg aaagaagtcc   600
ttgtactgtg gggtattcat cacccgccta acagtaagga caacagaat ctctatcaga   660 atgaaaatgc ttatgtctct gtagtgactt caaattataa caggagattt accccggaaa   720
tagcagaaag acccaaagta agagatcaag ctggaggat gaactattac tggaccttgc   780
taaaacccgg agacacaata atatttgagg caaatggaaa tctaatagca ccaatgtatg   840
ctttcgcact gagtagaggc tttgggtccg gcatcatcac ctcaaacgca tcaatgcatg   900
agtgtaacac gaagtgtcaa acaccctgg gagctataaa cagcagtctc ccttaccaga   960
atatacaccc agtcacaata ggagagtgcc caaaatacgt caggagtgcc aaattgagga   1020
tggttacagg actaaggaac attccgtcca ttcaatccag aggtctattt ggagccattg  1080
ccggttttat tgaaggggga tggactggaa tgatagatgg atggtatggt tatcatcatc  1140
```

| | |
|---|---:|
| agaatgaaca gggatcaggc tatgcagcgg atcaaaaaag cacacaaaat gccattaacg | 1200 |
| ggattacaaa caaggtgaac actgttatcg agaaaatgaa cattcaattc acagctgtgg | 1260 |
| gtaaagaatt caacaaatta gaaaaaagga tggaaaattt aaataaaaaa gttgatgatg | 1320 |
| gatttctgga catttggaca tataatgcag aattgttagt tctactggaa atgaaagga | 1380 |
| ctctggattt ccatgactca aatgtgaaga atctgtatga gaaagtaaaa agccaattaa | 1440 |
| agaataatgc caaagaaatc ggaaatggat gttttgagtt ctaccacaag tgtgacaatg | 1500 |
| aatgcatgga aagtgtaaga aatgggactt atgattatcc caaatattca gaagagtcaa | 1560 |
| agttgaacag ggaaaaggta gatggagtga aattggaatc aatggggatc tatcagattc | 1620 |
| tggcgatcta ctcaactgtc gccagttcac tggtgctttt ggtctccctg ggggcaatca | 1680 |
| gtttctggat gtgttctaat ggatctttgc agtgcagaat atgcatctga gattagaatt | 1740 |
| tcagagatat gaggaaaaac accttgtttc tact | 1775 |

<210> SEQ ID NO 24
<211> LENGTH: 1775
<212> TYPE: DNA
<213> ORGANISM: Influenza virus

<400> SEQUENCE: 24

| | |
|---|---:|
| agcaaaagca ggggaaaata aaaacaacca aaatgaaggc aaacctactg gtcctgttat | 60 |
| gtgcacttgc agctgcagat gctgacacaa tatgtatagg ctaccatgcg aacaattcca | 120 |
| ccgacactgt tgacacagta ctcgagaaga atgtgacagt gacacactct gttaacctcc | 180 |
| tcgaagacag ccacaacggg aaactatgta ttaaaagg aatagcccct ctacaattgg | 240 |
| ggaaatgcaa catcgccgga tggctcttgg ggaacccaga atgcgaccca ctccttccag | 300 |
| tgagatcatg gtcctacatt gtagaaacac caaactctga atgaata tgctatccag | 360 |
| gggatttcat cgactatgag gagctgcgag agcaattgag ctcagtgtca tcattcgaaa | 420 |
| gattcgaaat atttcccaag gaaagctcat ggcccaacca caacacaaac ggagtaacgg | 480 |
| cagcatgctc ccatgagggg aagagcagtt tttacagaaa tctactatgg ctgacggaga | 540 |
| aggagggctc atacccctaag ctgaaaaatt cttatgtgaa caaaaaaggg aaagaagtcc | 600 |
| ttgttctgtg gggtattcat caccgccta acagtaagga caacagaat ctctatcaga | 660 |
| atgaaaatgc ttatgtctct gtagtgactt caaattataa taggagattt ccccgaaa | 720 |
| tagcagaaag acccaaggta agagatcaag ctgggaggat gaactattac tggaccttgc | 780 |
| taaaacccgg agcacaata atattcgagg caaatgaa tctaatagca ccaatgtatg | 840 |
| ctttcgcact gagtagaggc tttgggtccg gcatcatcac ctcaaacgca tcaatgcatg | 900 |
| agtgtaatac gaagtgtcaa acaccctgg gagctataa cagcagtctc ccttaccaga | 960 |
| atatacaccc tgtcacaata ggagagtgcc caaagtacgt caggtcggcc aaattgcgga | 1020 |
| tggttacagg actaaggaac attccgtcca ttcaatccag aggtctattt ggagccattg | 1080 |
| ccggttttat tgaagggggg tggactggaa tgatagatat atggtatggt taccatcatc | 1140 |
| agaatgaaca ggggtcaggc tatgcagcgg atcaaaaaag cacacaaaat gccattaacg | 1200 |
| ggattacaaa caaggtgaac actgttatcg agaaaatgaa cattcaattc acagctgtgg | 1260 |
| gtaaagaatt caacaagtta gaaaaaagga tggaaaattt aaataaaaaa gttgatgatg | 1320 |
| gatttctcga catttggaca tataatgcag aattgctagt tctactggaa atgaacgaa | 1380 |
| ctctggattt ccatgactca aatgtgaaga atctgtatga gaaagtaaaa agccaattaa | 1440 |
| agaataatgc taaagaaatc ggaaatggat gctttgagtt ctaccacaag tgtgacaatg | 1500 |

```
aatgcatgga aagtgtaaga aatgggactt atgattatcc caaatattca gaagagtcaa    1560
agttgaacag ggaaaaggtt gatggagtga aattggaatc aatggggatc tatcagattc    1620
tggcgatcta ctcaactgtc gccagttcac tcgtgctttt ggtctccctg ggggcaatca    1680
gtttctggat gtgttctaat ggatctttgc agtgcagaat atgcatctga gattagaatt    1740
tcagagatat gaggaaaaac acccttgttt ctact                               1775
```

<210> SEQ ID NO 25
<211> LENGTH: 1565
<212> TYPE: DNA
<213> ORGANISM: Influenza virus

<400> SEQUENCE: 25

```
agcaaaagca gggtagataa tcactcactg agtgacatca aaatcatggc gtctcaaggc      60
accaaacgat cttacgaaca gatggagact gatggagaac gccagaatgc cactgaaatc     120
agagcatccg tcggaaaaat gattggtgga attggacgat ctacatcca aatgtgcacc      180 gaactcaaac tcagtgatta tgagggacgg ttgatccaaa acagcttaac aatagagaga     240
atggtgctct ctgcttttga cgaaaggaga aataaatacc ttgaagaaca tcccagtgcg     300
gggaaagatc ctaagaaaac tggaggacct atatacagga gagtaaacgg aaagtggatg     360
agagaactca tcctttatga caaagaagaa ataaggcgaa tctggcgcca agctaataat     420
ggtgacgatg caacggctgg tctgactcac atgatgatct ggcattccaa tttgaatgat     480
gcaacttatc agaggacaag agctcttgtt cgcaccggaa tggatccag gatgtgctct     540 ctgatgcaag gttcaactct ccctaggagg tctggagccg caggtgctgc agtcaaagga     600
gttggaacaa tggtgatgga attggtcaga atgatcaaac gtgggatcaa tgatcggaac     660
ttctggaggg gtgagaatgg acgaaaaaca agaattgctt atgaaagaat gtgcaacatt     720
ctcaaaggga aatttcaaac tgctgcacaa aaagcaatga tggatcaagt gagagagagc     780
cggaacccag ggaatgctga gttcgaagat ctcactttc tagcacggtc tgcactcata     840
ttgagagggt cggttgctca caagtcctgc ctgcctgcct gtgtgtatgg acctgccgta     900
gccagtgggt acgactttga agggagggga tactctctag tcggaataga ccctttcaga     960
ctgcttcaaa acagccaagt gtacagccta atcagaccaa atgagaatcc agcacacaag    1020
agtcaactgg tgtggatggc atgccattct gccgcatttg aagatctaag agtattaagc    1080
ttcatcaaag ggacgaaggt gctcccaaga gggaagcttt ccactagagg agttcaaatt    1140
gcttccaatg aaaatatgga gactatgaat caagtacac ttgaactgag aagcaggtac    1200
tgggccataa ggaccagaag tggaggaaac accaatcaac agagggcatc tgcgggccaa    1260
atcagcatac aacctacgtt ctcagtacag agaaatctcc ttttgacag aacaaccatt    1320 atggcagcat tcaatgggaa tacagagggg agaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500
tcttatttct tcggagacaa tgcagaggag tacgacaatt aaagaaaaat acccttgttt    1560
ctact                                                                1565
```

<210> SEQ ID NO 26
<211> LENGTH: 1565
<212> TYPE: DNA
<213> ORGANISM: Influenza virus

<400> SEQUENCE: 26

```
agcaaaagca gggtagataa tcactcactg agtgacatca aaatcatggc gtctcaaggc    60
accaaacgat cttacgaaca gatggagact gatggagaac gccagaatgc aactgaaatc   120
agagcatccg tgggaaaaat gattggtgga attggaagat tctacatcca aatgtgcact   180
gaactcaaac tcagtgatta tgagggacgg ctgatccaaa acagcttaac aatagagaga   240
atggtgctct ctgcttttga cgaaaggaga aacaaatacc tggaagaaca tcccagtgcg   300
gggaaagacc ctaagaaaac tggaggacct atatacagga gagtaaacgg aagtggatg    360
agagaactca tcctttatga caaagaagaa attaggcgaa tctggagaca agctaataac   420
ggtgacgatg caacggctgg tctgactcat atgatgatct ggcattccaa tctgaatgat   480
gcaacttatc agagaacaag agctcttgtt agaaccggaa tggatcccag gatgtgttct   540
ctgatgcaag gttcaactct cccgaggagg tctggagccg caggcgctgc agtcaaagga   600
gttggaacaa tggtgatgga attggtcaga atgatcaaac gtgggatcaa cgatcggaac   660
ttctggaggg gcgagaatgg acgaaaaaca agaattgctt atgaaagaat gtgcaacatt   720
ctcaaaggga aattccaaac tgctgcacaa aaagcaatga tggatcaggt gagagagtca   780
cggaaccccag gaatgctga gttcgaagat ctcactttc tggcacggtc tgcactcatt   840
ttgagagggt cggttgctca caagtcctgc ctgcctgcct gtgtgtatgg acctgccgta   900
gccagtgggt atgactttga aagggaggga tactctctag tcggaataga cccgttcaga   960
ctgcttcaaa acagccaagt gtactcacta atcagaccaa atgagaatcc agcacacaag  1020
agtcagctgg tgtggatggc atgccattct gcagcatttg aagatctgag agtattaagc  1080
ttcatcaaag gacgaaggt gctcccaaga gggaagcttt ccactagagg agttcagatt  1140
gcttccaatg aaaatatgga gactatgaa tcaagtacac ttgaactgag aagcaggtat  1200
tgggccataa gaaccagaag tggaggaaac accaatcaac agagggcatc tgcgggccaa  1260
atcagcatac agcctacatt ctcagtacag agaaatctcc cctttgacag aacaaccatt  1320
atggcagcat tcaatgggaa cacagagggg agaacatctg acatgaggac cgagatcata  1380
aggatgatgg aaagtgcaag accagaagac gtgtctttcc aggggcgggg agtcttcgag  1440
ctctcggacg aaaaggcagc gagcccgatc gtgccttcct ttgacatgag taatgaagga  1500
tcttatttct tcggagacaa tgcagaggag tacgacaatt aaagaaaaat accctttgttt  1560
ctact                                                              1565
```

<210> SEQ ID NO 27
<211> LENGTH: 1413
<212> TYPE: DNA
<213> ORGANISM: Influenza virus

<400> SEQUENCE: 27

```
agcaaaagca ggagtttaaa atgaatccaa atcagaaaat aataaccatt ggatcaatct    60
gtctggtagt cggactaatt agcctaatat tgcaaatagg aaatataatc tcaatatgga   120
ttagccattc aattcaaact ggaagtcaaa accatactgg aatatgcaac caaaacatca   180
ttacctataa aaatagcacc tgggtaaagg acacaacttc agtgatatta accggcaatt   240
catctctttg tcccatccgt gggtgggcta tatacagcaa agacaatagc ataagaattg   300
gttccaaagg agacgttttt gtcataagag agccctttat ttcatgttct cacttggaat   360
gcaggacctt ttttctgacc caaggtgcct tactgaatga caagcattca gtgggactg    420
ttaaggacag aagcccttat agggccttaa tgagctgccc tgtcggtgaa gctccgtccc   480
```

-continued

```
cgtacaattc aagatttgaa tcggttgctt ggtcagcaag tgcatgtcat gatggcatgg      540
gctggctaac aatcggaatt tcaggtccag ataatggagc agtggctgta ttaaaataca      600
acggcataat aactgaaacc ataaaaagtt ggaggaagaa aatattgagg acacaagagt      660
ctgaatgtgc ctgtgtaaat ggttcatgtt ttactataat gactgatggc ccgagtgatg      720
ggctggcctc gtacaaaatt ttcaagatcg aaaaggggaa ggttactaaa tcaatagagt      780
tgaatgcacc taattctcac tatgaggaat gttcctgtta ccctgatacc ggcaaagtga      840
tgtgtgtgtg cagagacaat tggcatggtt cgaaccggcc atgggtgtct ttcgatcaaa      900
acctggatta tcaaatagga tacatctgca gtggggtttt cggtgacaac ccgcgtcccg      960
aagatggaac aggcagctgt ggtccagtgt atgttgatgg agcaaacgga gtaaagggat     1020
tttcatatag gtatggtaat ggtgtttgga taggaaggac caaaagtcac agttccagac     1080
atgggtttga tgatttggg atcctaatg gatggacaga gactgatagt aagttctctg      1140
tgaggcaaga tgttgtggca atgactgatt ggtcagggta tagcggaagt ttcgttcaac     1200
atcctgagct gacagggcta gactgtatga ggccgtgctt ctgggttgaa ttaatcaggg     1260
gacgacctaa agaaaaaaca atctggacta gtgcgagcag catttctttt tgtgcgtga     1320 atagtgatac tgtagattgg tcttggccag acggtgctga gttgccattc agcattgaca     1380
agtagtctgt tcaaaaaact ccttgtttct act                                  1413
```

<210> SEQ ID NO 28
<211> LENGTH: 1413
<212> TYPE: DNA
<213> ORGANISM: Influenza virus

<400> SEQUENCE: 28

```
agcaaaagca ggagttttaaa atgaatccaa atcagaaaat aataaccatt ggatcaatct      60
gtctggtagt cggactaatt agcctaatat tgcaaatagg gaatataatc tcaatatgga     120
ttagccattc aattcaaact ggaagtcaaa accatactgg aatatgcaac caaaacatca     180
ttacctataa aaatagcacc tgggtaaagg acacaacttc agtcatatta accggcaatt     240
catctctttg tcccatccgt gggtgggcta tatacagcaa agacaatagc ataagaattg     300
gttccaaagg agacgttttt gtcatcagag agccctttat ttcctgttct cacttggaat     360
gcaggacatt ttttctgacg cagggtgcct tattgaatga caagcattca gtgggactg      420 taaaggacag aagtccttat agggccttaa tgagctgccc tgtcggtgag gctccatccc     480
catacaattc aagatttgaa tccgttgctt ggtcagcaag tgcatgccat gatggcatgg      540
gctggcttac aatcggaatt tcagggccag ataatggagc tgtggctgta ttaaaataca     600
atggcatcat aactgaaacc ataaaaagtt ggagaaagaa aatattgaga acacaagagt     660
ctgaatgtgc ttgtgtaaat ggttcatgtt ttactataat gactgatggc ccgagtgacg     720
ggctggcttc gtacaaaatt ttcaagatcg aaaaggggaa ggttactaaa agtatagagt     780
tgaatgcacc taattctcac tatgaggaat gttcctgtta ccctgatacc ggcaaagtga      840
tgtgcgtgtg cagagacaat tggcatggtt ccaaccggcc atgggtgtct ttcgatcaga      900
acttggatta tcaaatagga tacatctgca gtggggtttt cggggacaac ccgcgccccg      960
aagatggaac aggcagctgc ggtccagtgt atgttgatgg ggcaaacgga gtaaagggat     1020
tttcatatag atatggtaat ggtgtatgga taggagggac aaaaagtcac agttccagac     1080 acggggtttga tgatttggg atccaaatg gatggacaga gactgatagt aagttctctg      1140
```

| | |
|---|---:|
| tgaggcagga tgttgtggca atgactgatt ggtcagggta tagtggaagt tcgttcaac | 1200 |
| atcctgagct gacagggttg gactgcatga ggccatgctt ctgggtagaa ttaatcaggg | 1260 |
| ggcgacctaa agaaaaaaca atctggacta gtgcgagcag catttctttt tgtggcgtga | 1320 |
| atagtgatac tgtagattgg tcttggccag acggtgctga gttgccattc agcattgaca | 1380 |
| agtagtctgt tcaaaaaact ccttgtttct act | 1413 |

<210> SEQ ID NO 29
<211> LENGTH: 1027
<212> TYPE: DNA
<213> ORGANISM: Influenza virus

<400> SEQUENCE: 29

| | |
|---|---:|
| agcaaaagca ggtagatatt gaaagatgag tcttctaacc gaggtcgaaa cgtacgtact | 60 |
| ctctatcatc ccgtcaggcc ccctcaaagc cgagatcgca cagagacttg aagatgtctt | 120 |
| tgcagggaag aacaccgatc ttgaggttct catggaatgg ctaaagacaa gaccaatcct | 180 |
| gtcacctctg actaagggga ttttaggatt tgtgttcacg ctcaccgtgc ccagtgagcg | 240 |
| aggactgcag cgtagacgct ttgtccaaaa tgcccttaat gggaacgggg atccaaataa | 300 |
| catggacaaa gcagttaaac tgtataggaa gctcaagagg gagataacat tccatggggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaatccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctagacaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cactattgcc gcaaatatca ttgggatctt gcacttgaca ttgtggattc | 840 |
| ttgatcgtct ttttttcaaa tgcatttacc gtcgctttaa atacggactg aaaggagggc | 900 |
| cttctacgga aggagtgcca aagtctatga gggaagaata tcgaaaggaa cagcagagtg | 960 |
| ctgtggatgc tgacgatggt catttttgtca gcatagagct ggagtaaaaa actaccttgt | 1020 |
| ttctact | 1027 |

<210> SEQ ID NO 30
<211> LENGTH: 1027
<212> TYPE: DNA
<213> ORGANISM: Influenza virus

<400> SEQUENCE: 30

| | |
|---|---:|
| agcaaaagca ggtagatatt gaaagatgag tcttctaacc gaggtcgaaa cgtacgtact | 60 |
| ctctatcatc ccgtcaggcc ccctcaaagc cgagatcgca cagagacttg aagatgtctt | 120 |
| tgcagggaag aacaccgatc tagaggttct catggaatgg ctaaagacaa gaccaatcct | 180 |
| gtcacctctg actaagggaa tttgggatt tgtgttcacg ctcaccgtgc ccagtgagcg | 240 |
| aggactgcag cgtagacgct ttgtccagaa tgcccttaat gggaacggag atccaaataa | 300 |
| catggacaaa gcagttaaac tgtacaggaa gctcaagagg gagataacat tccatggagc | 360 |
| caaagaaatc tcactcagtt actctgcggg tgcacttgcc agttgtatgg gcctaatata | 420 |
| caacaggatg ggggctgtga ctactgaagt ggcatttggt ctggtatgcg caacctgtga | 480 |
| acagattgct gattcccagc atcggtcaca taggcagatg gtgacaacaa ccaatccact | 540 |

```
aatcagacat gagaacagaa tggtcttagc cagcactaca gctaaggcga tggagcaaat      600
ggctggatcg agtgagcagg cagcagaggc catggaggtt gctagtcagg ctaggcaaat      660
ggtgcaggcg atgagaacca ttgggactca ccctagctcc agtgctggtc tgaaaaacga      720
tcttcttgaa aatttgcagg cctatcagaa acgaatgggg gtgcagatgc aacggttcaa      780
gtgatcctct cactattgcc gcaaatatca ttgggatctt gcacttgaca ttgtggattc      840
ttgatcgtct ttttttcaaa tgcatttacc gtcgctttaa atacgactg aaaggagggc       900 cttctacgga aggagtgcca aagtctatga gggaagaata tcgaaaggaa cagcagagtg      960
ctgtggatgc tgacgatggt cattttgtca gcatagagct ggagtaaaaa actaccttgt     1020
ttctact                                                               1027

<210> SEQ ID NO 31
<211> LENGTH: 890
<212> TYPE: DNA
<213> ORGANISM: Influenza virus

<400> SEQUENCE: 31
agcaaaagca gggtgacaaa acataatgg atccaaacac tgtgtcaagc tttcaggtag        60
attgctttct ttggcatgtc cgcaaacgag ttgcagacca agaactaggc gatgccccat      120
tccttgatcg gcttcgccga gatcagaaat ccctaagagg aaggggcagt actctcggtc      180
tggacatcaa gacagccaca cgtgctggaa agcagatagt ggagcggatt ctgaaagaag      240
aatccgatga ggcacttaaa atgaccatgg cctctgtacc tgcgtcgcgt tacctaactg      300
acatgactct tgaggaaatg tcaagggact ggtccatgct catacccaag cagaaagtgg      360
caggccctct tgtatcaga atggaccagg cgatcatgga taagaacatc atactgaaag       420
cgaacttcag tgtgattttt gaccggctgg agactctaat attgctaagg ctttcaccg       480 aagagggagc aattgttggc gaaatttcac cattgccttc tcttccagga catactgctg      540
aggatgtcaa aaatgcagtt ggagtcctca tcggaggact tgaatggaat gataacacag      600
ttcgagtctc tgaaactcta cagagattcg cttggagaag cagtaatgag atgggagac       660 ctccactcac tccaaaacag aaacgagaaa tggcgggaac aattaggtca gaagtttgaa      720
gaaataagat ggttgattga agaagtgaga cacaaactga gataacaga gaatagtttt       780 gagcaaataa catttatgca agccttacat ctattgcttg aagtggagca agagataaga      840
actttctcgt ttcagcttat ttagtactaa aaaacaccct tgtttctact                 890

<210> SEQ ID NO 32
<211> LENGTH: 890
<212> TYPE: DNA
<213> ORGANISM: Influenza virus

<400> SEQUENCE: 32
agcaaaagca gggtgacaaa acataatgg atccaaacac tgtgtcaagc tttcaggtag        60
attgctttct ttggcatgtc cgcaaacgag ttgcagacca agaactaggc gatgccccat      120
tccttgatcg gcttcgccga gatcagaaat ccctaagagg aaggggcagt actctcggtc      180
tggacatcaa gacagctaca cgtgctggga agcagatagt ggagcggatt ctgaaagaag      240
aatccgatga ggcacttaaa atgaccatgg cctctgtacc tgcgtcgcgt tacctaactg      300
acatgactct tgaggaaatg tcaagagact ggtccatgct catacccaag caaaaagtgg      360
caggtcctct ttgtatcaga atggaccagg caatcatgga taagaacatc atactgaaag      420
```

```
cgaacttcag cgtgattttt gaccggctgg agactttaat attgttaaga gctttcaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttagtactaa aaaacaccct tgtttctact              890
```